(12) United States Patent
Ford et al.

(10) Patent No.: US 11,560,461 B2
(45) Date of Patent: Jan. 24, 2023

(54) ADDITIVE FOR FIBER STRENGTHENING

(71) Applicant: North Carolina State University, Raleigh, NC (US)

(72) Inventors: Ericka Ford, Raleigh, NC (US); Chunhong Lu, Raleigh, NC (US); Charles Blackwell, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 564 days.

(21) Appl. No.: 16/493,846

(22) PCT Filed: Apr. 6, 2018

(86) PCT No.: PCT/US2018/026495
§ 371 (c)(1),
(2) Date: Sep. 13, 2019

(87) PCT Pub. No.: WO2018/187710
PCT Pub. Date: Oct. 11, 2018

(65) Prior Publication Data
US 2020/0079930 A1 Mar. 12, 2020

Related U.S. Application Data

(60) Provisional application No. 62/483,204, filed on Apr. 7, 2017.

(51) Int. Cl.
*C08K 5/092* (2006.01)
*C07C 59/285* (2006.01)
(Continued)

(52) U.S. Cl.
CPC .......... *C08K 5/092* (2013.01); *C04B 16/0641* (2013.01); *C04B 16/0658* (2013.01);
(Continued)

(58) Field of Classification Search
CPC ....... C08K 5/092; C07C 59/285; C08F 16/06; C08F 20/44; C08L 29/04; C08L 33/20;
(Continued)

(56) References Cited

U.S. PATENT DOCUMENTS 3,689,622 A 9/1972 Kawai et al.
3,776,994 A 12/1973 Yoshioka et al.
(Continued)

FOREIGN PATENT DOCUMENTS

CA 2132816 * 3/1995 ............... D01F 6/54
CA 2132816 A1 3/1995
(Continued)

OTHER PUBLICATIONS

International Search Report, PCT/US2018/026495, dated Aug. 2, 2018.
(Continued)

*Primary Examiner* — Robert D Harlan
(74) *Attorney, Agent, or Firm* — Michael Best & Friedrich LLP

(57) ABSTRACT

Compositions that include a polymer and an aldaric acid, such as glucaric acid, are disclosed. The compositions may include polyvinyl alcohol and glucaric acid. The compositions may also include polyacrylonitrile and glucaric acid. In addition, the compositions may further include lignin. Also disclosed are fibers including the compositions, methods of making the fibers, and uses of the fibers.

19 Claims, 33 Drawing Sheets

(51) Int. Cl.
  C08F 16/06 (2006.01)
  C08F 20/44 (2006.01)
  C08L 29/04 (2006.01)
  C08L 33/20 (2006.01)
  C04B 16/06 (2006.01)
  D01D 5/06 (2006.01)
  D01F 1/10 (2006.01)
  D01F 6/14 (2006.01)
  D01F 6/18 (2006.01)

(52) U.S. Cl.
  CPC ............ *C07C 59/285* (2013.01); *C08F 16/06* (2013.01); *C08F 20/44* (2013.01); *C08L 29/04* (2013.01); *C08L 33/20* (2013.01); *D01D 5/06* (2013.01); *D01F 1/10* (2013.01); *D01F 6/14* (2013.01); *D01F 6/18* (2013.01); *C08L 2203/12* (2013.01)

(58) Field of Classification Search
  CPC ............. C08L 2203/12; C04B 16/0658; C04B 16/0641; D01D 5/06; D01F 1/10; D01F 6/14; D01F 6/18
  See application file for complete search history.

(56) References Cited

U.S. PATENT DOCUMENTS

| | | | |
|---|---|---|---|
| 5,358,702 | A | 10/1994 | Unger |
| 5,401,576 | A | 3/1995 | Yoon et al. |
| 6,270,567 | B1 | 8/2001 | Matsuo et al. |
| 7,045,184 | B2 | 5/2006 | Scott et al. |
| 7,267,696 | B2 | 9/2007 | Desenne et al. |
| 2004/0054069 | A1 | 3/2004 | Kusudou et al. |
| 2009/0082493 | A1* | 3/2009 | Taylor ................. C09D 133/10 524/320 |
| 2015/0037241 | A1 | 2/2015 | Lehmann et al. |

FOREIGN PATENT DOCUMENTS

| | | |
|---|---|---|
| CN | 101830015 A | 9/2010 |
| EP | 0146084 A2 | 6/1985 |
| EP | 0775486 A1 | 5/1997 |
| JP | S4716724 A | 9/1972 |
| JP | S5035427 A | 4/1975 |
| JP | H02221406 A | 9/1990 |
| JP | H1199090 A | 4/1999 |
| JP | 2002088246 A | 3/2002 |
| JP | 2003238921 A | 8/2003 |
| JP | 2004339643 A | 12/2004 |
| JP | 2008285611 A | 11/2008 |
| RU | 2246459 C2 | 2/2005 |
| WO | 1997/043771 A1 | 11/1997 |
| WO | 1999058468 A1 | 11/1999 |
| WO | 2004/030661 A2 | 4/2004 |
| WO | 2006073540 A2 | 10/2005 |
| WO | WO 2006/073540 A2 * | 7/2006 ............... B32B 3/00 |
| WO | 2009144081 A1 | 12/2009 |
| WO | 2011066191 A1 | 6/2011 |
| WO | 2012156441 A1 | 11/2012 |
| WO | 2013/023432 A1 | 2/2013 |

OTHER PUBLICATIONS

Written Opinion, PCT/US2018/026495, dated Aug. 2, 2018.
Intellectual Property Office of India Examination Report for Application No. 201937040844 dated Mar. 20, 2021 (6 pages including English translation).
European Patent Office Extended Search Report for Application No. 18780452.1 dated Dec. 8, 2020 (9 pages).
Japanese Patent Office Notice of Reasons for Refusal for Application No. 2019-554803 dated Feb. 3, 2022 (7 pages including English translation).
The State Intellectual Property Office of People's Republic of China First Office Action for Application No. 201880037170.3 dated Dec. 23, 2021 (19 pages including English translation).
Ajji et al., "Preparation of poly(vinyl alcohol) hydrogels containing citric or succinic acid using gamma radiation," Radiation Physics and Chemistry, 2005, 74(1):36-41.
Arafat et al., "Biomimetic wet-stable fibres via wet spinning and diacid-based crosslinking of collagen triple helices," Polymer, 2015, vol. 77, pp. 102-112.
Awada et al., "Chemical Modification of Poly(Vinyl Alcohol) in Water," Appl. Sci., 2015, vol. 5, pp. 840-850.
Birck et al., "New crosslinked cast films based on poly(vinyl alcohol): Preparation and physico-chemical properties," Express Polymer Letter, 2014, 8(12):941-952.
Bolto et al., "Crosslinked poly(vinyl alcohol) membranes," Progress in Polymer Science, 2009, 34(9):969-981.
Chae et al., "Stabilization and carbonization of gel spun polyacrylonitrile/single wall carbon nanotube composite fibers," Polymer, 2007, 48(13):3781-3789.
Chunhong, Lu, "Investigating the Structural and Mechanical Reinforcement Mechanisms of Gel Spun Lignin/Polyvinyl Alcohol Fibers" Doctoral Dissertation, Aug. 2017.
Conte et al., "Development of immobilized lysozyme based active film," Journal of Food Engineering, 2007, 78(3):741-745.
Figueiredo et al., "Poly(vinyl alcohol) films crosslinked by glutaraldehyde under mild conditions," Journal of Applied Polymer Science, 2009, 111(6):3074-3080.
Gohil et al., "Studies On The Crosslinking Of Poly (Vinyl Alcohol)," Journal of Polymer Research, 2006, 13(2):161-169.
Hasimi et al., "Transport of water in polyvinyl alcohol films: Effect of thermal treatment and chemical crosslinking," European Polymer Journal, 2008,44(12):4098-4107.
Liu et al., "Gel spinning of polyacrylonitrile fibers with medium molecular weight," Polymer International, 2011, 60(3):453-457.
Lu et al., "Antiplasticizing Behaviors of Glucarate and Lignin Bio-Based Derivates on the Properties of Gel-Spun Poly (Vinyl Alcohol) Fibers," Macromol. Mater. Eng., Apr. 2018, vol. 303, Issue 4, Article 1700523, 16 pages.
Lu et al., "Effect of the Coagulation Bath on the Structure and Mechanical Properties of Gel-Spun Lignin/Poly(vinyl alcohol) Fibers," ACS Sustainable Chem. Eng., Feb. 2017, 5(4) 2949-2959.
Mansur et al., "FTIR spectroscopy characterization of poly (vinyl alcohol) hydrogel with different hydrolysis degree and chemically crosslinked with glutaraldehyde," Materials Science and Engineering: C, 2008, 28(4):539-548.
Martel et al., "Finishing of Polyester Fabrics with Cyclodextrins and Polycarboxylic Acids as Crosslinking Agents," Journal of Inclusion Phenomena and Macrocyclic Chemistry, 2002, 44(1):443-446.
Martel et al., "Water-soluble polymers and gels from the polycondensation between cyclodextrins and poly(carboxylic acid)s: A study of the preparation parameters," Journal of Applied Polymer Science, 2005, 97(2):433-442.
Nalankilli, "Gel Spinning—A Promising Technique for the Production of High Performance Fibres," Man-Made Textiles in India, 1997, 40(6):237-242.
Ruckenstein et al., "Preparation and characteristics of polymer-based large adsorbent particles," Journal of Applied Polymer Science, 1996, 61(11):1949-1956.
Salt et al., "Pervaporation separation of ethylacetate-water mixtures through a crosslinked poly(vinylalcohol) membrane," Vacuum, 2005, 79(3-4):215-220.
Shi et al., "The effect of citric acid on the structural properties and cytotoxicity of the polyvinyl alcohol/starch films when molding at high temperature," Carbohydrate Polymers, 2008, 74(4):763-770.
Smith et al., "Tensile Strength of Highly Oriented Polyethylene. II. Effect of Molecular Weight Distribution," Journal of Polymer Science Part B: Polymer Physics, 1982, vol. 20, pp. 2229-2241.
Sonker et al., "Effects of tungsten disulphide nanotubes and glutaric acid on the thermal and mechanical properties of polyvinyl alcohol," Composite Science and Technology, 2016, vol. 127, pp. 47-53.
Tan et al., "Gel-Spun Polyacrylonitrile Fiber From Pregelled Spinning Solution," Polymer Engineering and Science, 2010, 50(7):1290-1294.

(56) References Cited

OTHER PUBLICATIONS

Wang et al., "Properties of polyvinyl alcohol/xylan composite films with citric acid," Carbohydrate Polymers, 2014, vol. 103, pp. 94-99.
The State Intellectual Property Office of People's Republic of China Second Office Action for Application No. 201880037170.3 dated Jun. 13, 2022 (25 pages including English translation).
Lu, "Investigating the Structural and Mechanical Reinforcement Mechanism of Gel-Spun Lingnin/Poly(vinyl alcohol) Fibers", phD dissertation, Fiber and Polymer Science, North Carolina State University, 2017, pp. 90-98.
Japanese Patent Office Action for Application 2019-554803, dated Sep. 20, 2022 (4 pages with translation).
Korean Patent Office Action for Application 10-2019-7032554, dated Sep. 30, 2022, (13 pages with translation).
Indian Patent Office Action for Application 202117018663, dated Oct. 18, 2022, (6 pages with translation).
Indonesian Patent Office Action for Application P00202102276, dated Nov. 11, 2022, (6 pages with translation).

\* cited by examiner

ADDITIVE FOR FIBER STRENGTHENING

CROSS-REFERENCE TO RELATED APPLICATIONS

This patent application is the U.S. national stage entry, under 35 U.S.C. § 371, of International Application Number PCT/US2018/026495, filed Apr. 6, 2018, which claims priority to U.S. Provisional Patent Application No. 62/483,204, filed Apr. 7, 2017, the entire contents of each of which are hereby incorporated by reference.

BACKGROUND

Polymer-based fibers are widely used in a number of applications, ranging from clothing apparel to concrete reinforcement. However, the cost to produce polymer-based fibers with increased strength (e.g., high-performance fibers) remains a challenge, and thus there is a need for fibers that can be produced with high-performance characteristics but at a more economical cost.

SUMMARY

In one aspect, disclosed are compositions comprising a polymer having a plurality of hydroxyl groups or nitrile groups; and an aldaric acid or a salt thereof.

In another aspect, disclosed are compositions comprising a polymer having a plurality of hydroxyl groups or nitrile groups; and glucaric acid or a salt thereof.

In another aspect, disclosed are compositions comprising a polymer having a plurality of hydroxyl groups; and glucaric acid or a salt thereof.

In another aspect, disclosed are compositions comprising a polymer having a plurality of nitrile groups; and glucaric acid or a salt thereof.

In another aspect, disclosed are fibers including compositions comprising a polymer having a plurality of hydroxyl groups or nitrile groups; and an aldaric acid or a salt thereof.

In another aspect, disclosed are fibers including compositions comprising a polymer having a plurality of hydroxyl groups or nitrile groups; and glucaric acid or a salt thereof.

In another aspect, disclosed are fibers including compositions comprising a polymer having a plurality of hydroxyl groups; and glucaric acid or a salt thereof.

In another aspect, disclosed are fibers including compositions comprising a polymer having a plurality of nitrile groups; and glucaric acid or a salt thereof.

In another aspect, disclosed are methods of making a fiber, the method comprising dissolving a polymer having a plurality of hydroxyl and/or nitrile groups and an aldaric acid or a salt thereof in a first solvent to provide a solution; heating the solution; extruding the solution into a first bath comprising a second solvent to provide a gel-spun fiber; aging the gel-spun fiber to provide an aged gel-spun fiber; and drawing the aged gel-spun fiber through a second bath comprising silicone oil to provide the fiber.

In another aspect, disclosed are methods of making a fiber, the method comprising dissolving a polymer having a plurality of hydroxyl and/or nitrile groups and glucaric acid or a salt thereof in a first solvent to provide a solution; heating the solution; extruding the solution into a first bath comprising a second solvent to provide a gel-spun fiber; aging the gel-spun fiber to provide an aged gel-spun fiber; and drawing the aged gel-spun fiber through a second bath comprising silicone oil to provide the fiber.

BRIEF DESCRIPTION OF THE DRAWINGS

FIG. 5A: tensile strength, FIG. 5B: Young's modulus. FIG. 5C: toughness, and FIG. 5D: strain for GA1 (▲) and GA2 (•).

FIG. 7A: 3750-1000 $cm^{-1}$ and FIG. 7B: 1250-800 $cm^{-1}$.

FIG. 9A: tensile strength; FIG. 9B: Young's modulus; and FIG. 9C: toughness.

FIG. 10A: 5% lignin—(a) and 30% lignin—($b_1$, $b_2$). FIG. 10B: Lignin/GA/PVA fiber with 0.8% GA2 at either 5% lignin—($a_1$, $a_2$) or 30% lignin—($b_1$, $b_2$) imaged with SEM at $x_1$: low resolution and $x_2$: high resolution.

FIG. 11B: 1250-800 $cm^{-1}$. Sample designations represent the ratio of (lignin to PVA)/(glucarate to PVA) in drawn fibers.

FIG. 12B: PVA polymer chain orientation within 30/0.8 lignin/GA2/PVA fibers parallel (∥ or 0°) and perpendicular (⊥ or 90°) to the fiber axis.

- and FIG. 13B: lignin concentration after immersing lignin/GA2/PVA fibers in methanol.

FIG. 14B: 0/0.8, FIG. 14C: 5/0, FIG. 14D: 5/0.8, FIG. 14E: 30/0 and FIG. 14F: 30/0.8 after immersion in water at $x_1$: 25 and $x_2$: 85° C.

FIG. 16B: GA2. Samples were measured at a heating rate of 10° C./min under nitrogen purge at 20 mL/min.

DETAILED DESCRIPTION

1. Definitions

Figure 1:
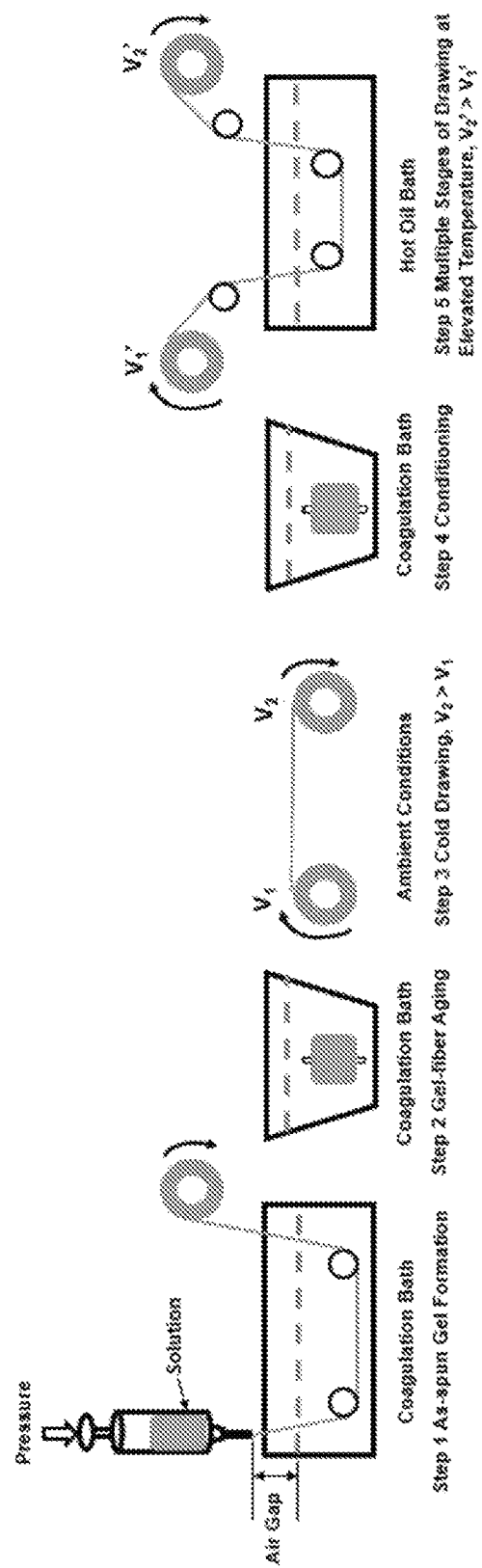
FIG. 1 is a schematic of a gel-spinning method that can be used to provide the disclosed compositions and fibers thereof. The schematic shows five steps: as-spun gel formation (Step 1), aging of gel-fibers (Step 2), cold drawing of gel-fibers (Step 3), conditioning of cold drawn gel-fibers (Step 4) and multi-stage thermal drawing of fibers (Step 5).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements. CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*. Thomas Sorrell, University Science Books, Sausalito, 1999; Smith and March March's *Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkylene," as used herein, refers to a divalent group derived from a straight or branched chain hydrocarbon of 1 to 50 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "$C_y$-$C_z$ alkenyl" means a straight or branched chain hydrocarbon from y to z carbon atoms.

The term "alkyl," as used herein, refers to a straight or branched, saturated hydrocarbon chain containing from 1 to 30 carbon atoms. The term "lower alkyl" or "$C_1$-$C_6$ alkyl" means a straight or branched chain hydrocarbon containing from 1 to 6 carbon atoms. The term "$C_3$-$C_7$ branched alkyl" means a branched chain hydrocarbon containing from 3 to 7 carbon atoms. The term "$C_1$-$C_4$ alkyl" means a straight or branched chain hydrocarbon containing from 1 to 4 carbon atoms. The term "$C_6$-$C_{30}$ alkyl" means a straight or branched chain hydrocarbon containing from 6 to 30 carbon atoms. The term "$C_{12}$-$C_{18}$ alkyl" means a straight or branched chain hydrocarbon containing from 12 to 18 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and n-dodecyl.

The term "hydroxyl" as used herein, means an —OH group.

The term "substituted" refers to a group that may be further substituted with one or more non-hydrogen substituent groups. Substituent groups include, but are not limited to, halogen, =O, =S, cyano, azide, nitro, fluoroalkyl, alkoxyfluoroalkyl, fluoroalkoxy, alkyl, alkenyl, alkynyl, haloalkyl, haloalkoxy, hydroxy, hydroxyalkyl, alkoxy, alkoxyalkyl, amino, alkylamino, acylamino, aminoalkyl, sulfonylamino, sulfinylamino, alkylsulfonyl, aminosulfonyl, triazolyl, alkylsulfinyl, —COOH, alkyvlcarbonyl (e.g., acyl), amide (e.g., C(O)NH$_2$), carbamate (e.g., O(O)NH$_2$), and silyl (e.g., trialkylsilyl).

2. Compositions

Disclosed herein are compositions that include a polymer and an aldaric acid or a salt thereof, such as glucaric acid. The compositions have advantageous properties due in part to the inclusion of the aldaric acid, which make them useful for a number of different applications, including their use as high-performance fibers.

A. Polymer

The compositions can include the polymer where the polymer has a plurality of hydroxyl groups or nitrile groups. The polymer may include a straight or branched polyalkylene (e.g., polyethylene, polypropylene) substituted with the plurality of hydroxyl groups or nitrile groups. In other embodiments, the polymer is a straight or branched polyalkylene substituted with the plurality of hydroxyl groups or nitrile groups. In some embodiments, the straight or branched polyalkylene may be optionally substituted with other substituents other than hydroxyl groups or nitrile groups.

In some embodiments, the polymer may include recurring units of formula (I):

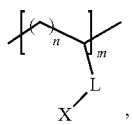

(I)

wherein L is $C_{0-3}$ alkylene; X is —OH or nitrile; n is 1 to 1000; and m is 100 to 100,000.

In some embodiments, L is $C_{0-1}$.

In some embodiments, n is 1 to 100. In some embodiments, n is 1 to 25. In some embodiment, n is 1.

In some embodiments, m is 500 to 100,000. In some embodiments, m is 1,000 to 10,000. In some embodiments, m is 1,000 to 5,000.

The polymer may have a molecular weight of from about 100 kDa to about 400 kDa, such as from about 100 kDa to about 200 kDa or from about 200 kDa to about 300 kDa. In some embodiments, the polymer having a plurality of hydroxyl groups has a molecular weight of from about 100 kDa to about 200 kDa. In some embodiments, the polymer having a plurality of nitrile groups has a molecular weight of from about 200 kDa to about 300 kDa.

The composition may include the polymer at from about 30% to about 99.9% by weight of the composition, such as from about 60% to about 99.9%, from about 75% to about 99%, or from about 80% to about 99% by weight of the composition.

In addition, the polymer may have varying tacticity. For example, the polymer may be atactic, isotactic, or syndiotactic.

i) Polymer with a Plurality of Hydroxyl Groups

In some embodiments, the polymer has a plurality of hydroxyl groups. The polymer may include a straight or branched polyalkylene substituted with the plurality of hydroxyl groups. In other embodiments, the polymer is a straight or branched polyalkylene substituted with the plurality of hydroxyl groups. In some embodiments, the straight or branched polyalkylene is optionally substituted with other substituents other than hydroxyl groups.

In some embodiments, the polymer may include recurring units of formula (II):

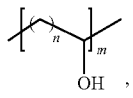

(II)

wherein n is 1 to 1000, and m is 100 to 100,000.

In some embodiments, n is 1 to 100. In some embodiments, n is 1.

In some embodiments m is 100 to 10,000. In some embodiments, m is 1,000 to 5,000.

In some embodiments, the polymer comprises polyvinyl alcohol, polyvinyl alcohol derivatives, polyvinyl alcohol copolymers, or a combination thereof. Polvvinyl alcohol derivatives refer to polymers that are derived from polyvinyl alcohol or polyvinyl alcohol copolymers, which have been modified via chemical substitution, yet still maintain properties that allow it to be useful in the compositions disclosed herein. For example, a polyvinyl alcohol derivative may include polymers where one or more hydroxyl groups of polyvinyl alcohol are converted to alternate functionalities (e.g., azide, amine, silyl) as described in Awada et al., Appl. Sci. (2015) 5, 840-850, and US2004/0054069, which are hereby incorporated by reference. Examples of polyvinyl alcohol copolymers include, but are not limited to, poly (vinyl alcohol-co-ethylene) copolymers, poly(vinyl alcohol-co-propylene) copolymers, and poly(vinyl alcohol-co-vinyl acetate) copolymer. Polyvinyl alcohol copolymers may be random copolymers, block copolymers, alternating copolymers, graft copolymers, or combinations thereof. In some embodiments, the polymer is polyvinyl alcohol.

Polyvinyl alcohol may have a varying degree of hydrolysis. For example, polyvinyl alcohol may be about 80% to about 99.9% hydrolyzed, such as from about 85% to about 99.9%, from about 85% to about 90% or from about 95% to about 99.9% hydrolyzed. In some embodiments, polyvinyl alcohol may be greater than 99% hydrolyzed, greater than 98% hydrolyzed, greater than 95% hydrolyzed, greater than 90% hydrolyzed, greater than 85% hydrolyzed, or greater than 80% hydrolyzed. In addition, polyvinyl alcohol may include a small amount of impurities, such as acetyl content (e.g., polyvinyl acetate) depending on the method of synthesis. For example, polyvinyl alcohol may include less than 5%, less than 4%, less than 3%, less than 2%, less than 1%, less than 0.9%, less than 0.5%, or less than 0.1% impurities by weight of the polyvinyl alcohol.

In some embodiments, the polymer is low molecular weight polyvinyl alcohol or high molecular weight polyvinyl alcohol. For example, low molecular weight polyvinyl alcohol refers to polyvinyl alcohol having a molecular weight less than 100 kDa, such as from about 89 kDa to about 98 kDa having a degree or polymerization of about 2,000. High molecular weight polyvinyl alcohol refers to polyvinyl alcohol having a molecular weight greater than 500 kDa, such as about 774 kDa having a degree or polymerization of about 18,000. In some embodiments, the polymer is polyvinyl alcohol having a molecular weight of from about 146 kDa to about 186 kDa, being about 99% hydrolyzed.

In some embodiments, the composition consists essentially of polyvinyl alcohol and glucaric acid or a salt thereof. In other embodiments, the composition consists of polyvinyl alcohol and glucaric acid or a salt thereof. In these embodiments, the polyvinyl alcohol and glucaric acid may individually include a small amount of impurities as discussed herein.

ii) Polymer with a Plurality of Nitrile Groups

In some embodiments, the polymer has a plurality of nitrile groups. The polymer may include a straight or branched polyalkylene substituted with the plurality of nitrile groups. In other embodiments, the polymer is a straight or branched polyalkylene substituted with the plurality of nitrile groups. In some embodiments, the straight or branched polyalkylene is optionally substituted with other substituents other than nitrile groups.

In some embodiments, the polymer may include recurring units of formula (III):

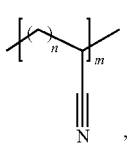

(III)

wherein n is 1 to 1000; and m is 100 to 100,000.

In some embodiments, n is 1 to 100. In some embodiments, n is 1.

In some embodiments m is 100 to 10,000. In some embodiments, m is 1,000 to 5.000.

In some embodiments, the polymer comprises polyacrylonitrile, polyacrylonitrile derivatives, polyacrylonitrile copolymers, or a combination thereof. Polyacrylonitrile derivatives refer to polymers that are derived from polyacrylonitrile or polyacrylonitrile copolymers, which have been modified via chemical substitution, yet still maintain properties that allow it to be useful in the compositions disclosed herein. For example, a polyacrylonitrile derivative may include polymers where one or more nitrile groups of polyacrylonitrile are converted to alternate functionalities. In some embodiments, the polymer is a polyacrylonitrile copolymer of polyacrylonitrile and another polymer selected from the group consisting of acrylic acid, itaconic acid, and acrylates. Polyacrylonitrile copolymers may be random copolymers, block copolymers, alternating copolymers, graft copolymers, or combinations thereof. In some embodiments, the polymer is polyacrylonitrile. In some embodiments, the polymer is polyacrylonitrile having a molecular weight of from about 200 kDa to about 300 kDa.

In addition, polyacrylonitrile may include a small amount of impurities depending on the method of synthesis. For example, polyacrylonitrile may include less than 5%, less than 4%, less than 3%, less than 2%, less than 1%, less than 0.9%, less than 0.5%, or less than 0.1% impurities by weight of polyacrylonitrile.

In some embodiments, the composition consists essentially of polyacrylonitrile and glucaric acid or a salt thereof. In other embodiments, the composition consists of polyacrylonitrile and glucaric acid or a salt thereof. In these embodiments, the polyacrylonitrile and glucaric acid may individually include a small amount of impurities as discussed herein.

B. Aldaric Acid

As mentioned above, the composition includes an aldaric acid or a salt thereof. Aldaric acids are a group of sugar acids, where the terminal hydroxyl and carbonyl groups of the sugars have been replaced by terminal carboxylic acids, and can be characterized by the formula HOOC—(CHOH)$_n$—COOH. Examples of aldaric acid include glucaric acid, tartaric acid, galactaric acid, xylaric acid, ribaric acid, arabinaric acid, ribaric acid, lyxaric acid, mannaric acid, and idaric acid. The following description of the aldaric acid (and salts thereof) can be applied to any of the combinations of polymers as described above.

Chirality of the aldaric acid may influence the compositions and fibers thereof. For example, in some embodiments, the chirality of the aldaric acid can affect the aldaric acid's melting temperature and/or degradation temperature. The aldaric acid's melting temperature and/or degradation temperature can then affect the drawing temperature that can be used to provide fibers that include the aldaric acid, which can ultimately affect mechanical performance of the fiber.

The composition may include the aldaric acid at from about 0.01% to about 10% by weight of the composition, such as from about 0.01% to about 8% or from about 0.8% to about 5% by weight of the composition.

The composition may include the polymer and aldaric acid at a weight ratio of from about 5/1 to about 10,000/1 (polymer/aldaric acid), such as from about 10/1 to about 200/1 or from about 20/1 to about 80/1.

i) Glucaric Acid

In an exemplary embodiment, the aldaric acid is glucaric acid or a salt thereof. The following description of glucaric acid (and salts thereof) can be applied to any of the combinations of polymers as described above. The glucaric acid may include the diacid form of glucaric acid, the lactone form (e.g., 1,4-lactone and 3,6-lactone) of glucaric acid, or combinations thereof.

The glucaric acid may be a salt and can be fully neutralized or partially neutralized. Counter ions of the glucaric acid salt may include, but are not limited to, sodium, potassium, ammonium, zinc, lithium, and combinations thereof. For example, the glucaric acid may be a mono-ammonium salt, a di-ammonium salt, a sodium salt, a potassium salt, or a combination thereof. In some embodiments, the glucaric acid is an ammonium salt of glucaric acid.

The glucaric acid may be

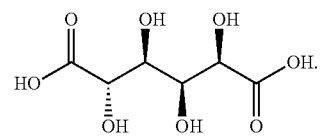

In other embodiments, the glucaric acid may be of formula (IV)

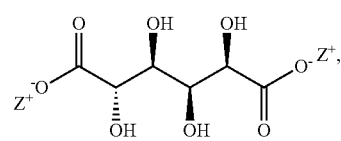

wherein $Z^+$ is selected from the group consisting of hydrogen, sodium, potassium, $N(R^1)_4$, zinc, lithium, and a combination thereof: and $R^1$ is each independently selected from the group consisting of hydrogen and alkyl.

In some embodiments, $R^1$ is each independently selected from the group consisting of hydrogen and $C_1$-$C_{10}$ alkyl. Examples of $N(R^1)_4$ include, but are not limited to, ammonium, mono(alkyl) ammonium, di(alkyl) ammonium, and tetra(alkyl) ammonium.

In some embodiments, the glucaric acid is selected from the group consisting of

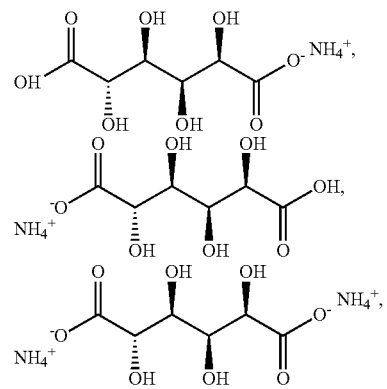

and a combination thereof.

The glucaric acid may be provided via biosynthetic methods. For example, glucaric acid may be provided via microorganism fermentation. As such, the glucaric acid may be provided in an economically friendly manner. In other embodiments, the glucaric acid may be provided via the oxidization of a sugar (e.g., glucose) with an oxidizing agent (e.g., nitric acid).

Depending on the method of providing the glucaric acid, the glucaric acid may have a certain purity level. For example, the glucaric acid may include impurities at from about 0.1% to about 10% by weight of the glucaric acid, such as from about 0.1% to about 5% or from about 0.1% to about 1% by weight of the glucaric acid. Impurities include, but are not limited to, aluminum, boron, calcium, iron, potassium, magnesium, sodium and phosphorus. In some embodiments, the glucaric acid includes mono-ammonium glucarate having potassium and/or sodium impurities.

In some embodiments, the glucaric acid is provided as a combination of the diacid form and the lactone form. For example, the glucaric acid (or salt thereof) may include the diacid form at from about 60% to about 99.9% by weight of the glucaric acid, with the remaining balance being the lactone form. In addition, the glucaric acid may include the lactone form at from about 60% to about 99.9% by weight of the glucaric acid, with the remaining balance being the diacid form. Embodiments that include combinations of the diacid and lactone form may also include impurities as listed above. The percentage (by weight) of each form included in the glucaric acid can vary depending on the pH of the glucaric acid and/or the composition.

The composition may include the glucaric acid at from about 0.01% to about 10% by weight of the composition, such as from about 0.01% to about 8% or from about 0.8% to about 5% by weight of the composition.

The composition may include the polymer and glucaric acid at a weight ratio of from about 5/1 to about 10,000/1 (polymer/glucaric acid), such as from about 10/1 to about 200/1 or from about 20/1 to about 80/1.

C. Additives

The composition may further include an additive that can instill certain characteristics to the composition. Additives include lignin, carbon nanotubes, nanofillers, or combinations thereof. The composition may include the additive at from about 0.1% to about 50% by weight of the composition, such as from about 1% to about 25%, from about 5% to about 30%, or from about 5% to about 20% by weight of the composition. In addition, the composition may include the additive and glucaric acid at a weight ratio (additive/glucaric acid) of from about 0.5/1 to about 20/1, such as from about 1/1 to about 10/1 or from about 2/1 to about 4/1.

In some embodiments, the composition further includes lignin. The composition may include lignin at from about 0.1% to about 50% by weight of the composition, such as from about 1% to about 25%, from about 1% to about 30%, or from about 5% to about 30% by weight of the composition. In addition, the composition may include lignin and glucaric acid at a weight ratio (lignin/glucaric acid) of from about 0.5/1 to about 20/1, such as from about 1/1 to about 10/1 or from about 2/1 to about 4/1. A composition that includes lignin may have less than 10% phase separation, such as less than 9%, less than 8%, less than 7%, less than 6%, less than 5%, less than 4%, less than 3%, less than 2% or less than 1% phase separation by weight of the composition. In addition, a composition that includes lignin may have localization of lignin to different areas of the composition. For example, a fiber comprising a composition that also includes lignin can have lignin localized to the surface of the fiber, where the glucaric acid and polymer can be localized to the core of the fiber.

Lignin can be used in a variety of forms. For example, lignin can be provided as an aqueous pine sawdust paste. In addition, lignin provided as solution may have an acidic pH, such as a pH of 4, pH of 3, or pH of 2. In some embodiments, lignin is provided as lignin having varying degrees of solubility in organic solvents, which can be due to varying molecular weight of the lignin. In some embodiments, the lignin can be purified by dissolving in a solvent (e.g., acetone) and then filtered to remove insoluble lignin fractions. This can improve drawability (e.g., higher fiber stretch and/or less breaks during drawing) of fibers that include lignin.

In addition, lignin may include a small amount of impurities depending on the method it is provided by. For example, lignin may include less than 5%, less than 4%, less than 3%, less than 2%, less than 1%, less than 0.9%, less than 0.5%, or less than 0.1% impurities by weight of lignin. Impurities associated with lignin may include, but are not limited to, ash and hemicellulose.

In some embodiments, the composition consists essentially of polyvinyl alcohol, glucaric acid or a salt thereof, and lignin. In other embodiments, the composition consists of polyvinyl alcohol, glucaric acid or a salt thereof, and lignin. In these embodiments, the polyvinyl alcohol, glucaric acid and lignin may individually include a small amount of impurities as listed above.

In some embodiments, the composition consists essentially of polyacrylonitrile, glucaric acid or a salt thereof, and lignin. In other embodiments, the composition consists of polyacrylonitrile, glucaric acid or a salt thereof, and lignin. In these embodiments, the polyacrylonitrile, glucaric acid and lignin may individually include a small amount of impurities as listed above.

D. Fibers Including the Compositions

The composition may be included as part of a fiber, and in some embodiments, the composition is a fiber. The fiber including the polymer and the aldaric acid, such as glucaric acid, as described above, has unique properties that make it advantageous to numerous technologies that utilize high-strength fibers. It is hypothesized, without being bound by any particular theory, that the aldaric acid plasticizes the flow of polymer chains during processes of fiber stretching, and ultimately increases fiber strength. For example, fiber strengthening may be caused by chain slippage (during processing) which can allow for higher fiber draw ratios, molecular/chain alignment in the fiber microstructure, and can decrease the linear density of fibers. The fiber can be provided through a number of different processes, such as meltblown, spunbond, and/or gel-spun processes. Accordingly, the fiber may be a meltblown fiber, spunbond fiber, and/or a gel-spun fiber. Depending on the method used to provide the fiber it can vary in diameter. For example, the fiber may have a diameter of from about 10 μm to about 50 μm, such as from about 18 μm to about 40 μm or from about 20 μm to about 40 μm.

Generally, the weight percentages and weight ratios of the composition regarding the polymer, the aldaric acid (e.g., glucaric acid), and the additive (e.g., lignin) can be applied to the weight percentages of the fiber. For the purposes of brevity they will not be repeated here.

Due in part to the combination of the polymer and the aldaric acid, the fiber may have increased tenacity. The fiber may have a tenacity of from about 3 g/den to about 15 g/den. The fiber may have a tenacity of greater than 5 g/den, greater than 6 g/den, greater than 7 g/den, greater than 8 g/den, or greater than 9 g/den. In addition, the fiber including the polymer and the aldaric acid may have an increased tenacity relative to a fiber including the same polymer (of the same molecular weight) but without the aldaric acid. For example, the fiber may have a tenacity of at least 1.5×, at least 2×, at least 2.5×, at least 3×, at least 4×, at least 5×, or at least 1.0× the tenacity of a fiber including the same polymer (of the same molecular weight) but without the aldaric acid.

The fiber may have a specific modulus of from about 200 g/den to about 1200 g/den. The fiber may have a specific modulus of greater than 230 g/den, greater than 250 g/den, greater than 300 g/den, greater than 350 g/den, greater than 400 g/den, or greater than 450 g/den.

The fiber may have a tensile strength of from about 150 MPa to about 2000 MPa. The fiber may have a tensile strength of greater than 500 MPa, greater than 550 MPa, greater than 600 MPa, greater than 650 MPa, greater than 700 MPa, greater than 750 MPa, greater than 800 MPa, greater than 900 MPa, or greater than 1000 MPa.

The fiber may have a linear density of from about 3 denier to about 30 denier, such as about 3 denier to about 20 denier or about 3 denier to about 15 denier. The fiber may have a linear density of less than 17 denier, less than 16 denier, less than 15 denier, less than 14 denier, less than 13 denier, less than 12 denier, less than 11 denier, less than 10 denier, less than 9 denier, less than 8 denier, less than 7 denier, or less than 6 denier.

i. Methods of Making the Fibers

As discussed above, the fiber can be provided via a number of different techniques. In an exemplary embodiment, the fiber is provided through a gel-spinning method. The gel-spinning method may include dissolving a polymer having a plurality of hydroxyl and/or nitrile groups and an aldaric acid or a salt thereof in a first solvent to provide a solution. In an exemplary embodiment, the aldaric acid is glucaric acid. In addition, an additive, such as lignin, can be added to the solution. The description of the polymer, the aldaric acid and the glucaric acid, and the additive from above can be applied to the methods described herein.

The first solvent can be any suitable solvent that dissolves the polymer and the aldaric acid, as well as any other optional components (e.g., lignin). The first solvent may include DMSO, water, urea or combinations thereof. In some embodiments, the first solvent is a mixture of DMSO and water at different volume percentages of DMSO/water. For example, the first solvent may include about 80% v/v DMSO and 20% v/v water.

The polymer and the aldaric acid may be present at varying amounts in the solution. For example, the polymer may be present in the solution at from about 60% to about 99.9% by weight/volume. In addition, the aldaric acid may be present in the solution at from about 0.01% to about 5% by weight/volume. In embodiments where an additive, such as lignin, is present, the additive can be present in the solution at from about 0.1% to about 5% by weight/volume.

The solution may then be heated, e.g., to a temperature of from about 70° C. to about 110° C. for a period of time, such as for about 1 minute to about 1 hour. After the solution has been heated for a period of time it may then be extruded through an orifice under pressure into a first bath comprising a second solvent to provide a gel-spun fiber. The diameter of the orifice and pressure applied can vary depending on the type of fiber desired. For example, an orifice can be supplied via a 19-gauge needle having an inner diameter of about 0.69 mm. The air gap between the orifice and the first bath can be from about 1 mm to about 10 mm, such as from about 2 mm to about 8 mm or from about 2 mm to about 7 mm.

In addition, the second solvent may be at a temperature lower than that of the solution (e.g., 0° C., −10° C., −20° C., −25° C., or −35° C.), and can include different solvents. In some embodiments, the second solvent is at a temperature of from about −35° C. to about 0° C. The second solvent may include methanol, acetone, isopropanol, water or combinations thereof. In some embodiments, the second solvent is at −25° C. and includes a mixture of methanol and acetone. The gel-spun fiber, following coagulation in the first bath, can be collected onto a rotating winder.

Once the gel-spun fiber is provided, it can be aged within a third bath that includes the same or similar solvents as the first bath, but at a higher temperature (e.g., greater than 0° C.) than the first bath to provide an aged gel-spun fiber. Gel-spun fibers can be aged for about 1 hour to about 48 hours. In some embodiments, the gel-spun fiber is aged in the third bath at 5° C. for 24 hours. Through this step the gel-spun fibers (and aged gel-spun fibers) may also be referred to as polymer gels.

The aged gel-spun fiber can be drawn through a second bath comprising silicone oil to provide the disclosed fibers. The addition of the aldaric acid (e.g., glucaric acid) or a salt thereof can aid in the processing of polymers in the second bath into fibers with improved properties. For example, the presence of the aldaric acid can influence the thermal properties of the polymer gel-fibers by decreasing their melting temperature, which can result in higher draw ratios. The drawing can be done in 1 to 4 stages at elevated temperatures, such as from about 90° C. to about 240° C.

In some embodiments, the drawing is done in 4 stages. The drawing of stage 1 can be performed at a temperature of from about 90° C. to about 140° C. The drawing of stage 2 can be performed at a temperature of from about 145° C. to about 190° C. The drawing of stage 3 can be performed at a temperature of from about 190° C. to about 205° C. The drawing of stage 4 can be performed at a temperature of from about 200° C. to about 240° C.

Varying feed rates and draw ratios can be used in the disclosed methods. For example, the method may include feed rates of from about 0.1 meters/minute (m/min) to about 20 m/min. In addition, the method may include draw ratios of from about 1 to about 20. In some embodiments, the method may have a total draw ratio of from about 25 to about 160, such as from about 30 to about 150 or from about 35 to about 85. As used herein, "total draw ratio" refers to the cumulative draw ratio of each draw stage performed in the second bath comprising silicone oil.

In some embodiments, the aged gel-spun fibers can undergo a drawing step done at ambient conditions, which can also be referred to as cold drawing. This is typically done prior to drawing through the silicone oil bath. Fibers that undergo cold drawing can also undergo conditioning in a fourth bath prior to drawing through the silicone oil. This conditioning of the fibers in the fourth bath can aid in aligning the fibers prior to drawing in silicone oil. The fourth bath may include the same or similar solvents as the third bath.

An example of a gel-spinning technique can be found in ACS Sustainable Chemistry Engineering. "*Effect of the Coagulation Bath on the Structure and Mechanical Properties of Gel-Spun Lignin/Poly(vinyl alcohol) Fibers,*" 2017, which is incorporated by reference in its entirety, and is further detailed below in the Examples.

ii. Uses of the Fibers

As mentioned above, the disclosed fiber can be used in a number of different applications due to its advantageous properties. One such application is the use of the fiber as a concrete/cement additive, where it may act as a reinforcing fiber within concrete. In addition, the fiber may be included as part of a fibrous article. For example, the fiber may be included in a fibrous article selected from the group consisting of yarn, fabric, melt-blown web, spunbonded web, gel-spun web, thermobonded web, hydroentangled web, nonwoven fabric, and a combination thereof.

In addition, the fiber may be used in applications where high-performance fibers are needed. Examples of these type of applications include precursors for carbon fibers, tire cords, radiation shieldings, and fiber reinforced plastics.

4. Examples

The compositions and methods of the invention will be better understood by reference to the following examples, which are intended as an illustration of and not a limitation upon the scope of the invention.

Example 1

PVA/Glucaric Acid Fibers—I

Polyvinyl alcohol (PVA, having a molecular weight of 146-186 kg/mol and 99% hydrolysis, was purchased from Sigma-Aldrich). Aqueous raw pine sawdust lignin paste (project no. L28) at pH 3 was provided by Pure Lignin Environmental Technology (PLET). Lignin was extracted from wood pulp using a weak-acid hydrolysis treatment. Solvents were used as-received: dimethyl sulfoxide (DMSO) from Sigma-Aldrich and acetone and methanol from BDH Chemicals. Monoammonium glucarate, having potassium or sodium impurities, was provided by Kalion. Glucaric acid was added to the polymer solution (and optionally with lignin) at % w/v's of 0, 0.8, 1.6, 3 and 5.

Spinning dopes of PVA, PVA/glucaric acid, PVA/glucaric acid/lignin and lignin/PVA were prepared. PVA powder (10 g) was dissolved in 100 mL of 80/20 (v/v) DMSO/distilled water under constant stirring at 85° C. for 1 h. PVA powder and glucaric acid were dissolved together in DMSO/distilled water under constant stirring at 85° C. for 1 h to prepare glucaric acid spinning dopes. Lignin/PVA dopes, at weight ratios of up to 50% (w/w) lignin to polymer, were also dissolved in 80/20 (v/v) DMSO/distilled water at 85° C. To obtain a homogeneous blend of PVA and lignin, PVA was dissolved in DMSO/water and lignin was dissolved separately in DMSO before adding both together. The final concentration of PVA in the spinning dopes was 10 g/dL.

A schematic of the gel-spinning process is shown in FIG. 1, wherein step 2 and step 4 are optional. The PVA-based spinning dopes were dispensed from a steel high-pressure syringe. The syringe was heated to 85° C. before extrusion of dopes through a 19-gauge syringe needle (0.69 mm inner diameter). Afterward, the dope gelled in a −25° C. coagulation bath. The syringe tip to coagulation bath distance was 3-5 mm. The resulting as-spun gel fibers were collected onto a rotating winder and later immersed in the 5° C. coagulation bath for 24 h. Fibers were drawn through one to four stages of silicone oil at elevated temperatures of 90-240° C. (FIG. 1—Step 5). The draw ratio (DR) at each stage of fiber drawing was calculated as $$DR = V_2/V_1 \quad \text{(Equation 1)}$$

where $V_1$ is the velocity of the fiber feeding winder and $V_2$ is the velocity of the fiber take-up winder.

It was seen that glucaric acid (GA) improved the processability of polyvinyl alcohol fibers to ultimately achieve higher mechanical performance at up to 1.6% GA. The 2% GA limit to performance enhancement may be molecular weight dependent.

Using the disclosed gel-spinning technique for fiber spinning (see FIG. 1), the mechanical strength of fibers more than doubled with the addition of 1.6% GA (see Table 1). Based on specific modulus results, fiber stiffness increased considerably: from 114 g/den at 0% GA to 427 g/den at 1.6% GA. As can be seen in Table 2, modulus values represent those belonging to high performance fibers.

TABLE 1

Mechanical Properties of Polyvinyl Alcohol/Glucaric Acid Fibers

| Fiber | Linear density (denier) | Tensile strength (MPa) | Modulus (GPa) |
|---|---|---|---|
| Neat PVA | 18 | 340 ± 84 | 20 ± 3 |
| 0.8% GA/PVA | 11 | 752 ± 49 | 34 ± 2 |
| 1.6% GA/PVA | 7 | 1024 ± 75 | 48 ± 5 |
| 3% GA/PVA | 12 | 850 ± 50 | 32 ± 6 |
| 5% GA/PVA | 9 | 638 ± 28 | 29 ± 1 |

| Fiber | Linear density (denier) | Tenacity (g/den) | Specific Modulus (g/den) |
|---|---|---|---|
| Neat PVA | 18 | 4.3 ± 0.2 | 203 ± 32 |
| 0.8% GA/PVA | 11 | 7.0 ± 0.5 | 339 ± 20 |
| 1.6% GA/PVA | 7 | 8.9 ± 0.7 | 427 ± 40 |
| 3% GA/PVA | 12 | 7.1 ± 0.4 | 319 ± 58 |
| 5% GA/PVA | 9 | 5.1 ± 0.2 | 231 ± 12 |

| Fiber | Linear density (denier) | Tenacity (cN/dtex)* | Specific Modulus (cN/dtex) |
|---|---|---|---|
| Neat PVA | 18 | 3.8 ± 0.7 | 179 ± 28 |
| 0.8% GA/PVA | 11 | 6.2 ± 0.4 | 299 ± 18 |
| 1.6% GA/PVA | 7 | 7.9 ± 0.6 | 377 ± 35 |
| 3% GA/PVA | 12 | 6.3 ± 0.4 | 282 ± 51 |
| 5% GA/PVA | 9 | 4.5 ± 0.2 | 204 ± 11 |

*cN/dtex = g/den divided by 1.1325

TABLE 2

Mechanical Properties of Polyvinyl Alcohol/Glucaric Acid/Lignin Fibers

| Fiber | Linear density (denier) | Tensile strength (MPa) | Young's modulus (GPa) |
|---|---|---|---|
| 5% lignin | 9.4 | 1072 ± 85 | 36 ± 3 |
| 5% lignin/0.8% GA | 8.2 | 1036 ± 75 | 41 ± 5 |
| 5% lignin/1.6% GA | 8.2 | 810 ± 53 | 33 ± 2 |

TABLE 3

Mechanical Properties of Fiber Classes

| | Tensile Strength | Tensile Modulus |
|---|---|---|
| Textile Fibers | Up to 7 g/den <1 GPa | 10-30 g/den <10 GPa |
| Industrial Fibers | 7 to 10 g/den >1 GPa | 30-100 g/den >10 GPa |
| High Performance Fibers | 20-50 g/den 3-6 GPa | 200-2500 g/den 50-600 GPa |

References for data in table 3, all of which are incorporated by reference herein in their entirety:

Hearle, J. W. S., ed. High-performance Fibres. Woodhead Publishing Limited series on fibres, ed. J. E. McIntyre. 2001, The Textile Institute Woodhead Publishing Limited: Boca Raton. 329.

Nalankilli, G., Gel Spinning—A Promising Technique for the Production of High Performance Fibres. Man-Made Textiles in India, 1997, 40(6): p. 237-242.

Smith, P., P. J. Lemstra, and J. P. L. Pijpers, Tensile Strength of Highly Oriented Polyethylene. II. Effect of Molecular Weight Distribution. Journal of Polymer Science Part B: Polymer Physics. 1982, 20: p. 2229-2241.

Example 2

PVA/Glucaric Acid Fibers—II

Materials & Methods

Materials:

Atactic PVA (molecular weight 146-186 kg/mole, 99% hydrolysis) was purchased from Sigma Aldrich. Two glucarate salts were donated by Kalion, Inc. Kalion produces glucaric acid through a fermentation-based process. Type 1 or GA1 is an ammonium salt purified by ion exchange chromatography. GA1 contained less than 1% of potassium and sodium ions. Table 4 details the elemental analysis of ammonium glucarates purified by ion exchange chromatography. Type 2 or GA2 is a mono-ammonium salt of glucaric acid. Aqueous raw pine sawdust lignin paste at pH 3 was provided by Pure Lignin Environmental Technology (PLET), LLC. Solvents were used as-received: dimethyl sulfoxide (DMSO from Sigma Aldrich), acetone and methanol (both from BDH Chemicals), and distilled water.

Spinning Dope Preparation: 10 g/dL of PVA powder were dissolved in 80/20 (v/v) DMSO/water at 85° C. The dope was stirred for ~1 h until completely dissolved. Glucarate (GA1 or GA2) were added to dopes at up to 3% (weight/weight, w/w) of polymer.

Spinning dopes of PVA/lignin, at weight ratios of 5 and 30% (w/w) lignin to polymer, were prepared according to the method described and illustrated within Lu et al., *ACS Sustainable Chemistry & Engineering* 2017, 5 (4), 2949-2959, which is incorporated by reference herein in its entirety. GA2, at 0.8% of polymer, were added to lignin/PVA spinning dopes, containing 5 or 30% lignin. Spinning dopes were stirred continuously at 85° C. for 1 h.

Gel Spinning:

Gel-spinning of modified PVA fibers is illustrated in FIG. 1 as five steps. In Step 1, 50 mL of each spinning dope was loaded into steel high-pressure syringe, which was then heated to 85° C. with a constant voltage (120 V) heating belt. Spinning dopes were extruded through a 19-gauge (0.69 mm inner diameter) syringe needle. The air gap between the syringe tip and coagulation bath was between 3-5 mm. As-spun gel-fibers were coagulated at −25° C. in a solvent bath and then collected onto a rotating winder. Afterwards, as-spun gel-fibers were aged in coagulating solvents for 24 h (Step 2).

Step 2: The solvent bath composition for coagulation was also used to age as-spun gel-fiber. Pure methanol was used to process gels from neat PVA and GA/PVA spinning dopes. A mixture of 15/85 (volume/volume, v/v) methanol/acetone was used to process gels from lignin/GA/PVA dopes. Solvent mixtures were formulated to prevent lignin diffusion from gel-fibers—at least 80% acetone was used in the coagulation bath.

Gel-fibers from 0.3% GA1/PVA dopes undergo cold drawing at ambient conditions (Step 3) and conditioning in methanol solvent (Step 4) for 24 h to align fibers before thermal drawing (Step 5). Other gel-fibers were directly drawn through silicone oil baths (Step 5) after gel-fiber aging (Step 2). For each stage of drawing, draw ratio (DR) was calculated by Equation 1. Fibers were thermally drawn in four consecutive stages until fully drawn fibers were obtained (Step 5).

Gel Melting: The gel melting point of GA/PVA gels was measured according to the method described by Ryan et al., *The Journal of Physical Chemistry* 1965, 69 (10), 3384-3400 (which is incorporated by reference herein in its entirety) and Lu et al., *ACS Sustainable Chemistry & Engineering* 2017, 5 (4), 2949-2959. GA/PVA dopes were added to capillary tubes. Capillary tubes were capped at one end. Capped ends were placed in methanol baths of −25° C. for 1 min until dopes gelled. Then, capillaries of gelled polymer were placed upside down in a test tube, alongside a thermocouple. The test tube was positioned in a Thiele tube filled with silicone oil. The Thiele tube was gradually heated to measure the gel melting point, as defined as the temperature when dissolved gel flows to the bottom of the capillary.

Thermal Decomposition of Glucarate:

Thermal decomposition of GA1 and GA2 were measured by Perkin Elmer Pyris 1 Thermogravimetric Analyzers

TABLE 4

Elemental Analysis of Ammonium Glucarates Purified by Ion Exchange Chromatography

| | Elemental Analysis | | | | | ICP-OES (mg/kg) | | | | | | | | | |
|---|---|---|---|---|---|---|---|---|---|---|---|---|---|---|---|
| | C (%) | H (%) | N (%) | ROI (%) | H2O (%) | Al | B | Ca | Fe | K | Mg | Na | P | Total | % |
| Crystals 1 (1$^{st}$ pass) | 31.56 | 5.68 | 5.86 | 0.21 | 0.14 | 3 | | 4 | 3 | 6800 | 4 | 269 | 217 | 7300 | 0.73 |
| Crystals 3 (2$^{nd}$ pass) | 30.52 | 5.62 | 6.04 | 3.24 | 0.55 | 107 | 8 | 22 | 4 | 7500 | 30 | 4400 | 1000 | 13071 | 1.31 |
| Crystals 5 (1$^{st}$ pass) | 31.54 | 5.66 | 5.87 | 1.65 | 0.22 | 8 | 5 | 10 | 1 | 6200 | 3 | 236 | 112 | 6575 | 0.66 |
| Crystals 6 (2$^{nd}$ pass) | 31.16 | 5.61 | 5.97 | 2.42 | 0.62 | 13 | 36 | 14 | 4 | 8100 | 21 | 2100 | 867 | 11155 | 1.12 |
| Crystals 7 (1$^{st}$ pass) | 31.59 | 5.72 | 5.83 | 1.64 | 0.1 | 6 | 3 | 4 | 1 | 7500 | 1 | 151 | 85 | 7751 | 0.78 |
| Crystals 8 (2$^{nd}$ pass) | 19.15 | 5.19 | 6.85 | 20.52 | 12.69 | | | 12 | 3 | 9400 | 15 | 67800 | 926 | 78156 | 7.82 |
| Average | 31.33 | 5.67 | 5.91 | | | 1$^{st}$ Pass Crystals: ROI = 1.2, ICP-OES total = 7,066 mg/kg | | | | | | | | | |
| Predicted, NH$_4$ salt (C$_6$H$_{13}$O$_8$N, MW = 227) | 31.72 | 5.73 | 6.16 | | | 2$^{nd}$ Pass Crystal: ROI = 2.83, ICP-OES total = 12,113 mg/kg | | | | | | | | | |
| Predicted, free acid (C$_6$H$_{10}$O$_8$, MW = 210) | 34.28 | 4.76 | 0 | | | | | | | | | | | | |

(TGA) in nitrogen purge gas at 20 mL/min. The heating rate was 10° C./min from room temperature to 300° C.

Mechanical Testing:

Mechanical properties were obtained from a sample size of 10-15 fibers on the MTS-Q per ASTM D 3379. Strain rate was 15 mm/min, and gauge length was 25 mm. Crosssectional area A was calculated gravimetrically from the linear density, d, of fiber by (Equation 2).

$$A = \frac{d}{\rho} \quad \text{(Equation 2)}$$

After rinsing drawn fiber in isopropyl alcohol to remove oil residue, that mass of 3 m of fibers was measured. The volumetric density, ρ, in Equation 3 was representative of composite fiber.

$$\rho = \rho_{PVA}(1-w_{f1}-w_{f2}) + \rho_{lignin}w_{f1} + \rho_{GA}w_{f2} \quad \text{(Equation 3)}$$

where $w_{f1}$ and $w_{f2}$ refer to the weight fraction of lignin and glucarate in composite fiber, respectively. PVA's density ($\rho_{PVA}$) and lignin's density ($\rho_{lignin}$) share the same value of 1.3 g/cm$^3$. Glucaric acid density is 1.9 g/cm$^3$.

Tensile toughness of each fiber was calculated from the integration of stress-strain curves. It is the energy absorbed until fiber breaks.

Image Analysis:

After mechanical testing, the fracture tips of fibers were sputter coated with 60/40 (w/wA) gold/palladium mixture. FEI Verios 460L Scanning Electron Microscopy (SEM) at 2 kV accelerating voltage were employed for imaging.

Fiber Structural Analysis:

Infrared (IR) spectra of modified PVA fibers, lignin and GA2 powders were acquired by NICOLET iS50 spectrophotometer using 128 scans and 4 cm$^{-1}$ spectral resolution. Inter- and intramolecular hydrogen bonding among PVA chains and additives were analyzed from IR absorbance in the 3000-3750 cm$^{-1}$ range, which was normalized at 3345 cm$^{-1}$. Peak height of hydrogen bonding ($I_{(OH)}$) of fibers in the range of 3306-3345 cm$^{-1}$ were obtained to compare the intensities of hydrogen bonding within modified PVA fibers. Absorbance at 1144 cm$^{-1}$ corresponds to symmetric C—C stretching along the polymer chain, from which neighboring hydroxyl (—OH) groups engage in intra/intermolecular hydrogen bonding. To normalize IR absorbance spectra, the 854 cm$^{-1}$ (C—C stretching) peak was used as the reference band.

Percent crystallinity ($X_C$) of polymer is expressed by Equation 4:

$$Xc(\%) = \left(a + b\frac{A_{(1144+1130)}}{A_{854}}\right) \times 100\% \quad \text{(Equation 4)}$$

where, A and B are constants. Values for A and B are calculated from known values of percent crystallinity from X-ray diffraction. Absorption areas for $A_{Crystalline(1144+1130)}/A_{Reference,854}$ were calculated from infrared spectra with OriginPro 8 software. Absorbance ratios of crystalline PVA (1144 and 1130 cm$^{-1}$) conformations to reference peak (i.e. $A_{(1144+1130)}/A_{854}$) were used as indices of fiber crystallinity and to compare the relative crystallinity of each fiber.

The molecular anisotropy of modified PVA fibers was quantified using polarized Raman spectroscopy. Spectra parallel and perpendicular to the axis of fiber bundles (~30 fibers) were obtained on the Bayspec Normadic Confocal Raman Microscope. Parameters included 10×objective infrared lens, 785 nm laser at 102 mW (based on maximum value of 255 mW), sample exposure time of 3 s and an acquisition number of 10. Raman spectra were normalized at 1550 cm$^{-1}$ for studies on lignin's molecular anisotropy and 2910 cm$^{-1}$ for studies of PVA's main-chain and hydroxyl group orientation.

Raman anisotropy (R) in Equation 5 represented the orientation of molecular groups;

$$R = \frac{I_{\parallel}}{I_{\perp}} \quad \text{(Equation 5)}$$

where $I_{\parallel}$ and $I_{\perp}$ are the peak intensities at polarization angles that were in parallel (∥) or perpendicular to the fiber axis. Herman's orientation factor f for lignin aromatic functional groups within fibers is calculated by Equation 6:

$$f = \frac{R-1}{R+4} \quad \text{(Equation 6)}$$

where R=1 and f=0 for randomly aligned molecules and R=∞ and f=1 for perfectly aligned molecules.

To understand the location of lignin within modified PVA fibers' structure, lignin migration from fiber structure into methanol solvent was quantitatively analyzed by UV-vis Spectroscopy. Lignin was dissolved in 20 mL of methanol at 85° C. to prepare the stock solution of 4.2 g/L. Stock solution was further diluted with methanol into four lignin solutions: 26, 53, 140 and 210 mg/L. 6 mg of each modified PVA fiber were placed in 20 mL of methanol at 85° C. for 24 h. then fibers were removed from solution before testing. Samples were designated in terms of (lignin to PVA)/(GA2 to PVA) weight ratios of 0/0, 0/0.8, 5/0, 5/0.8, 30/0 and 30/0.8.

Figure 15:
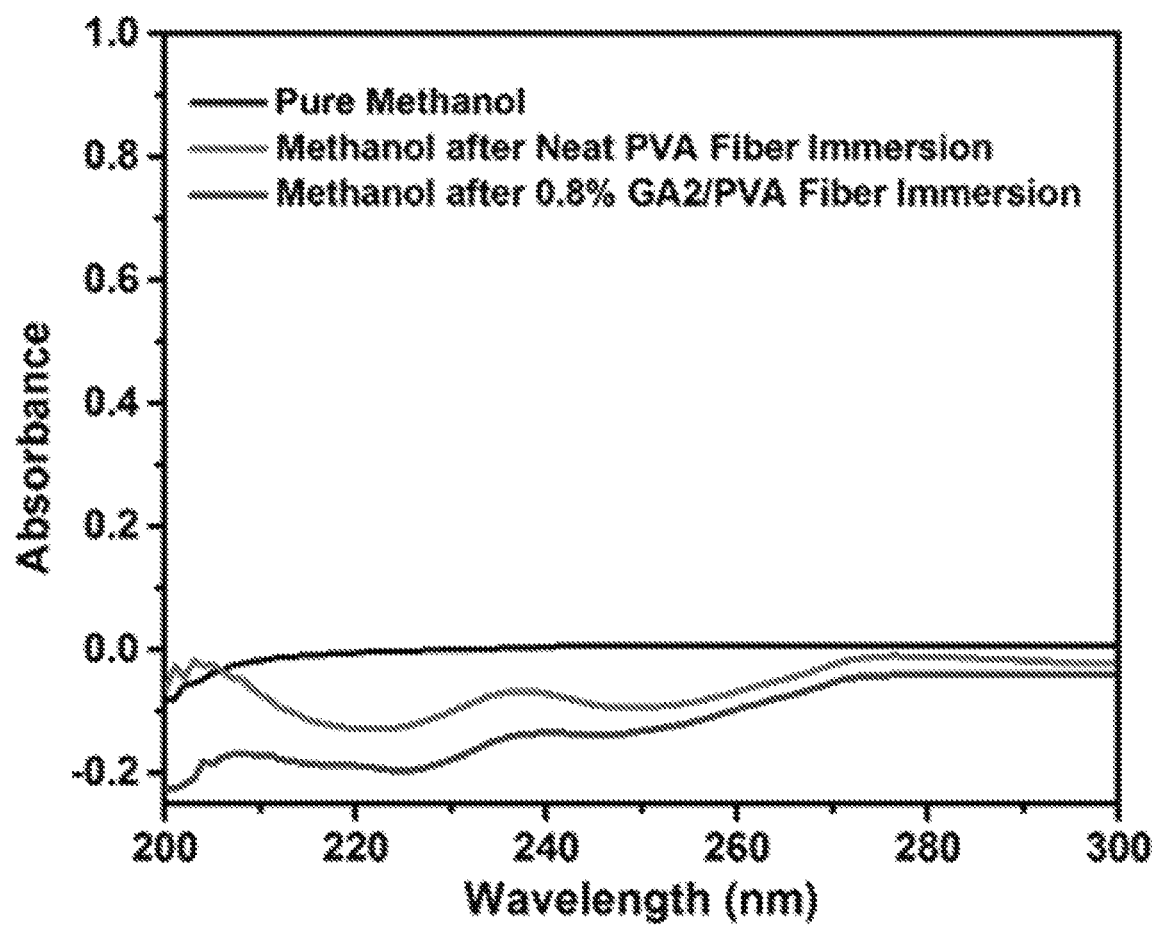
FIG. 15 is a plot showing UV-vis spectra of pure methanol, methanol after containing neat PVA fibers, and methanol after containing GA/PVA fiber at 0.8% GA2.

Pure methanol, diluted lignin solutions and methanol solutions that once contained fiber were analyzed by Agilent Technologies Cary 300 ultraviolet visible (UV-vis) Spectrophotometer. Background spectra are shown in FIG. 15. Three replicates were scanned in the range of 200-300 nm at scan rate 600 nm/min. Lignin's aromatic groups have maximum absorbance at wavelength λ=207 nm. A linear calibration curve (Equation 7 by OriginPro 8) for lignin concentration at a measured absorbance of 207 nm was used to quantify lignin diffused from fiber and into methanol. In Equation 7. Y refers to the absorbance at 207 nm, and X is lignin concentration in methanol. The coefficient of fit was $R^2$=0.97.

$$Y = 9.8X - 0.07 \quad \text{(Equation 7)}$$

Water Dissolution:

The water dissolution study was used to investigate the water resistance of composite fibers. 3 mg of modfied PVA fiber-designated as (lignin to PVA)/(GA2 to PVA) weight ratio of 0/0, 0/0.8, 5/0, 5/0.8, 30/0 and 30/0.8-were placed in 20 mL vials of water. Vials were gradually heated from 25 to 85° C. on a hot plate. LEXT OSL4000 3D measuring laser Confocal Microscope was used to image fiber post water immersion.

Results & Discussion

Anti-Plasticization Behavior of Glucarate within Gel-Spun PVA Fibers

Melting of GA/PVA Gels:

Additives can affect the structure of crystalline polymer, which is evidenced by changes in melting temperature. Gel structure comprises semi-crystalline junctions that stabilize an imperfect, three-dimensional network. Thus, additives are also expected to affect PVA gel melting temperatures.

Figure 2:
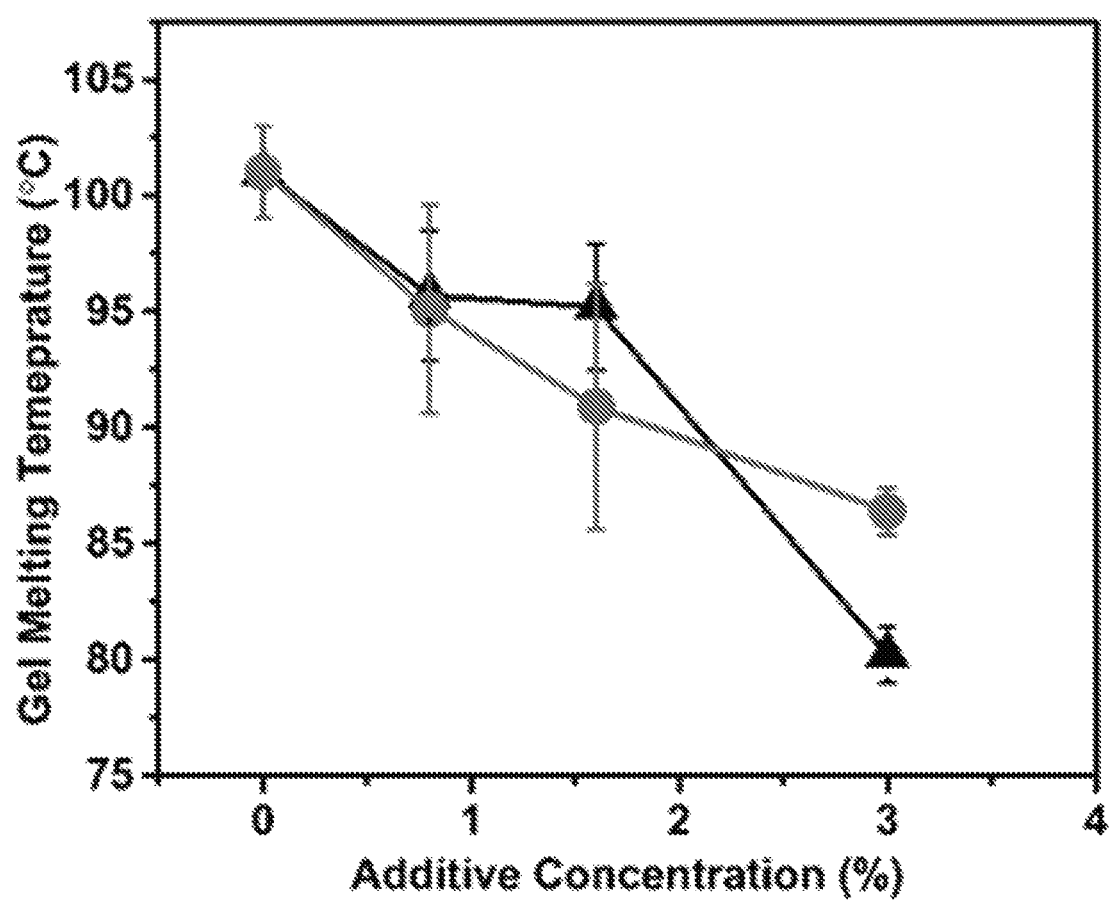
FIG. 2 is a plot showing the gel melting point of a glucarate salt referred to as glucarate salt 1 (GA1) (▲) and a glucarate salt referred to as glucarate salt 2 (GA2) (•) in polyvinyl alcohol (PVA) gels.
Figure 3:
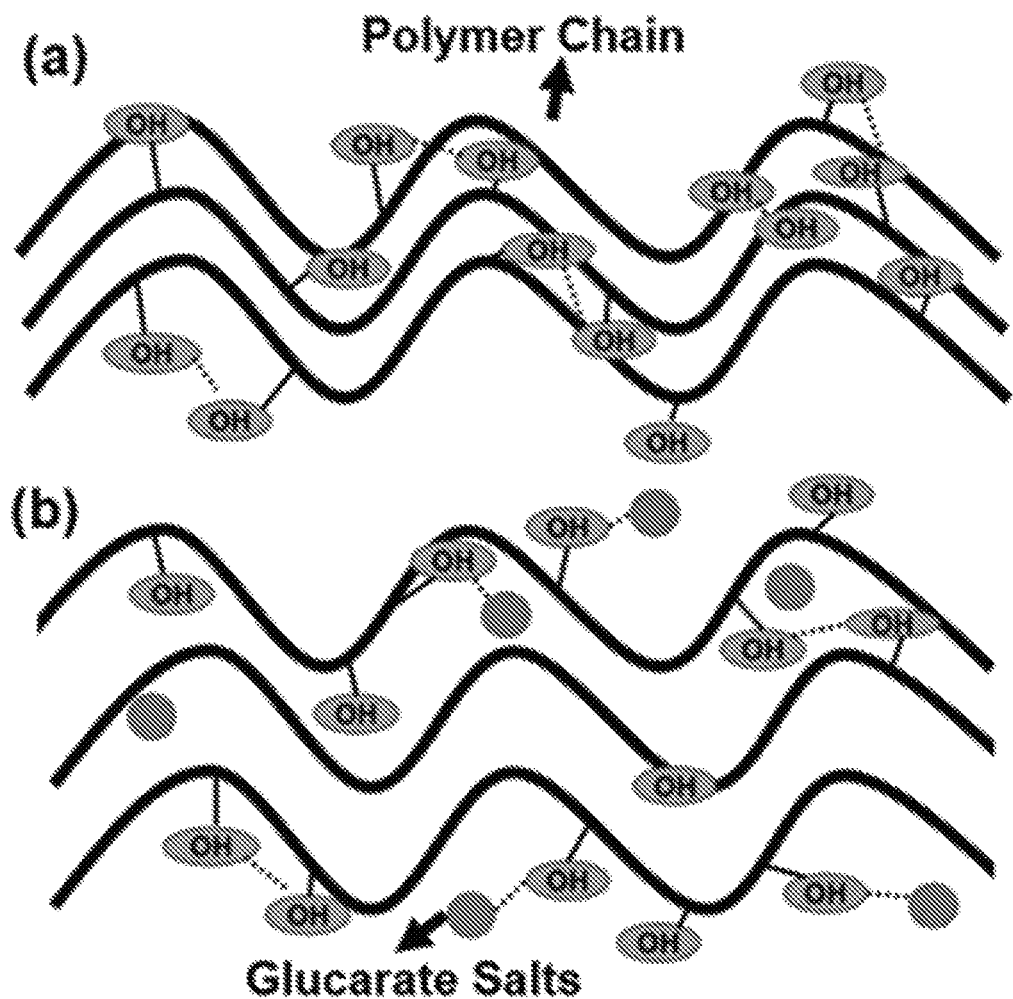
FIG. 3 is an illustration of how glucarate is hypothesized to interact with crystalline PVA domains (a): without glucarate salt and (b): with glucarate salt.

The effect of glucarate salts on gel melting temperature and PVA gel structure are shown in FIG. 2 & FIG. 3, respectively. By adding 0-3% GA1, the gel melting temperature of PVA gels decreased from 101 to 72° C. Likewise, 0-3% GA2 decreased the PVA gel melting temperature from 101 to 86° C. The reduction in gel melting temperature with glucarate salts implies the presence of glucarate salts within the semi-crystalline, polymer-rich domains of PVA gels. As a small molecule, glucarate salt is assumed to disrupt hydrogen bonding among PVA chains; thereby decreasing the gel melting temperature of PVA gels. At 3% glucarate, the mixed salt form seems to disrupt crystalline gel more than the monoammonium salt form. This change in gel structure and melting can subsequently influence parameters for fiber drawing, as discussed in the following section.

Effect of Glucarate on PVA Fiber Drawing Parameters:

The effect of glucarate on the drawing process was summarized in Table 4. By adding GA1, the as-spun draw ratio of gel-fibers increased, suggesting greater flexibility among polymer chains. At 3% GA1, gel-fiber was not drawable at temperatures higher than 60° C. Thus, cold drawing was employed to initially draw gel-fiber and to align polymer chains prior to thermal drawing. PVA modified by GA1 resulted in higher Stage 1-4 draw ratios than obtained for neat PVA fibers. The total draw ratio of GA1/PVA, having up to 1.6% GA1, increased from 21 to 60×. At 3% GA1, total draw ratio was only 37×. The glucarate modified PVA fibers (28-35 µm in diameter) were finer than neat PVA fibers (52 µm).

At 0.8-3% GA2, PVA fibers had higher as-spun draw ratios than neat PVA fibers, as also observed for GA1. In contrast to as-spun gel-fiber having 3% GA1, gel-fiber having 3% GA2 were initially drawn at 95° C.; cold-drawing was not necessary. Stage 1 drawing of 1.6-3% GA2 gel-fibers were 5° C. lower than the drawing of neat PVA. However, this is not the case for 1.6-3% GA1 fibers. FIG. 2 showed 1.6% GA2 fibers had lower melting temperature than that of 1.6% GA1 fibers. At 3%, GA1/PVA gels had much lower melting temperature compared to GA2/PVA gels. The cold draw of 3% GA1 assisted polymer chain alignment/packing and increased its Stage 1 draw temperature to 115° C. The total draw ratio of 0-1.6% GA2 fibers increased from 21 to 76×, and it decreased to 61× at 3% GA2. GA2/PVA fibers were finer fibers (28 and 29 µm) compared to neat PVA fibers (52 µm).

The processing temperatures of GA1/PVA or GA2/PVA fibers from Stage 2-3 were higher than temperatures used for neat PVA. Higher as-spun and Stage 1 draw ratios from glucarate modified PVA fibers enabled higher degrees of polymer alignment and packing. This led to GA/PVA fibers' high Stage 2-3 drawing temperatures, at which polymers were heated and further stretched.

In summary, glucarate in gel-spun PVA greatly influenced the thermal properties of gel-fibers by decreasing their melting temperatures. In contrast to the tight packing of chains within the crystalline phase of neat PVA gel-fibers. GA/PVA gel-fibers are hypothesized to have glucarate intercalated between the chains of crystalline polymer (as depicted in FIG. 3). The presence of glucarate within gel-fiber ultimately increased the molecular mobility of as-spun drawn fiber. Gel-fiber melting temperature mildly influenced fiber draw temperature. At GA2≥1.6%, Stage 1 drawing occurred at 95° C. instead of 100° C. for neat PVA as-spun gel-fiber.

In comparison to neat PVA fibers, the total draw ratio of GA/PVA fiber was higher than for neat PVA fibers. Glucarate enhanced chain mobility with thermal drawing at increasingly higher temperatures. The integration of glucarate within crystalline PVA is hypothesized to influence the crystalline relaxation temperature of PVA, which lends PVA mobile at increasingly higher temperatures. The sequential drawing of PVA gradually increases PVA's crystalline relaxation temperature. The resulting GA/PVA fibers were generally finer than neat PVA fibers after drawing due to higher values of total draw ratio (Table 5).

TABLE 5

Drawing Parameters for Gel-Spun Glucarate/PVA Fibers

| | | Glucaric Acid Type | | | | | |
|---|---|---|---|---|---|---|---|
| | | GA1 | | | GA2 | | |
| | | Additive Concentration | | | | | |
| | | 0.0% | 0.8% | 1.6% | 3.0% | 0.8% | 1.6% | 3.0% |
| As-spun Draw Ratio (DR) | | 2.5 | 3.9 | 3.8 | 3.4 | 3.3 | 4.9 | 4.9 |
| Cold Draw DR | | — | — | — | 2.1 | — | — | — |
| Stage 1 Draw-ing | Temperature (° C.) | 100 | 100 | 100 | 115 | 100 | 95 | 95 |
| | DR | 4.2 | 5.1 | 4.9 | 2.6 | 5.0 | 4.9 | 4.6 |
| Stage 2 Draw-ing | Temperature (° C.) | 140 | 150 | 150 | 170 | 185 | 185 | 185 |
| | DR | 1.4 | 1.8 | 1.9 | 1.4 | 1.4 | 1.5 | 1.6 |
| Stage 3 Draw-ing | Temperature (° C.) | 180 | 200 | 200 | 190 | 200 | 200 | 200 |
| | DR | 1.3 | 1.3 | 1.3 | 1.3 | 1.5 | 1.7 | 1.4 |
| Stage 4 Draw-ing | Temperature (° C.) | 195 | 210 | 215 | 200 | 210 | 210 | 210 |
| | DR | 1.1 | 1.2 | 1.3 | 1.1 | 1.1 | 1.2 | 1.2 |
| Total DR[a] | | 21 | 56 | 60 | 37 | 38 | 73 | 61 |
| Effective diameter (µm) | | 52 | 35 | 28 | 35 | 28 | 29 | 28 |
| Linear Density (dtex) | | 20 | 12 | 8 | 13 | 8 | 9 | 9 |

"—": Not Applicable: fibers were directly drawn in hot oil bath at high temperature
[a]Total DR: Cumulative draw ratio from as-spun DR, cold drawing and thermally drawing fiber (Stage 1-4)

Figure 4:
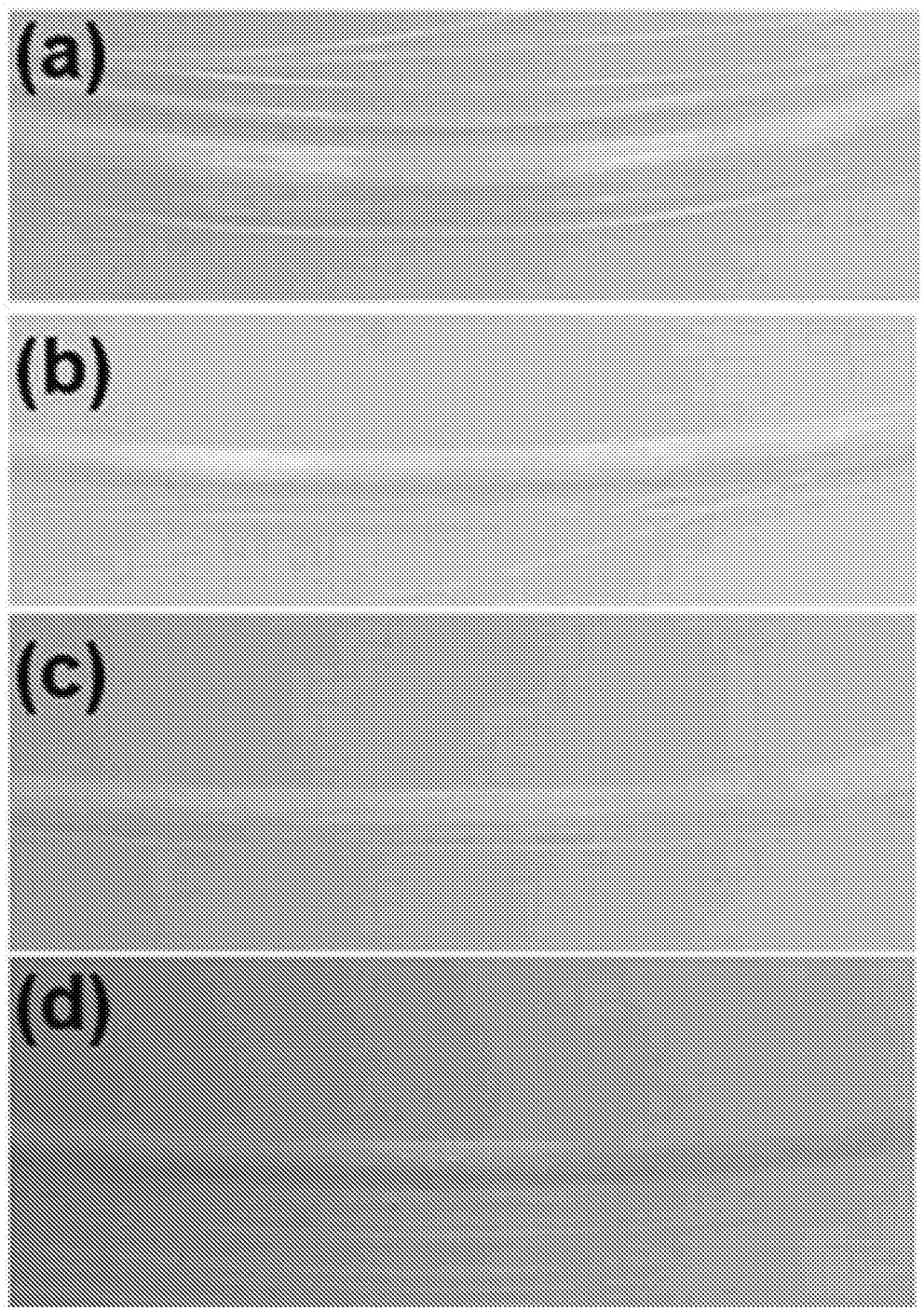
FIG. 4 is a series of images showing (a) 0.0% (b) 0.8% (c) 1.6% and (d) 3% GA2 among GA2/PVA fully-drawn fibers.
Figure 5A:
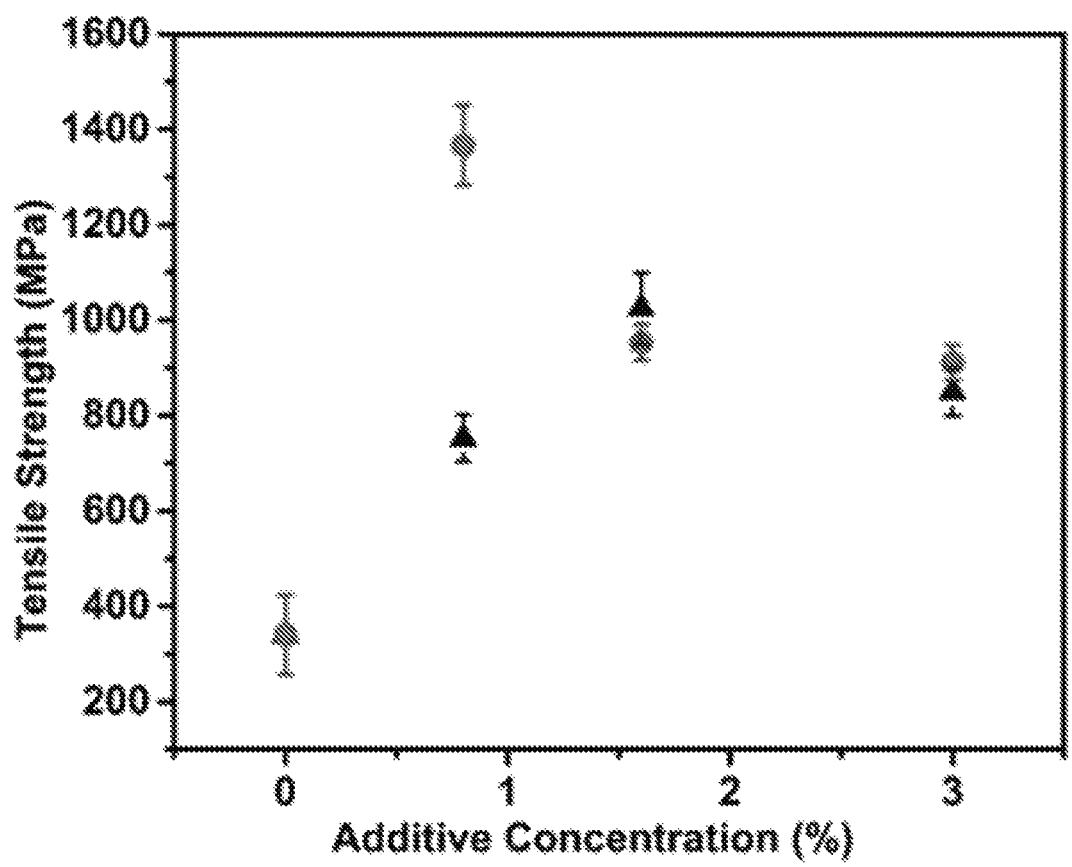
FIG. 5A-D are plots showing mechanical properties of GA/PVA fibers.
Figure 5B:
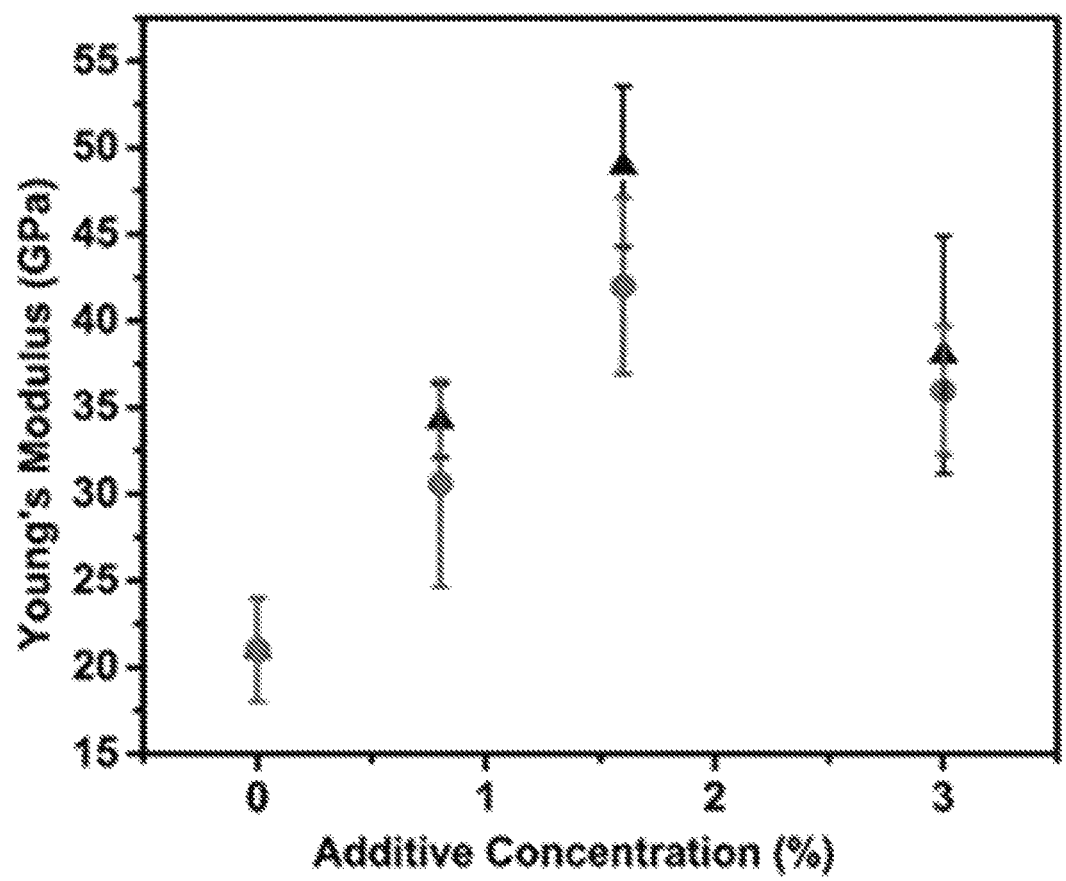
Figure 5C:
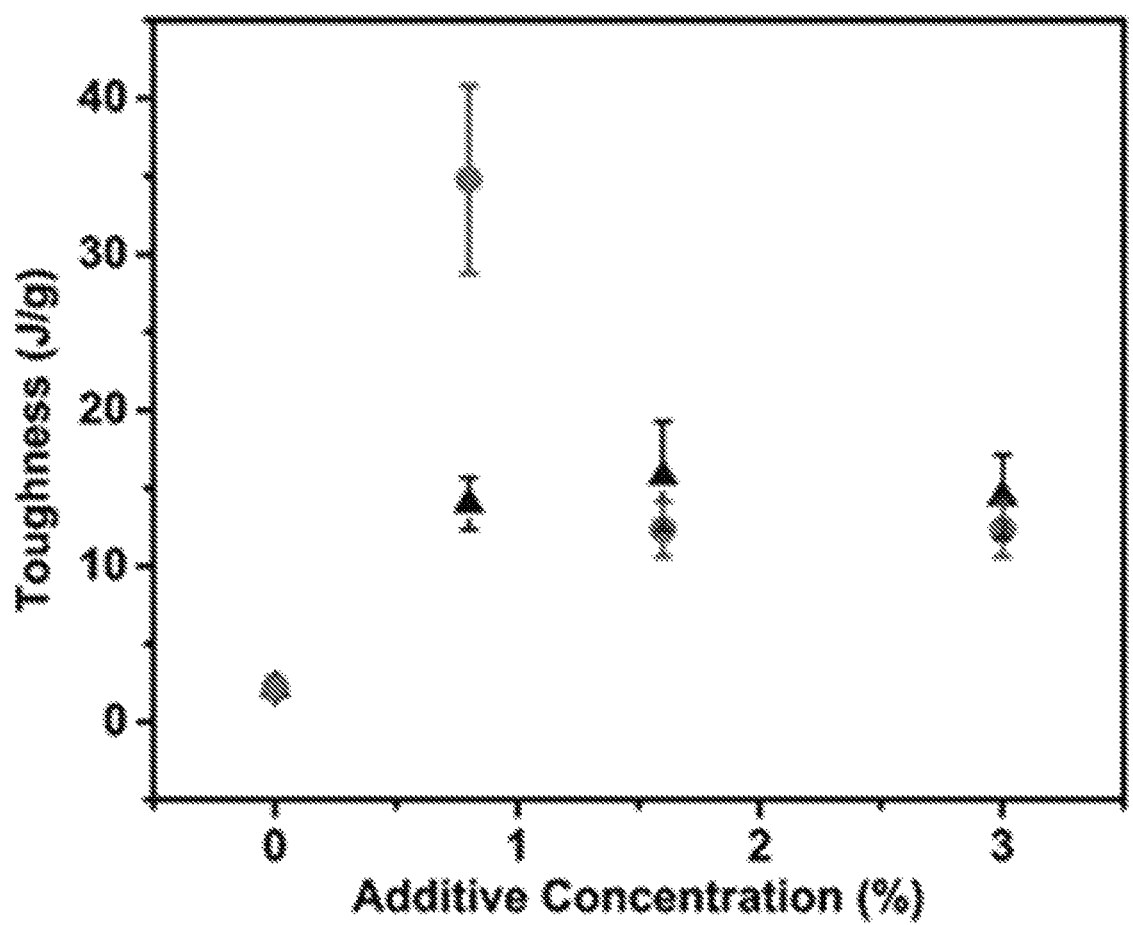
Figure 5D:
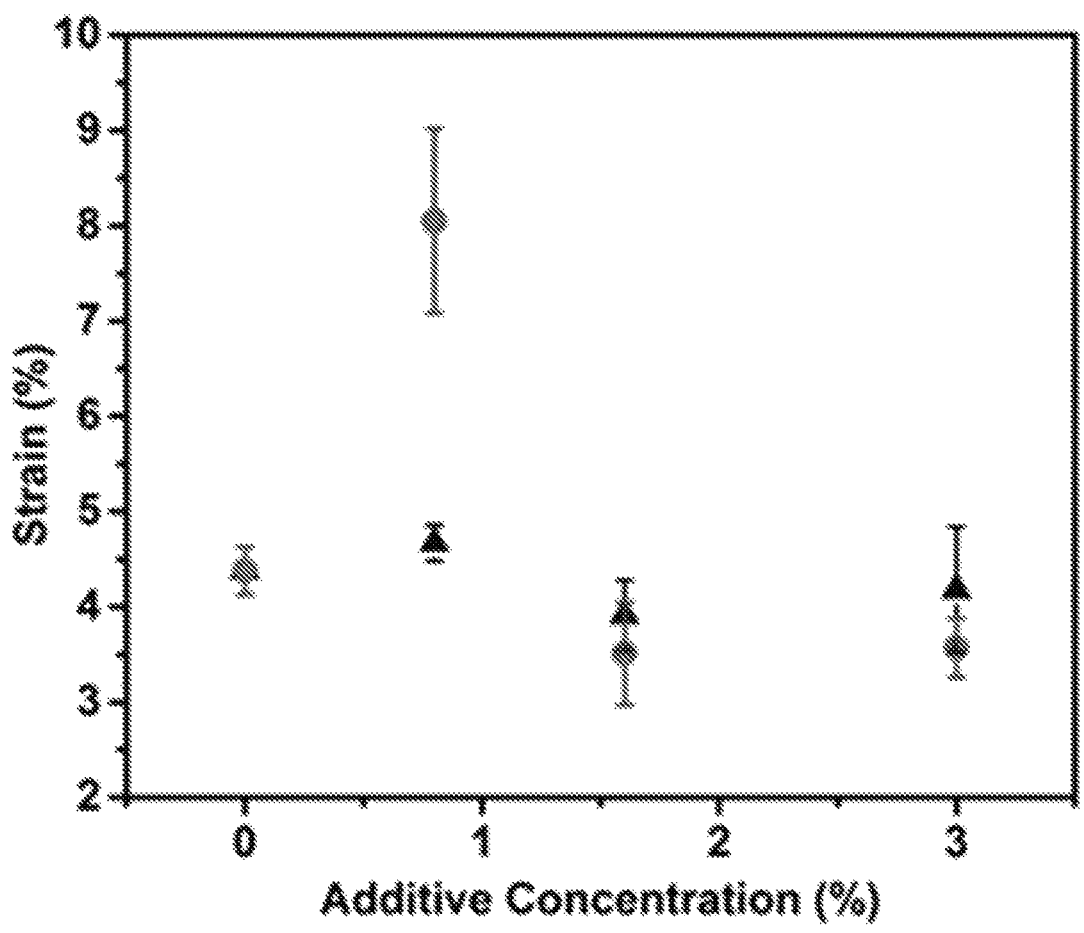
Figure 16A:
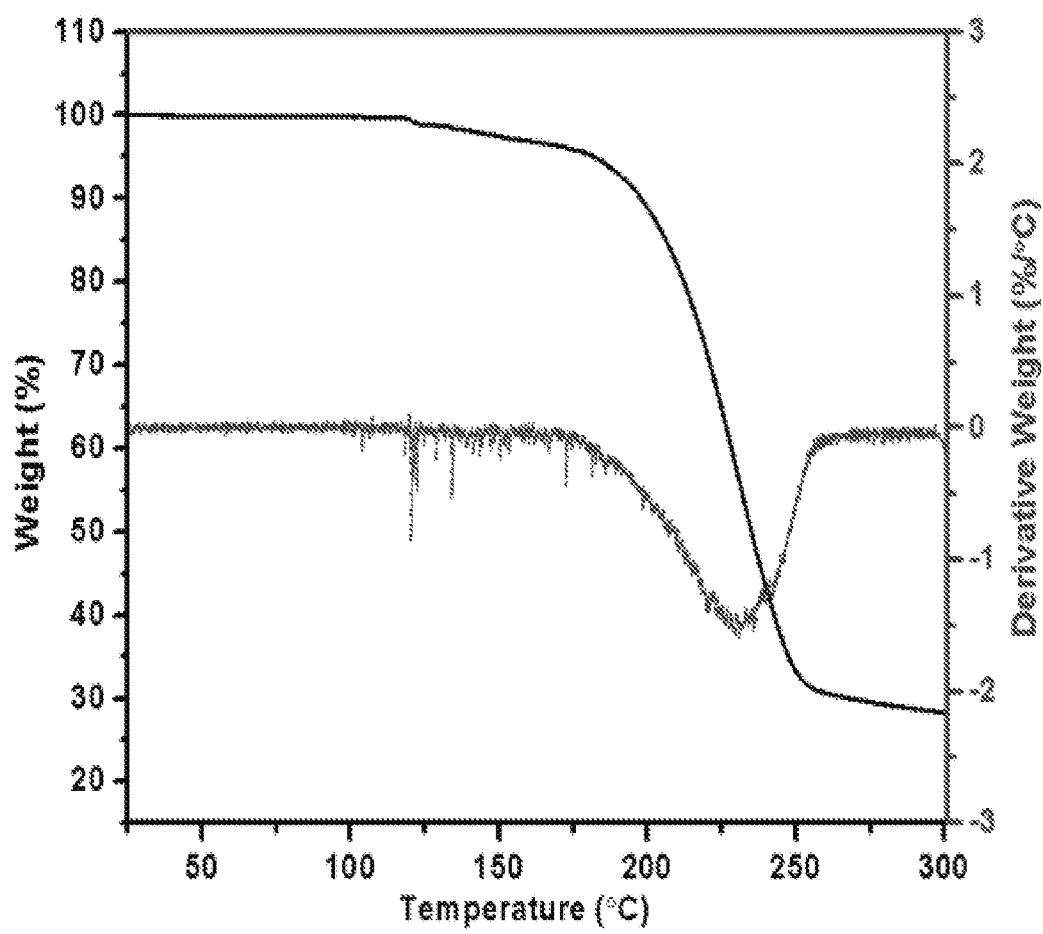
FIG. 16A-B are plots showing thermogravimetric analysis (TGA) of FIG. 16A: GA1
Figure 16B:
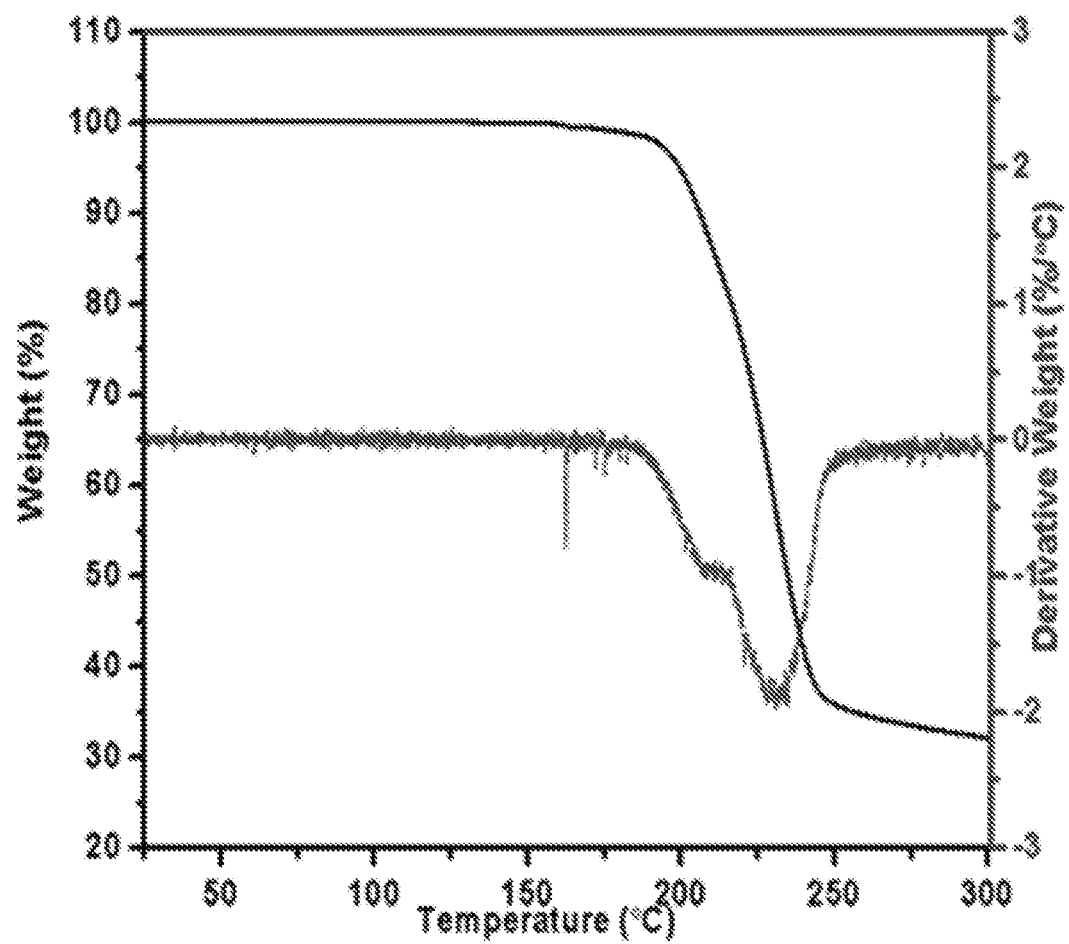

In Observation of GA/PVA Fibers:

Several fibers appeared darker after multiple stages of thermal drawing. At GA2≥1.6%, FIG. 4 shows changes in fiber color. The thermal degradation of glucarate was investigated by TGA to help understand these changes in appearance. The onset of glucarate salt degradation was 200° C. for GA1 and 210° C. for GA2 (FIG. 16A and FIG. 16B). Stage 3 and 4 drawing temperatures coincided with this range of thermal processing (200-215° C. in Table 5). As fiber was drawn for 5-8 s in silicone oil, dehydration of glucarate hydroxyl groups (—OH) resulted in carbon-carbon double bonds (C═C) along its backbone. IR spectra had shown absorbance due to double bonds at 1000 $cm^{-1}$. The additive degradation did indeed cause the browning of GA/PVA fibers, having GA≥1.6%. Since glucarate salts affected the melting of PVA gels and the thermal drawing of gel-fiber, the resulting mechanical performance of thermally-drawn fibers was studied.

Mechanical Properties of Gel-Spun GA/PVA Fibers:

Neat PVA fibers had tensile strength of 0.34 GPa, Young's modulus 21 GPa, and toughness 2 J/g, but fibers of 0.8-3% glucarate salt were stronger than neat PVA fibers. The strongest GA1/PVA fiber was 1.1 GPa tensile strength, 49 GPa Young's modulus and 16 J/g toughness. Among GA2/PVA fibers, the highest modulus value was 42 GPa obtained at 1.6% GA2, and the highest tensile strength was 1.4 GPa at 0.8% GA2, and with 0.8% GA2 the toughness was 35 J/g-which is comparable to Kevlar (at least 33 J/g). Other fibers' strain values were in the range of 3.5-5%; whereas 0.8% GA2 fibers had 8.1% strain. At 1.6% GA2, Young's modulus was 42 GPa. Glucarate salts at up to 3% additive yielded mechanical properties that were greater than commercially available, high strength Kuralon™ PVA staple fiber that is 0.88 GPa in tensile strength and 23 GPa in Young's modulus.

Glucarate salts enhanced the mechanical performance of PVA due to anti-plasticization, which ultimately increased fiber draw ratios and fineness. On the other hand, fibers with glucarate content higher than 1.6% showed decreased mechanical properties than fiber with low glucarate content (>0%). Glucarate degradation among fibers having GA≥1.6% was visually observed, as shown in FIG. 4. To better understand the effect of glucarate anti-plasticization on the molecular structure and anisotropy of fibers, spectroscopy was employed.

Figure 6:
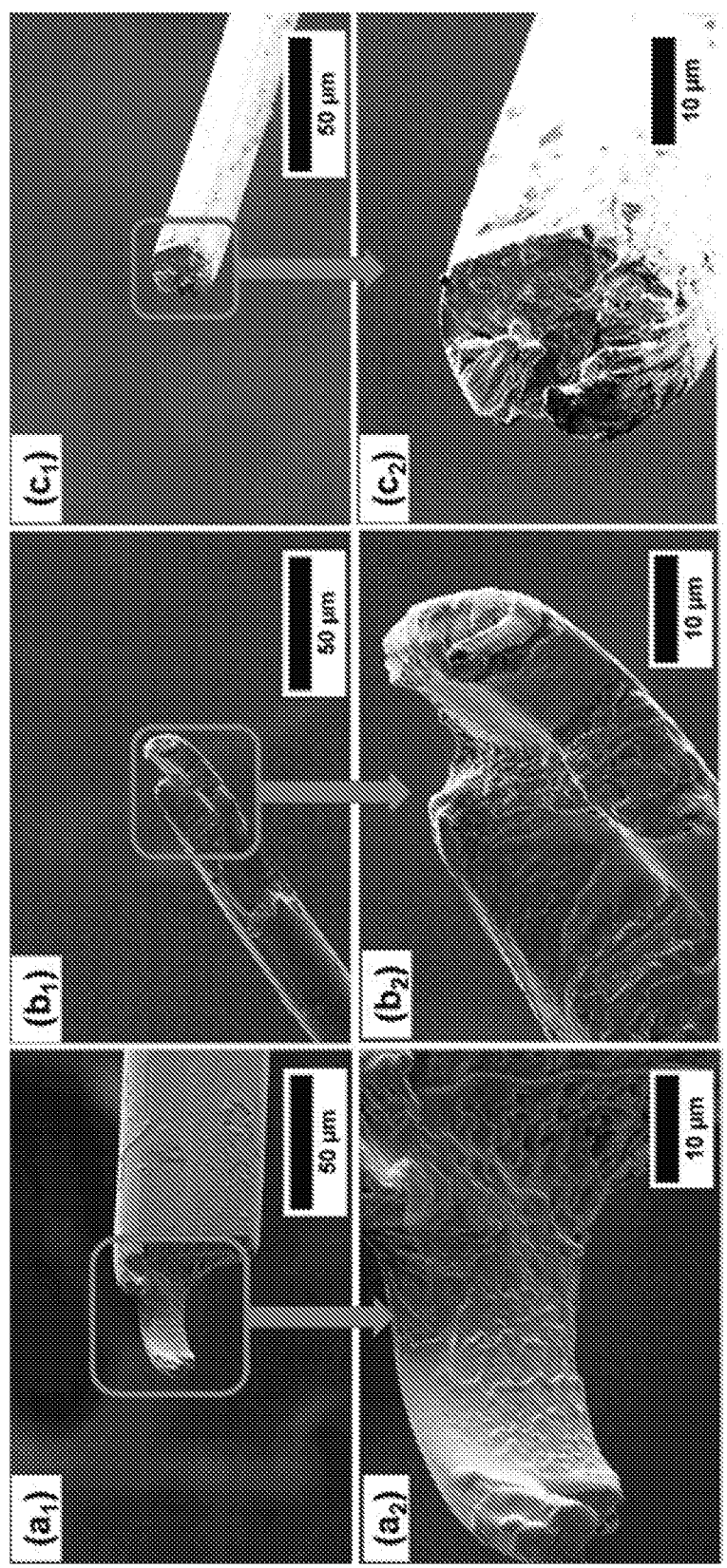
FIG. 6 is a series of images showing fiber fracture tips of (a) neat PVA, and PVA with glucarate at (b) 0.8% GA2 and (c) 1.6% GA1 imaged with scanning electron microscopy (SEM) at $x_1$: low resolution and $x_2$: high resolution.

The fracture tips of neat PVA and glucarate fibers (at 0% glucarate, 1.6% GA1/PVA, and 0.8% GA2/PVA having the highest mechanical properties) were shown in FIG. 6. All fibers exhibited ductile fracture. Among high strength, high modulus fibers that are strengthened with carbon nanotubes (CNTs) addition of filler resulted in PVA fibrils, which are indicative of highly aligned polymer along the fiber axis. However, no obvious fibrillar microstructure was observed among these GA/PVA fibers. This further suggests glucarate salts behave more like plasticizing additives than crystalline fillers that template crystallization.

Effect of Glucarate on PVA Fiber Structure:

Since GA2/PVA fibers yielded the highest values of mechanical performance, the effect of glucarate content on PVA crystallization was investigated by IR spectroscopy. As shown in FIG. 7B, neat PVA fibers had a single peak at 1144 $cm^{-1}$ for crystalline polymer. In contrast to neat PVA fibers, fibers at GA2≥0.8% had a peak at 1130 $cm^{-1}$ shouldering the 1144 $cm^{-1}$ peak. IR spectra of isotactic PVA have shown a small shoulder at 1160 $cm^{-1}$ along the more dominate 1145 $cm^{-1}$ peak to indicate two conformations of crystalline polymer. In this study, atactic PVA was spun. Thus, the formation of 1130 $cm^{-1}$ was the result of glucaric acid crystallized within PVA; whereas the crystallization of pure PVA occurred at 1144 $cm^{-1}$. It has been reported the computational modeling of PVA crystals after addition of potassium iodine. In contrast to pure PVA crystals, iodine salts disrupted PVA polymer chain interactions and expanded the unit cell crystal. The 1130 $cm^{-1}$ peak is indicative of the expanded PVA, crystalline conformation with the addition of anti-plasticizer-glucarate. This obvious change in crystalline form supports our use of IR spectroscopy opposed to WAXD to analyze PVA crystallization in the presence of glucarate. The preference for IR analysis is supported with further discussion of lignin/GA/PVA fibers. Indices account for both crystalline forms and fiber crystallinity are reported in Table 6. By adding 0-3% GA2, the crystallinity indices increased from 2.1 to 2.7, suggesting an increase in PVA's crystallinity with anti-plasticizer overall.

Figure 7A:
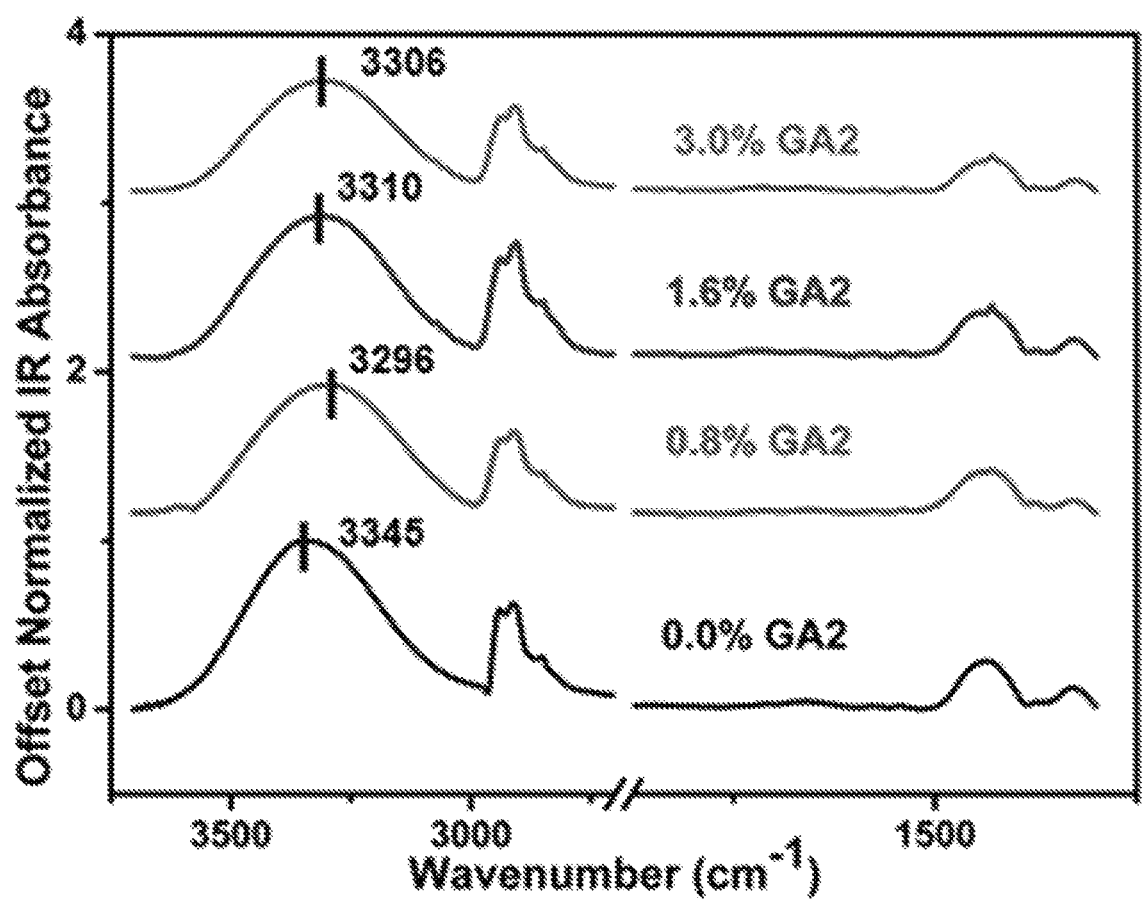
FIG. 7A-B are plots showing IR absorbance spectra of GA2/PVA fibers at 0-3% GA2.
Figure 7B:
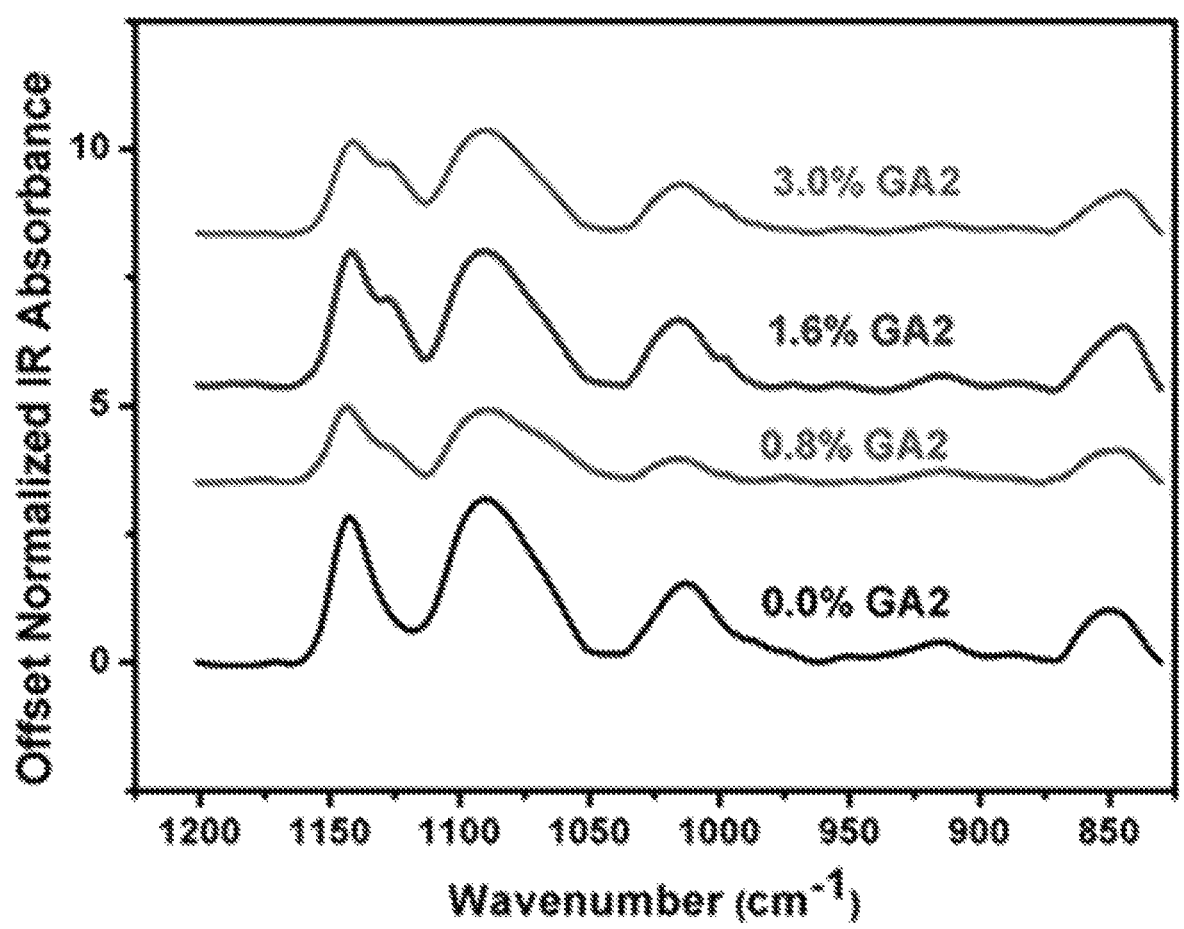

To further confirm the anti-plasticizing behavior of glucarate salts, intermolecular interactions between GA2 and PVA was analyzed by IR spectroscopy (FIG. 7A). Hydrogen bonding among PVA hydroxyl groups was represented by a peak centered at 3345 $cm^{-1}$ for neat PVA fiber. With the addition of glucarate, the band shifted toward lower frequencies, indicating intermolecular hydrogen bonding between PVA and glucarate. At 0.8% GA2, the strongest interaction between hydrogen bonds were represented by an absorbance peak at 3296 $cm^{-1}$. At higher GA2 content, the —OH peak shifted to 3310 $cm^{-1}$ for 1.6% GA2 and 3306 $cm^{-1}$ for 3% GA2. In general, IR spectra confirmed that glucarate salt disrupted PVA cohesion. As a result, GA/PVA fibers were more drawable at elevated temperatures of drawing (Table 5). Fully-drawn fibers were drawn towards higher total draw ratios due to anti-plasticization. Strong additive/polymer adhesion and crystallinity among drawn fibers contributed to the high mechanical performance of fibers.

Table 6 lists the normalized height of the hydrogen bonding peak (3345≥$I_{(OH)}$≥3296, from FIG. 7A). At low glucarate content (GA2≤1.6%), $I_{(OH)}$ values from fibers were similar. But, the value of $I_{(OH)}$ decreased with additional GA2, as GA disrupted inter- and intramolecular bonding between long chain PVA. Lower $I_{(OH)}$ values were observed at 3.0% GA2 content in fiber. The dehydration of intercalating glucarate (as evidenced by molecular degradation and the browning of fibers in FIG. 4) also caused the reduction in hydrogen bonding.

The following occurrences are additional indicators of glucarate degradation. IR spectra of fibers containing GA≥1.6% had a sharp peak (at 1430 $cm^{-1}$ for —$CH_3$ groups) that was imposed upon the peak at 1445 $cm^{-1}$—$CH_2$— groups (FIG. 7A). A small peak at ~1000 $cm^{-1}$ (in FIG. 7B that is assigned to the aliphatic bending of —CH═CH—) appeared among fibers containing GA≥1.6%. Crosslinking between degraded additive and polymer can occur, causing the occurrence of a sharp peak (—$CH_3$) at 1430 $cm^{-1}$ in the region representing —$CH_2$. Crosslinking would cause a reduction in the mechanical performance of fibers containing GA≥1.6%.

TABLE 6

IR Absorbance Ratio of $A_{(1144 + 1130)}/A_{854}$ and Normalized Peak Height of $I_{(OH)}$ from Fully Drawn GA2/PVA Fibers

| GA2 Content | $A_{(1144+1130)}/A_{854}$ | $I_{(OH)}$ |
|---|---|---|
| 0.0%* | 2.1 | 1.00 |
| 0.8% | 2.4 | 0.80 |
| 1.6% | 2.6 | 0.83 |
| 3.0% | 2.7 | 0.65 |

*No prominent crystalline peak shown at 1130 $cm^{-1}$, $A_{1144}/A_{854}$ value is used.

Figure 8:
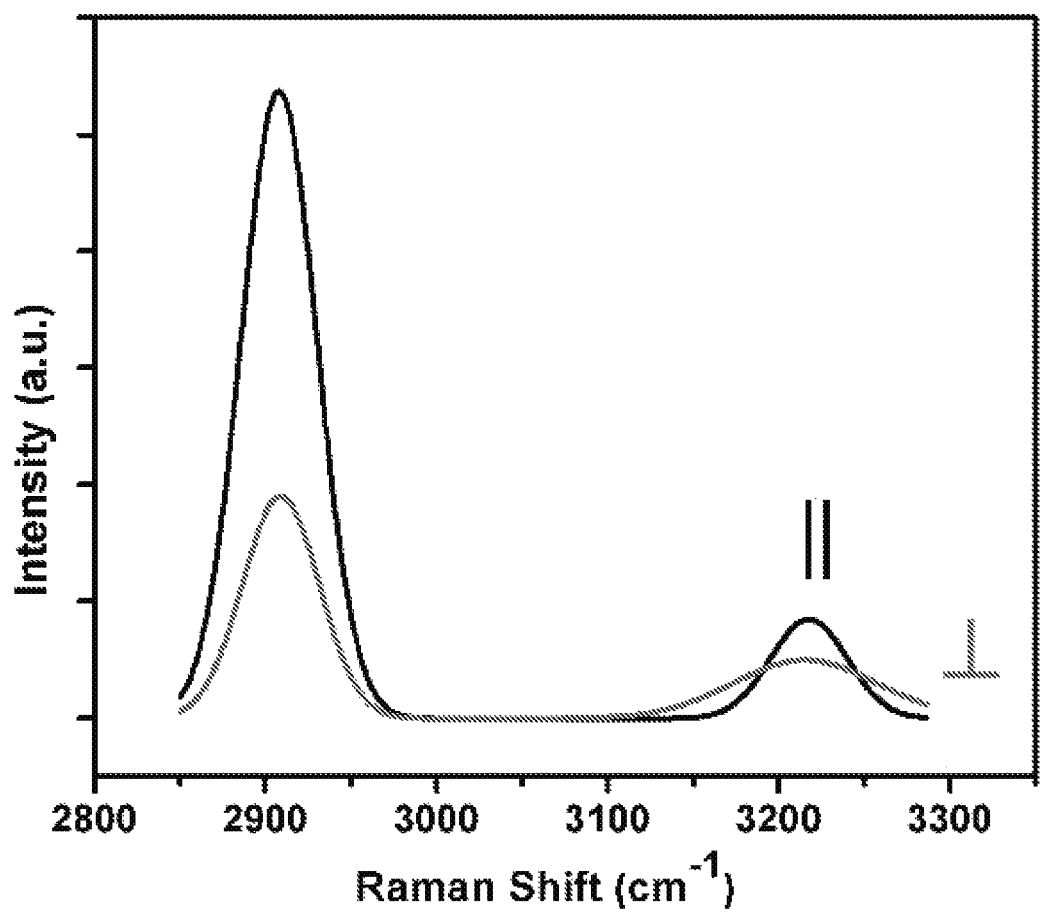
FIG. 8 is a plot showing polarized Raman spectra of 0.8% GA2 fiber parallel (∥ or 0°) and perpendicular (⊥ or 90°) to the fiber axis.

Polarized Raman spectra were used to study PVA chain alignment. Raman anisotropy was measured for the C—H stretching peak at 2910 $cm^{-1}$ and the —OH stretching of PVA at 3210 $cm^{-1}$ peak (FIG. 8) among fibers containing up to 3% GA2 (Table 7). The molecular anisotropy (R), decreased at 3% GA in comparison to neat fiber. R values for —OH stretching followed the same trend as C—H stretching, as GA2 content increased up to 3%. The highest R values for C—H and —OH groups were observed at 0.8% GA2. Parameters increased from $R_{C—H}$=1.6 at 0% GA2 to $R_{C—H}$=2.8 at 0.8% GA2 and from $R_{OH}$=1.1 at 0% GA2 to $R_{OH}$=1.7 at 0.8% GA2. The backbone of PVA chains were oriented towards the fiber axis when 0.8% GA2 was added.

TABLE 7

Orientation Parameters for PVA within Glucarate/PVA Fibers

| GA2 Content | | 0.0% | 0.8% | 1.6% | 3.0% |
|---|---|---|---|---|---|
| Raman anisotropy (R) | PVA (C—H) | 1.6 | 2.8 | 2.5 | 2.1 |
| | PVA (—OH) | 1.1 | 1.7 | 1.2 | 1.1 |

The trend for PVA orientation, among GA2/PVA fibers, agrees well with changes in hydrogen bonding, $I_{(OH)}$ in FIG. 7A. Thus, hydrogen bonding aided the alignment of the PVA's hydroxyl groups and its main chain. As reported in Ford et al, *Macromolecular Chemisty and Physics* 2012, 213 (6), 617-626 (which is incorporated by reference herein in its entirety), the orientation of PVA's crystalline conformation is not the only factor affecting the molecular alignment of its pendant hydroxyl groups. Additives and intermolecular bonding influences molecular alignment within drawn fibers. Better alignment of crystalline PVA and its pendant hydroxyl groups was achieved through hydrogen bonding. The PVA main chain and its hydroxyl group alignment was affected by the incorporation of GA2, because glucarate influenced the crystalline conformation of PVA and hydrogen bonding among PVA chains. Subsequently, the alignment of PVA hydroxyl groups influenced the mechanical performance of fibers (FIG. 5A-FIG. 5D), especially at 0.8% GA2. At 0.8% GA2, PVA hydroxyl groups were most oriented, and fiber tensile strength was the highest value reported (1.4 GPa).

In summary, glucarate salts are effective anti-plasticizers for gel-spun PVA fibers. Although glucarate salts reduced gel melting temperature at higher concentrations, the additives increased fiber draw ratios and the mechanical performance of fully-drawn fibers relative to neat PVA fibers. Polymer crystallinit, intermolecular adhesion, concentration of hydroxyl groups engaged in hydrogen bonding and the orientation of molecular groups within fiber were enhanced by glucarate within PVA fiber. However, at GA≥1.6%, glucarate dehydration reduced hydrogen bonding between molecular chains while also behaving as a non-covalent crosslinker that ultimately lowered the mechanical properties of glucarate fibers.

Effect of Glucarate on Mechanical Performance of Gel-Spun Lignin/PVA Fibers

From the foregoing, 0.8% GA2 fiber had the highest degree of intermolecular adhesion between glucarate and PVA, highest tensile strength, and highest toughness value. Since GA≥1.6% reduced values of mechanical performance, lignin/GA/PVA fibers contained 0.8% GA2 and up to 30% lignin. The mechanical performance, structural properties and moisture resistance of lignin/GA/PVA fibers were analyzed.

Drawing of Lignin/GA2/PVA Fiber:

Table 8 summarizes spinning parameters for lignin/GA2/PVA fibers. In comparison to neat PVA fibers, fiber having 0.8% GA2 and 5% lignin was drawn finer with larger draw ratios. But, the additive GA2 alone led processing towards a higher value of draw ratio and finer fibers. Stage 2-4 drawing temperatures for 5% lignin fibers were lower after adding 0.8% GA2. Although glucarate facilitated PVA chain slippage when lignin was not present, they had little effect on the total draw ratio of 5% lignin-based fibers.

Among 30% lignin fibers, as-spun draw ratio was higher after adding 0.8% GA2 in fiber. During Stage 2-4, the temperature of drawing was lower with 0.8% GA2. The total draw ratio was increased from 25 to 45×. Thus, glucarate enhanced chain mobility in 30% lignin based fiber.

TABLE 8

Drawing Parameters for Gel-Spun Lignin/Glucarate/PVA Fibers

| | | (lignin to PVA)/(GA2 to PVA) ratio | | | | | |
|---|---|---|---|---|---|---|---|
| | | 0/0 | 0/0.8 | 5/0 | 5/0.8 | 30/0 | 30/0.8 |
| As-spun DR | | 2.5 | 3.3 | 2.6 | 2.9 | 1.4 | 2.5 |
| Stage 1 Drawing | Temperature (° C.) | 100 | 100 | 100 | 100 | 100 | 100 |
| | DR | 4.2 | 5.0 | 5.8 | 6.1 | 7.0 | 7.0 |

TABLE 8-continued

Drawing Parameters for Gel-Spun Lignin/Glucarate/PVA Fibers

| | | (lignin to PVA)/(GA2 to PVA) ratio | | | | | |
|---|---|---|---|---|---|---|---|
| | | 0/0 | 0/0.8 | 5/0 | 5/0.8 | 30/0 | 30/0.8 |
| Stage 2 Drawing | Temperature (° C.) | 140 | 185 | 180 | 165 | 190 | 185 |
| | DR | 1.4 | 1.4 | 1.7 | 1.4 | 1.5 | 1.8 |
| Stage 3 Drawing | Temperature (° C.) | 180 | 200 | 210 | 180 | 210 | 200 |
| | DR | 1.3 | 1.5 | 1.3 | 1.3 | 1.4 | 1.3 |
| Stage 4 Drawing | Temperature (° C.) | 195 | 210 | 230 | 200 | 230 | 215 |
| | DR | 1.1 | 1.1 | 1.2 | 1.2 | 1.2 | 1.1 |
| Total DR$^a$ | | 21 | 38 | 40 | 39 | 25 | 45 |
| Effective diameter (μm) | | 52 | 28 | 32 | 34 | 48 | 34 |
| Linear Density (dtex) | | 20 | 8 | 10 | 12 | 23 | 11 |

$^a$Total DR: Cumulative draw ratio from as-spun DR, cold drawing and thermally drawing fiber (Stage 1-4)

Figure 9A:
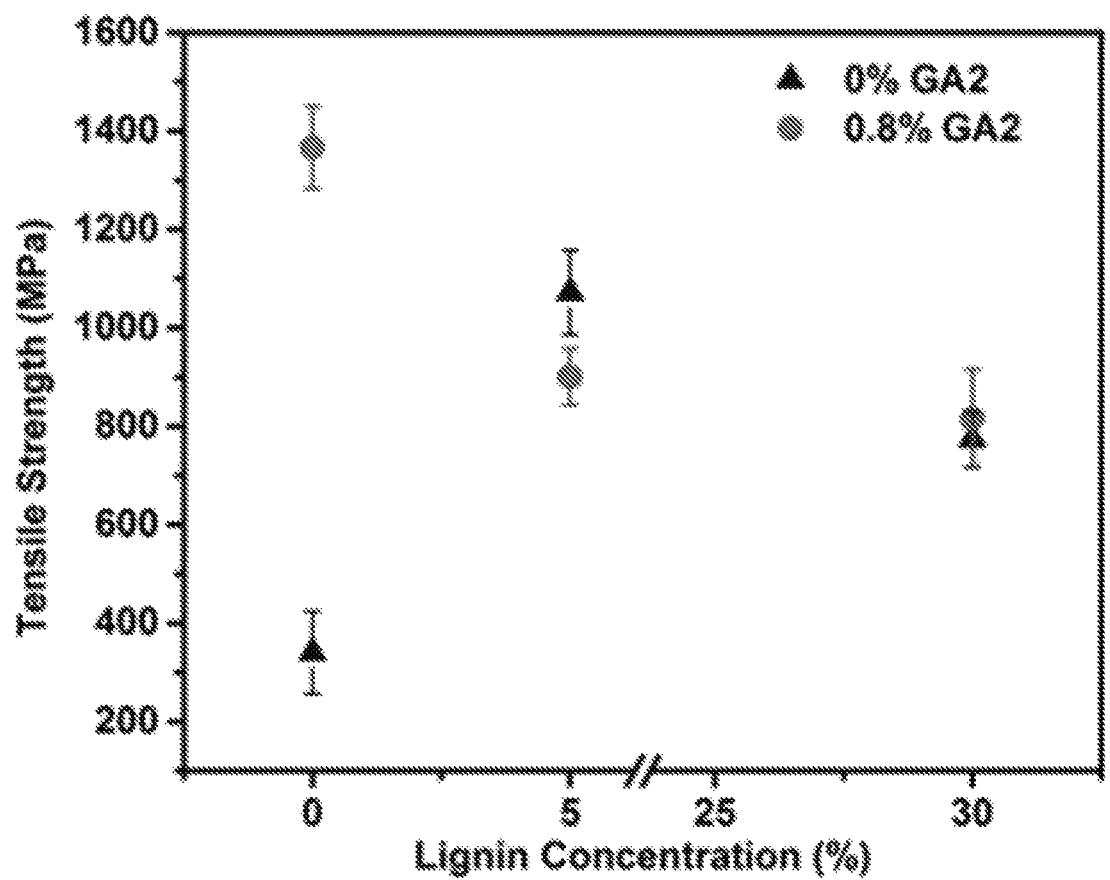
FIG. 9A-C are plots showing mechanical properties of lignin/GA/PVA fibers containing up to 30% lignin and GA2 content at 0% (▲) and 0.8% (•) polymer.
Figure 9B:
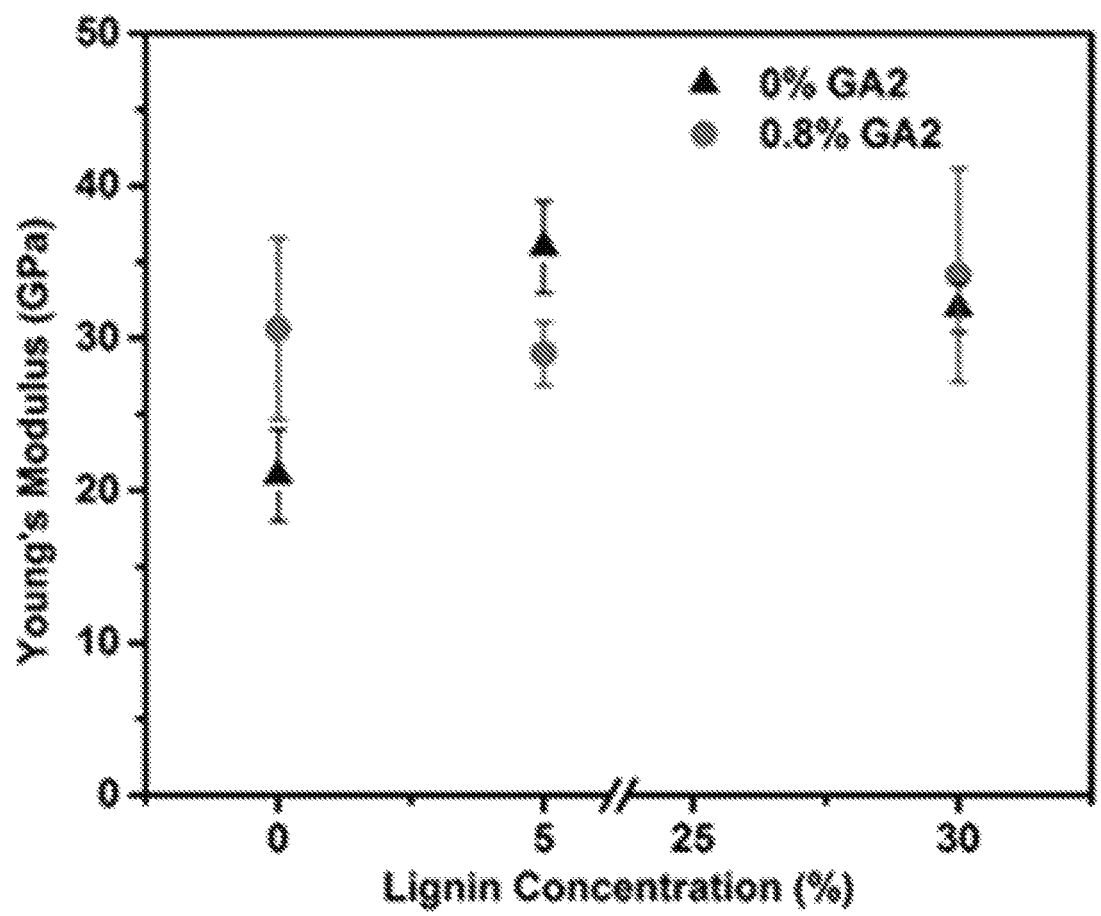
Figure 9C:
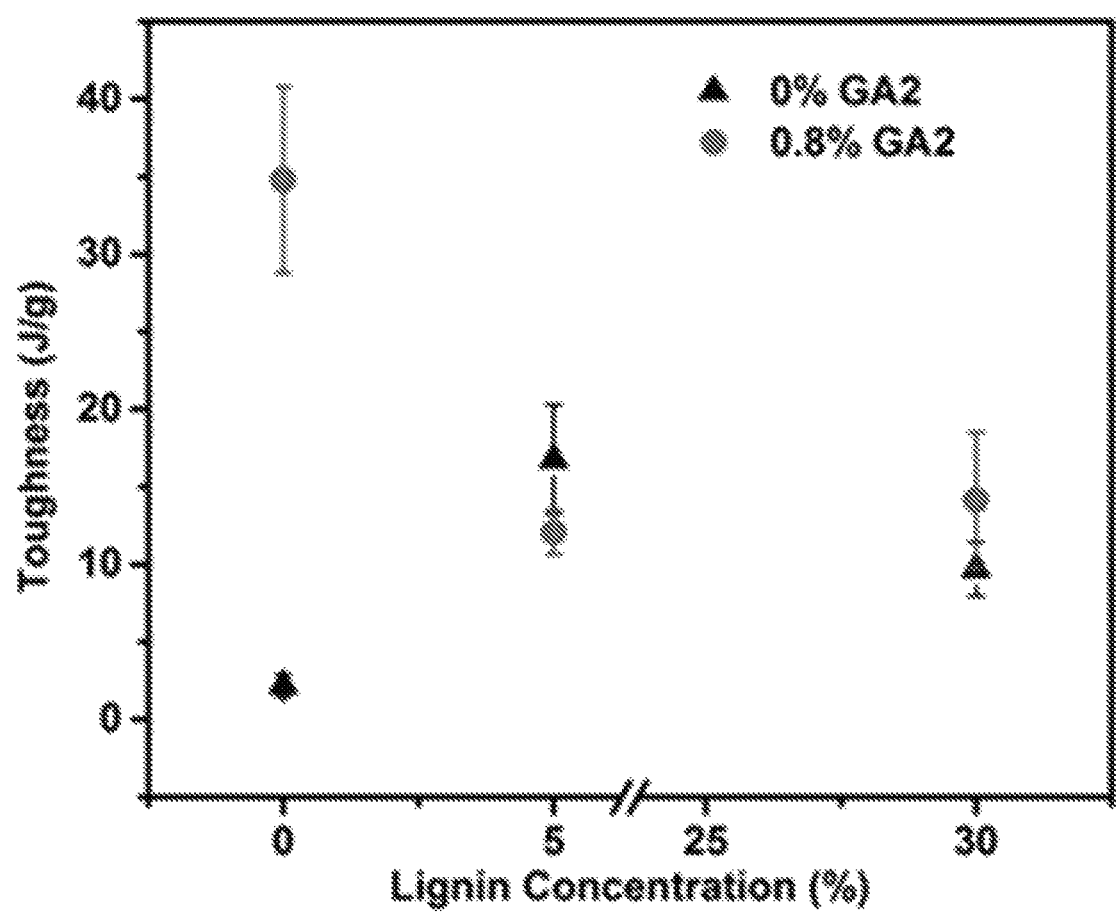

Mechanical Properties of Lignin/GA/PVA Fibers:

The influence of lignin and GA2 on the mechanical performance of PVA fibers is shown in FIG. 9A-FIG. 9C. 5% lignin fibers showed the highest values of mechanical strength: tensile strength 1.1 GPa, Young's Modulus 36 GPa, and toughness 17 J/g. 30% lignin fibers were less strong: tensile strength 0.77 GPa, Young modulus 32 GPa, and toughness 10 J/g. Above >20% lignin, lower fiber crystallinity, random lignin alignment and lignin aggregates can occur in the fiber structure.

At each lignin concentration, the effect of 0.8% GA2 on mechanical performance was measured. At 5% lignin, the slight decreases in tensile strength and toughness were observed at 0.8% GA2. The addition of 0.8% GA2 to 5% lignin fibers did not further increase fiber draw ratio. Although 30% lignin fiber's total draw ratio was increased from 25 to 45×, the tensile strength and modulus were not affected by 0.8% GA2 (tensile strength was 0.82 GPa, Young's Modulus was 34 GPa. and toughness was 14 J/g). Since the compatibility of lignin and glucarate may have affected PVA fiber properties, fiber macrostructure was studied.

Figure 10A:
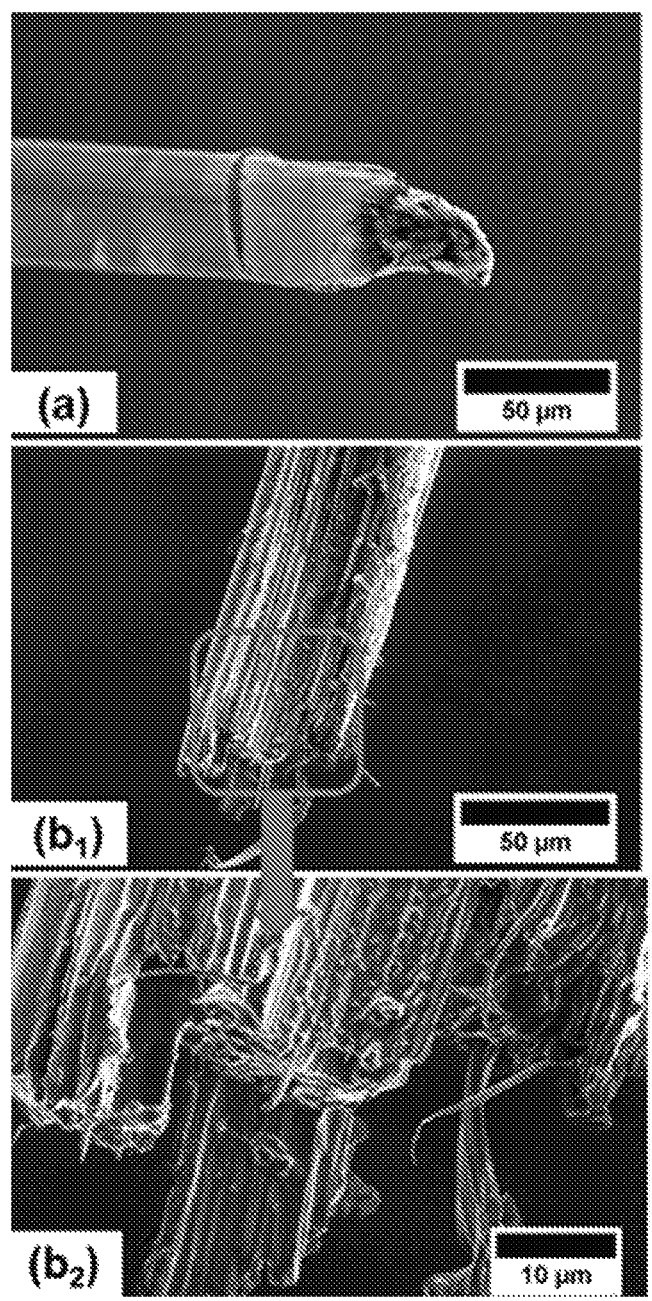
FIG. 10A-B are a series of images showing fracture tips of lignin/PVA fibers.
Figure 10B:
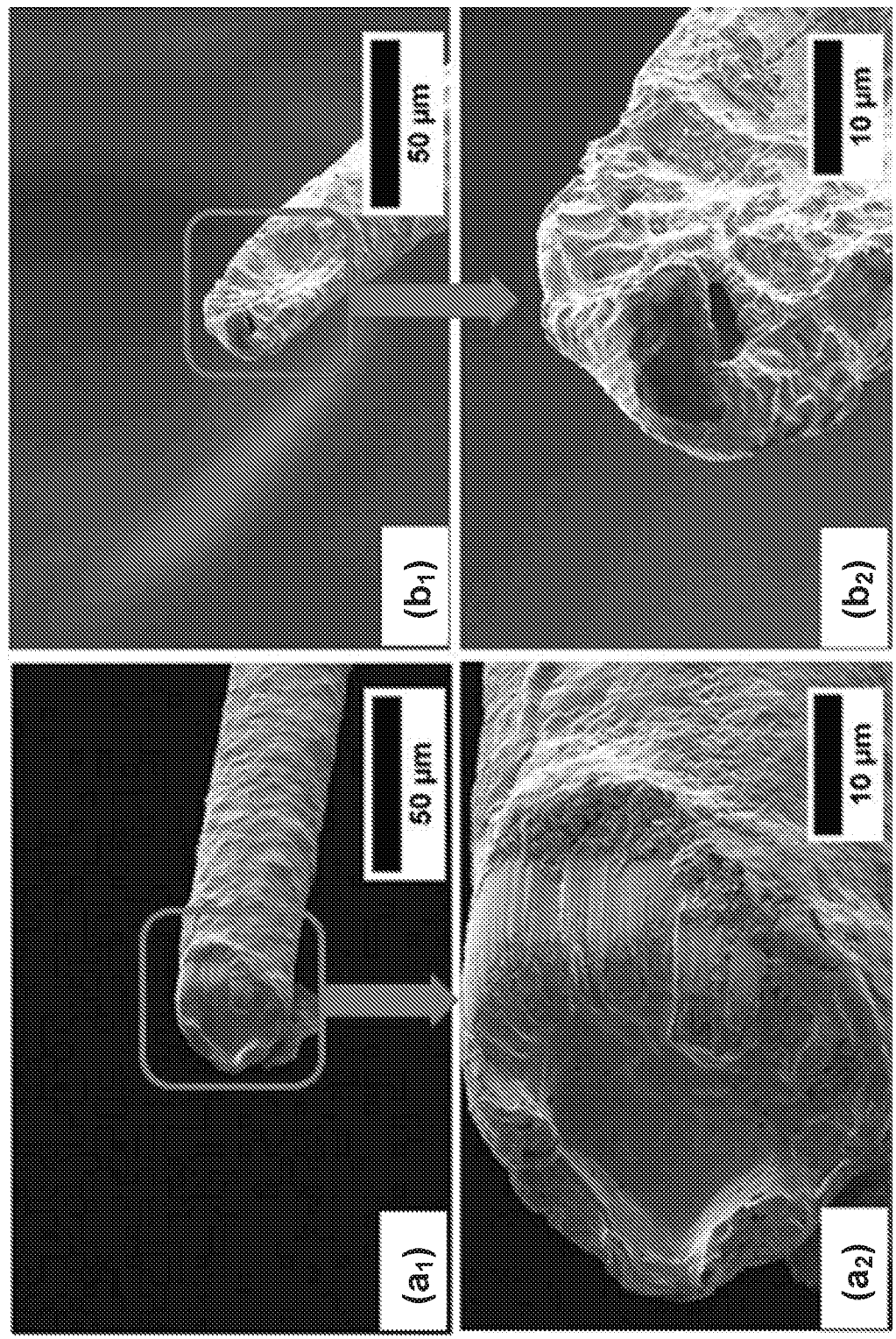

Morphology of Lignin/GA/PVA Fibers:

The SEM images of fiber facture tips after mechanical testing were shown in FIG. 10A and FIG. 10B. Both lignin/PVA fibers (in FIG. 10A) had fibrillar macrostructures-unlike GA/PVA fibers in FIG. 6. Fibrillar morphologies were due to high fiber draw ratios and lignin modified PVA, despite the aggregates shown among 30% lignin fibers (FIG. 10A). At high lignin concentration, lignin resided in polymer-poor domains of the gel structure which did little to aid its dispersion throughout fully drawn fiber. Thus at 30% lignin, fiber was not as strong as 5% lignin fiber. The addition of 0.8% GA2 into lignin/PVA yielded fibers with rough surfaces (FIG. 10B). Micro-voids were observed within the fiber. The compatibility between glucarate with lignin and PVA was poor; however, mechanical performance was not degraded.

Figure 11A:
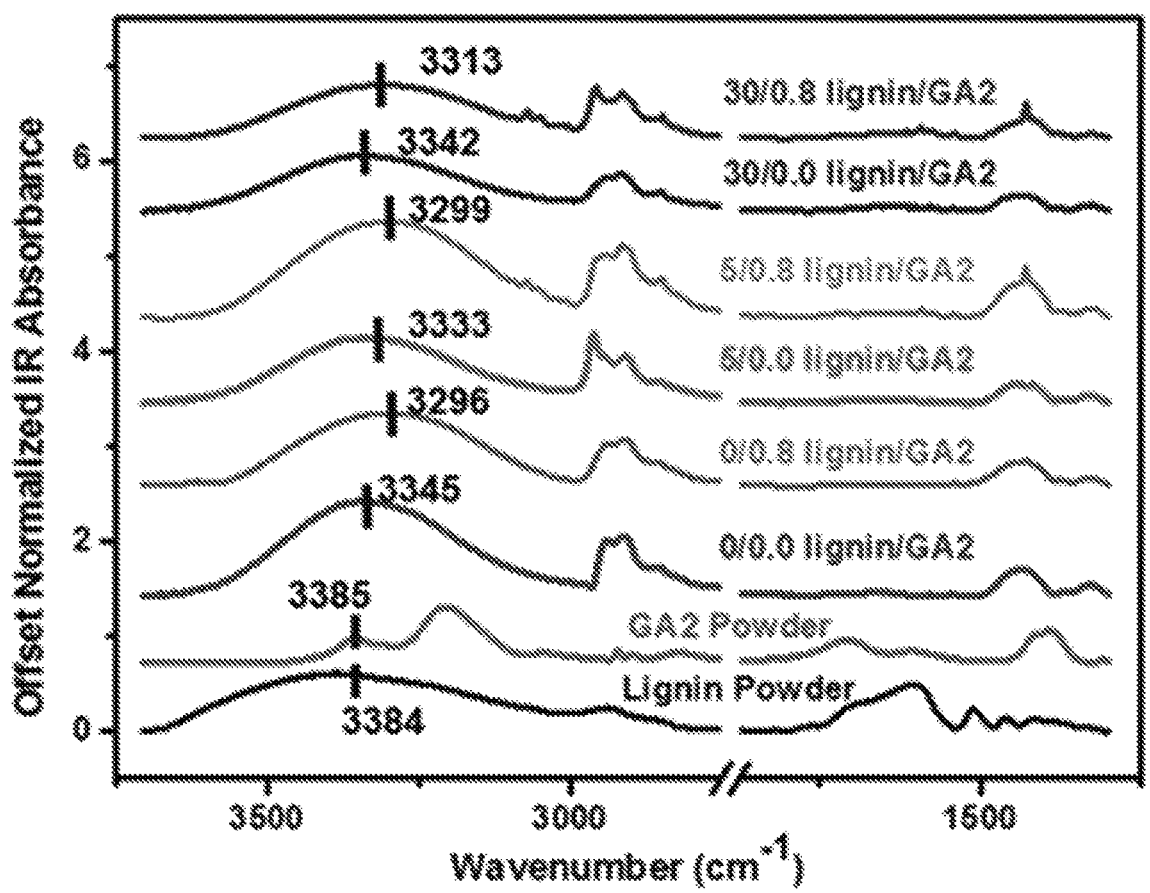
FIG. 11A-B are plots showing IR absorbance spectra of lignin, GA2 powder and modified PVA fibers between FIG. 11A: 3750-1000 $cm^{-1}$

Effect of Glucarate on Molecular Behaviors within Lignin/GA/PVA Fibers:

IR spectra of modified PVA fibers in the range of 3000-3700 $cm^{-1}$ provides insight into intermolecular adhesion. FIG. 11A shows hydrogen bonding within GA2 (3385 $cm^{-1}$), lignin (3384 $cm^{-1}$), and neat PVA fibers (3345 $cm^{-1}$). Among lignin/PVA fibers, the absorbance peak for hydrogen bonding shifted from 3345 $cm^{-1}$ for neat PVA towards 3333 $cm^{-1}$ for 5% lignin fiber and 3342 $cm^{-1}$ for 30% lignin. This behavior was indicative of greater intermolecular attraction between PVA and lignin at 5% lignin. At 0% lignin and 0.8% GA2, the absorbance peak for hydrogen bonding centered 3296 cm$^{-1}$. Hydroxyl group peaks shifted towards higher frequencies when both GA and lignin was present: to 3299 cm$^{-1}$ at 5% lignin and 3313 cm$^{-1}$ at 30% lignin. Among lignin containing fiber, hydrogen bonding was stronger when glucarate was present. In general, glucarate strengthened intermolecular adhesion due to their small size and polar functional groups.

Figure 11B:
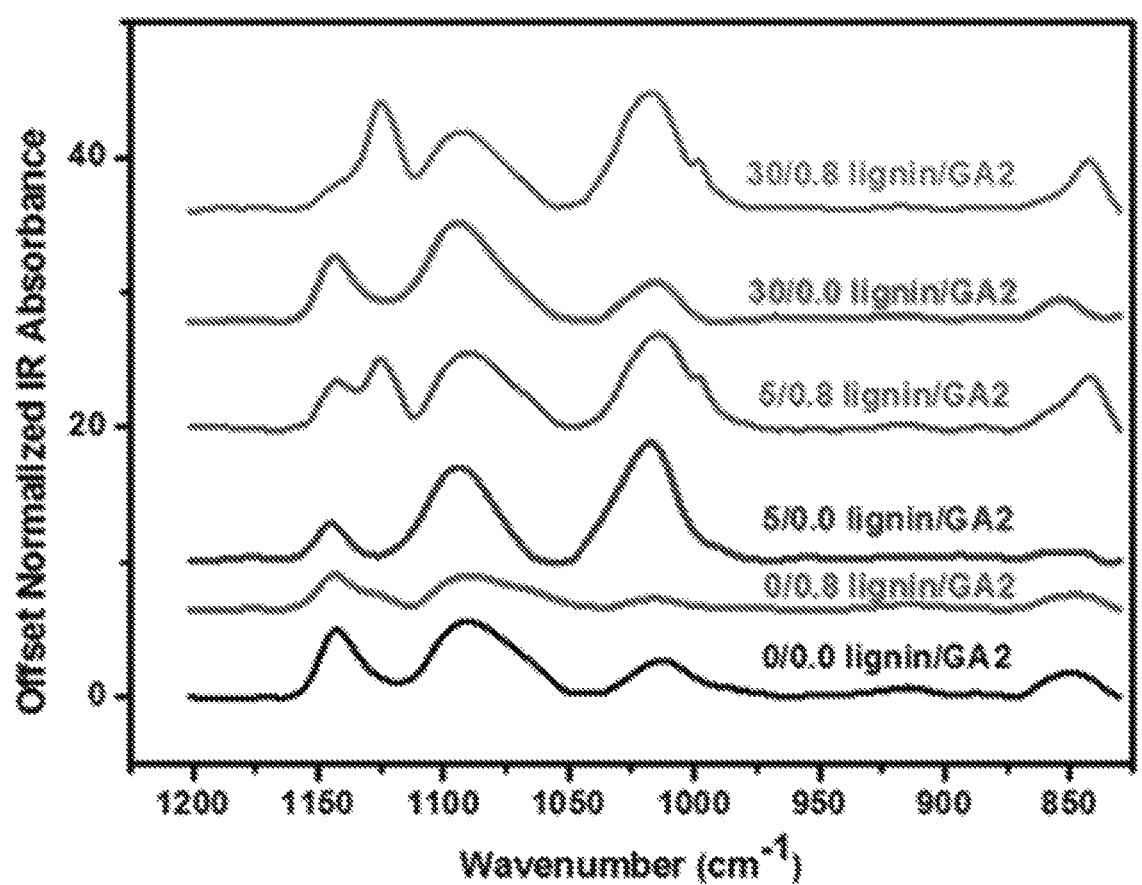

IR absorbance of GA2 (FIG. 11A) shows carboxylic acid-OH groups at 3200 cm$^{-1}$, carbonyl groups (C=O) at ~1700 cm$^{-1}$ and carboxylate (COO$^-$) stretch at ~1300 cm$^{-1}$. However, the intensities of these peaks were not strong enough for observation among the IR spectra of lignin/GA/PVA fibers. All modified PVA fibers had the —CH$_2$ group at 1445 cm$^{-1}$. Among lignin/GA2/PVA fibers it should be noted that 5/0.8 and 30/0.8 (lignin to PVA)/(GA2 to PVA) fibers' spectra had sharp peaks at 1430 cm$^{-1}$ that were imposed upon the broader 1445 cm$^{-1}$ peak. A small peak at ~1000 cm$^{-1}$ representing aliphatic bending of —CH=CH- appeared (FIG. 11B). This appearance of the 1430 cm$^{-1}$ denotes dehydration among glucarate molecules and cross-linking within fibers post drawing at temperatures above 200° C.

Figure 17:
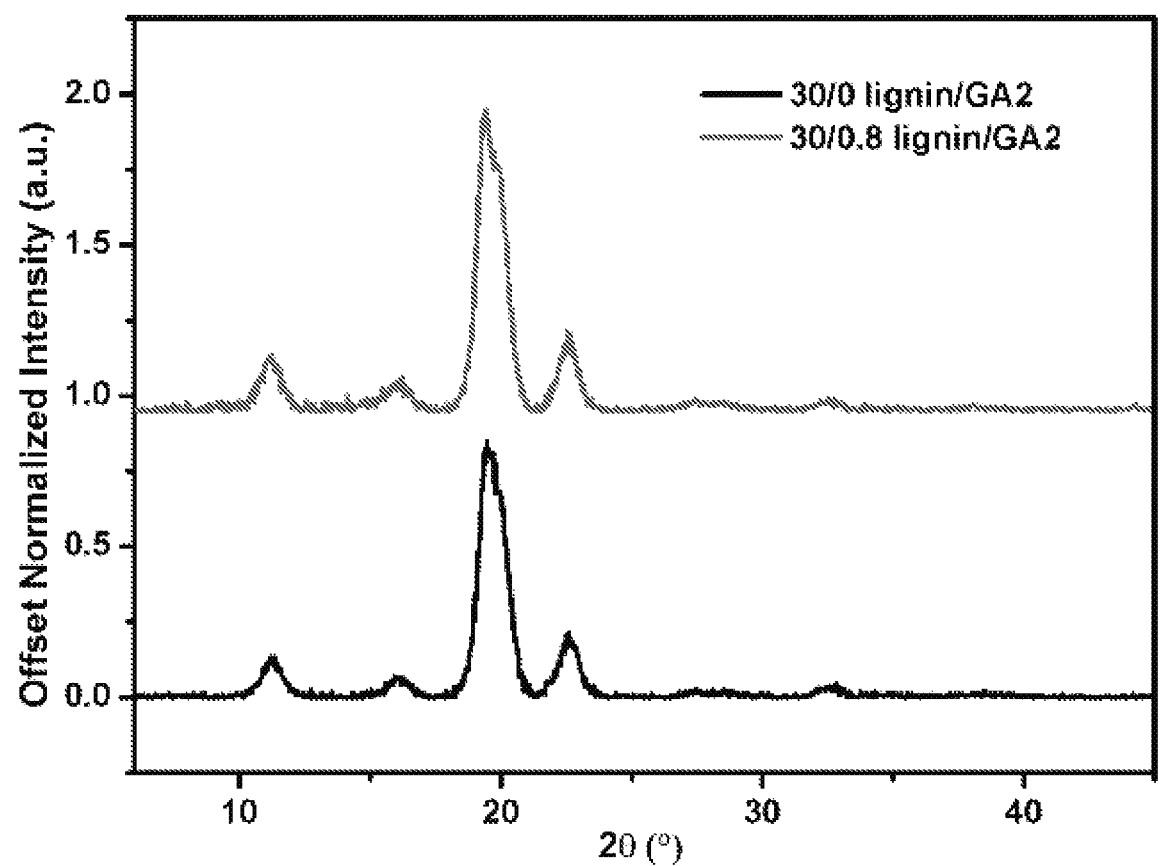
FIG. 17 is a plot showing wide-angle X-ray scattering diffractograms (WAXD) of fully drawn fibers: 30/0 lignin/GA2 and 30/0.8 lignin/GA2.

Among lignin/GA2/PVA fibers, GA2 induced a new crystalline form at 1130 cm$^{-1}$, which occurred alongside the neat PVA's crystalline form at 1144 cm$^{-1}$ (FIG. 11B). The 1130 cm$^{-1}$ peak for 5/0.8 lignin/GA2/PVA fiber was more intense than the 1144 cm$^{-1}$ peak. The 1130 cm$^{-1}$ peak for 30/0.8 lignin/GA2/PVA fiber was the prominent peak; whereas, the 1144 cm$^{-1}$ peak diminished as a shoulder. This suggested the new crystal conformation was due to the inclusion of glucarate within crystalline PVA regions of the lignin/GA2/PVA fibers. The new PVA crystalline form (containing glucarate) was not distinguishable from neat PVA according to X-ray diffractograms. FIG. 17 shows the X-ray diffractograms for 30/0 lignin/GA2/PVA and 30/0.8 lignin/GA2/PVA fibers.

Among lignin/GA2/PVA fibers, PVA has greater affinity for glucarate than lignin (FIG. 7A and FIG. 11A); thus, GA has priority over lignin to reside within the crystalline domains of PVA. The indices of fiber crystallinity are shown in Table 9. By adding 0.8% GA2, the crystallinity indices of 5% lignin fiber decreased from 3.0 to 2.2, whereas it slightly increased from 2.5 to 2.6 in 30% lignin fibers. This trend agreed well with the mechanical properties shown in FIG. 9A-FIG. 9C.

The normalized height of the hydrogen bonding peak (3345≥I$_{(OH)}$≥3296, from FIG. 11A) is listed in Table 9. In 5% lignin fibers, I$_{(OH)}$ value increased with addition of GA2. PVA's affinity to GA resulted in the increase of hydrogen bonding. The value of I$_{(OH)}$ in 30% lignin fibers was lower than that of 5% lignin fibers. It remains unchanged in 30% lignin fibers after adding GA2. Although GA2 engages in hydrogen bonding in PVA, the dehydration of glucarate at the high drawing temperature of 215° C. can negatively affect hydrogen bonding between adjacent PVA chains/monomer units within the 30% lignin fibers.

Based on the crystalline structure of thermally-drawn fibers, glucarate may preclude lignin within the polymer-rich domains of PVA gels fibers. PVA's preference for glucarate may also cause more lignin to reside in solvent-rich domains. Thus, lignin has migrated towards the fiber's outer surface during drawing, as solvent is excluded from the bulk of PVA fiber. This behavior was explored with a chemical analysis of fibers.

TABLE 9

IR Absorbance Ratio of A$_{(1144 + 1130)}$/A$_{854}$ and Normalized Peak Height of I$_{(OH)}$ from Fully Drawn Lignin/GA/PVA Fibers

| | (Lignin to PVA)/(GA2/PVA) Ratio | | | | | |
|---|---|---|---|---|---|---|
| | 0/0* | 0/0.8 | 5/0* | 5/0.8 | 30/0* | 30/0.8 |
| A$_{(1144+1130)}$/A$_{854}$ | 2.1 | 2.4 | 3.0 | 2.2 | 2.5 | 2.6 |
| I$_{(OH)}$ | 1.0 | 0.8 | 0.7 | 1.0 | 0.6 | 0.6 |

*No prominent crystalline peak shown at 1130 cm$^{-1}$, A$_{1144}$/A$_{854}$ value is used.

Figure 12A:
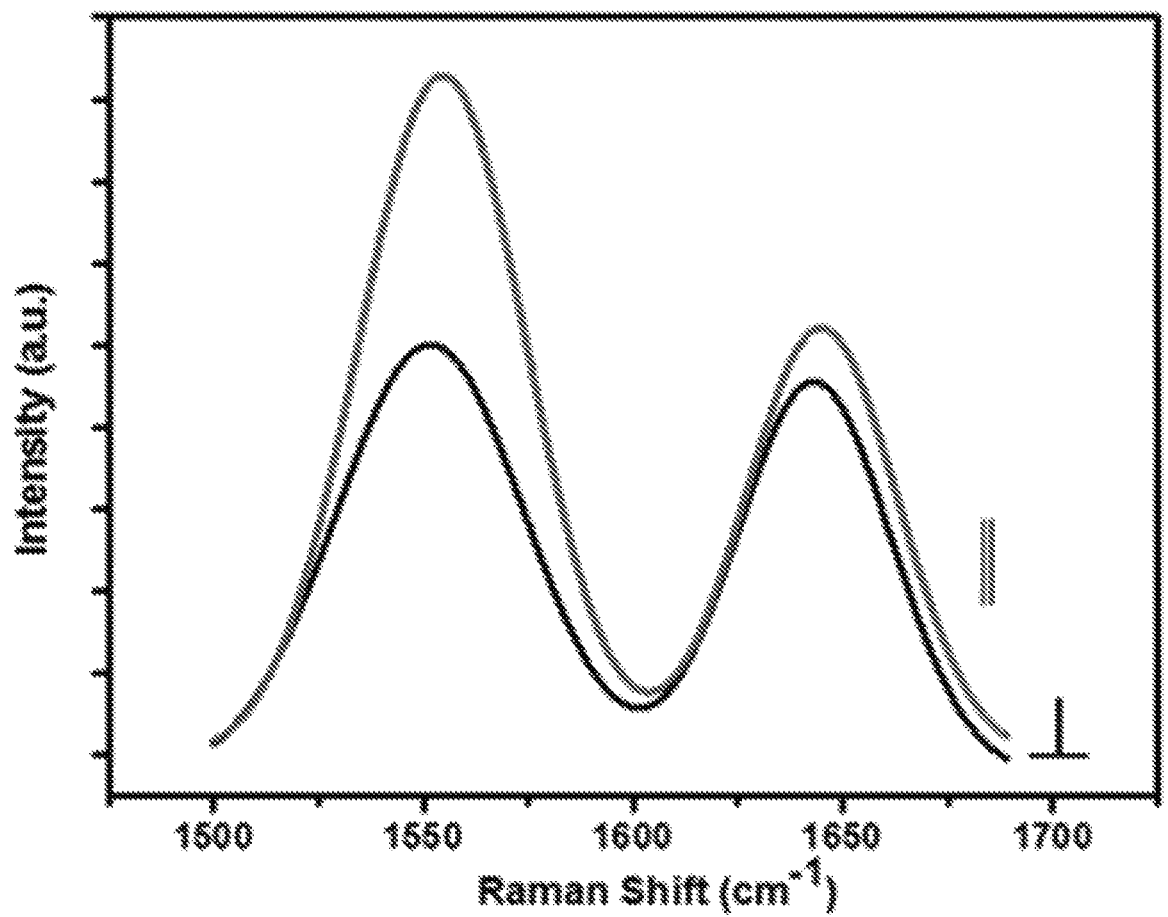
FIG. 12A-B are plots showing polarized Raman spectra of FIG. 12A: lignin
Figure 12B:
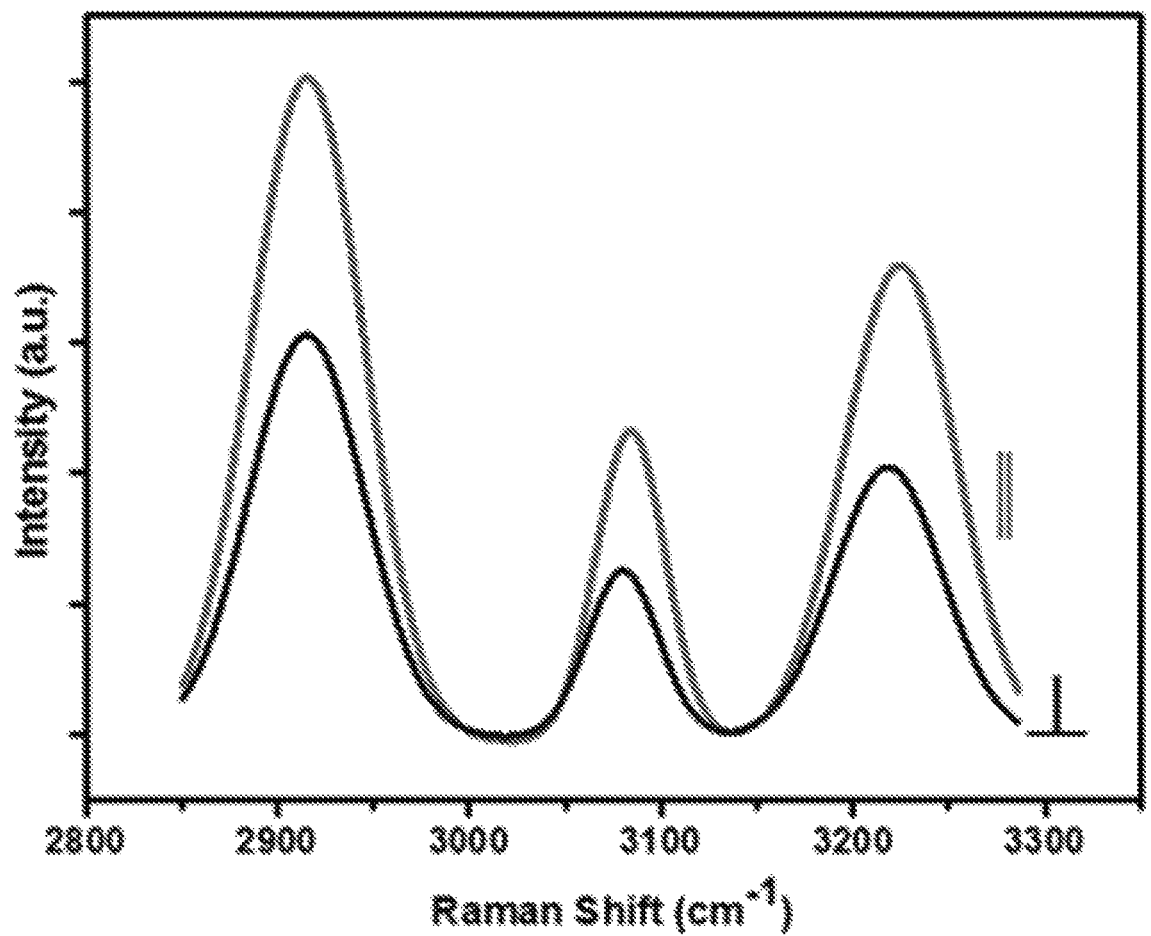

Effect of Glucarate on the Molecular Anisotropy of Lignin/GA/PVA Fiber:

Polarized Raman spectra of lignin and PVA chain alignment in 30/0.8 lignin/GA2 fiber is shown in FIG. 12A and FIG. 12B. The peak at ~1550 cm$^{-1}$ was assigned to phenol in-plane stretching, and the peak at ~1650 cm$^{-1}$ was assigned to conjugated C=C bonds in the lignin structure (FIG. 12A). In addition to C—H stretching at 2910 cm$^{-1}$ and —OH groups at 3210 cm$^{-1}$ along the PVA backbone, FIG. 12B shows the ~3090 cm$^{-1}$ peak that pertains to aliphatic lignin —OH groups. Raman orientation parameters for modified PVA fibers were listed in Table 10. Among 5% lignin fibers, the addition of GA2 did not increase R values for aliphatic lignin —OH groups, PVA's C—H and —OH groups. The orientation of lignin within fibers remained low, with f=0.12 for lignin phenolic groups. Glucarate did not effectively plasticize the spinning of 5% lignin/PVA fibers since the total draw ratio remained unchanged (Table 8).

Among 30% lignin fibers, molecular anisotropy R slightly increased for all functional groups representing PVA and lignin alignment along the fiber axis of lignin/GA2/PVA fiber. Orientation factor f for lignin aromatic rings increased mildly from 0.08 to 0.11. The addition of glucarate increased 30% lignin fiber's total draw ratio from 25 to 45× (Table 8) and resulted in the formation of a new conformation of PVA crystals (FIG. 11B). Thus, the mechanical performance of 30/0.8 lignin/GA2/PVA fibers was slightly greater than 30% lignin fibers, in despite of the phase separation between GA/PVA from PVA/lignin (FIG. 10B).

TABLE 10

Raman Orientation Parameters for Lignin and PVA within Lignin/GA/PVA Fibers

| | Lignin Content | 5% | | 30% | |
|---|---|---|---|---|---|
| | GA2 Content | 0.0% | 0.8% | 0.0% | 0.8% |
| Raman anisotropy (R) | PVA (C—H) | 1.8 | 1.8 | 1.5 | 1.7 |
| | PVA (—OH) | 1.6 | 1.8 | 1.1 | 1.8 |
| | Lignin (—OH) | 1.2 | 1.5 | 1.4 | 1.9 |
| | Lignin (aromatic ring) | 1.7 | 1.7 | 1.5 | 1.6 |
| | Lignin (C=C) | 1.6 | 1.6 | 1.5 | 1.6 |
| Orientation factor (f) | Lignin (aromatic ring) | 0.12 | 0.12 | 0.08 | 0.11 |
| | Lignin (C=C) | 0.11 | 0.11 | 0.08 | 0.11 |

Figure 13A:
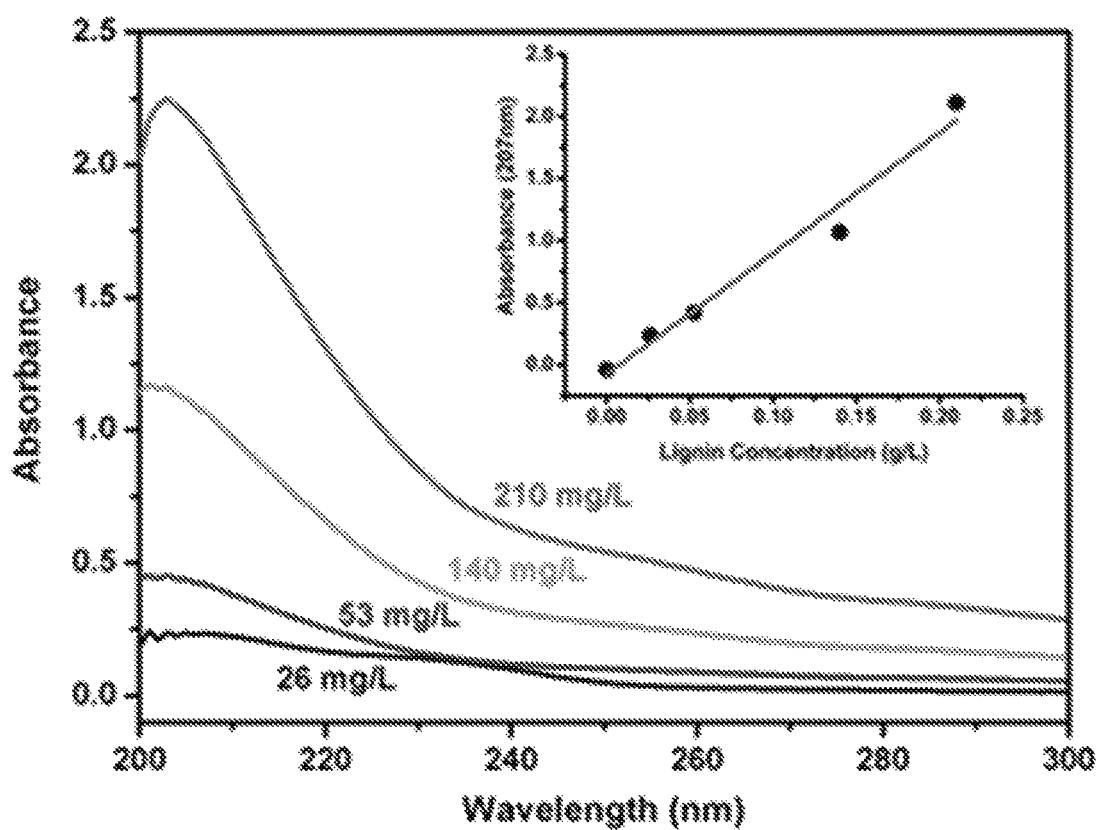
FIG. 13A-B are plots showing UV-vis spectra of FIG. 13A: control lignin/methanol solutions—the inset shows the calibration curve at 207 nm
Figure 13B:
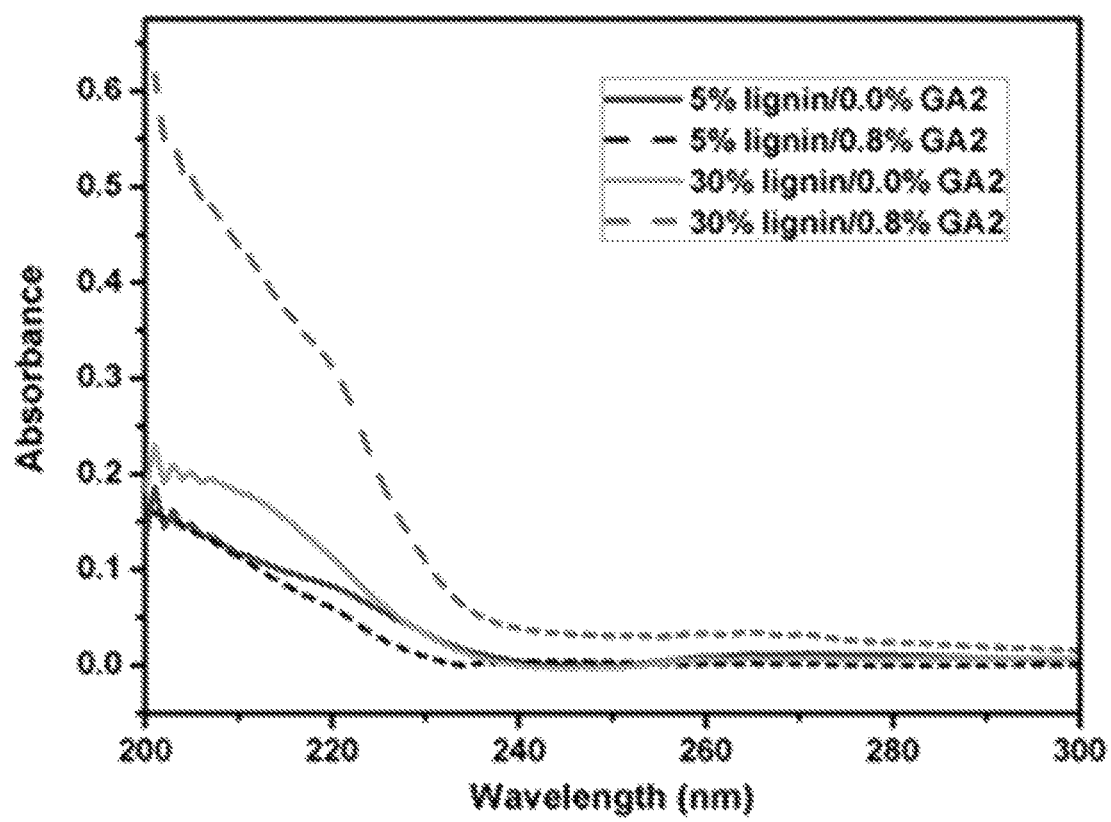

Determining Lignin's Location within Lignin/GA/PVA Fibers:

To test the assumption that lignin mostly resides along the outer surface of lignin/GA/PVA fibers, a quantitative chemical analysis was performed. UV-vis spectroscopy of control lignin/methanol solutions, at up to 210 mg/L, is shown in FIG. 13A. Lignin's aromatic functional groups have an absorbance peak at 207 nm. The calibration curve at 207 nm shows the linear relationship between lignin concentration and absorbance intensity. Neat PVA and 0.8% GA-based fibers were immersed in methanol; the corresponding solutions did not absorb between 200-300 nm (FIG. 15). Therefore, peak absorbance at 207 nm is only due to lignin's presence in methanol. UV-vis spectra of lignin removed from fibers is shown in FIG. 13B. Among lignin-based fibers, the incorporation of 0.8% GA2 resulted in even higher absorbance at 207 nm—an indication that more lignin had migrated from fiber to methanol. When comparing lignin/PVA fibers to lignin/GA2/PVA fibers, lignin diffusion from fiber slightly increased from 13.0 to 13.4 mg/L among 5% lignin fibers, but lignin diffusion drastically increased from 20.0 to 49.6 mg/L among 30% lignin fibers (Table 11). Since PVA is insoluble in methanol, lignin within the fiber core or well-integrated with PVA would be less accessible than lignin on the surface of fiber. The higher diffusion of lignin from lignin/GA/PVA fibers than from lignin/PVA at 30% lignin confirms PVA has greater affinity for GA2 than lignin. This data further concludes the phase separation observed among the lignin/GA/PVA fiber macrostructures.

TABLE 11

Lignin Concentration in Methanol after the Immersion of Lignin/GA2/PVA Fibers

| | Lignin Concentration in Fiber | | | | | |
|---|---|---|---|---|---|---|
| | 0% | | 5% | | 30% | |
| | GA2 Concentration in Fiber | | | | | |
| | 0.0% | 0.8% | 0.0% | 0.8% | 0.0% | 0.8% |
| Diffused Lignin Concentration in Methanol at 207 nm (mg/L) | — | — | 13.0 | 13.4 | 20.0 | 49.6 |

"—": Not Applicable: No UV-vis absorbance for fibers in 200-300 nm.

Figure 14A:
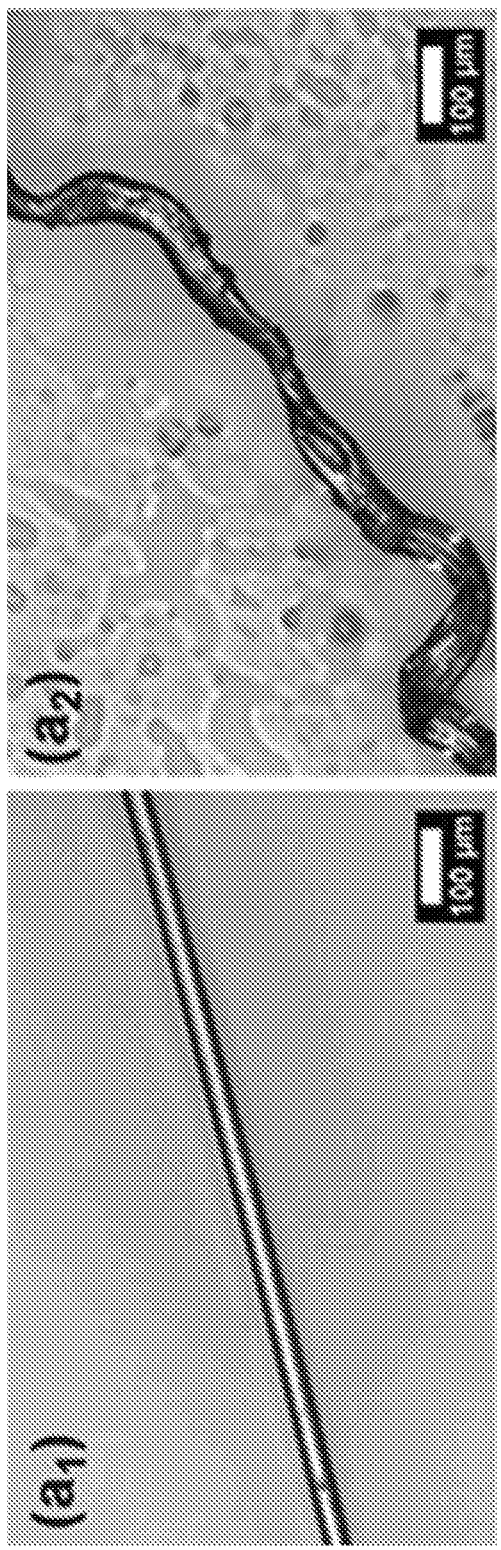
FIG. 14A-F are a series of images showing confocal micrographs of modified PVA fibers with (lignin to polymer)/(GA2 to polymer) ratio of FIG. 14A: 0/0.
Figure 14B:
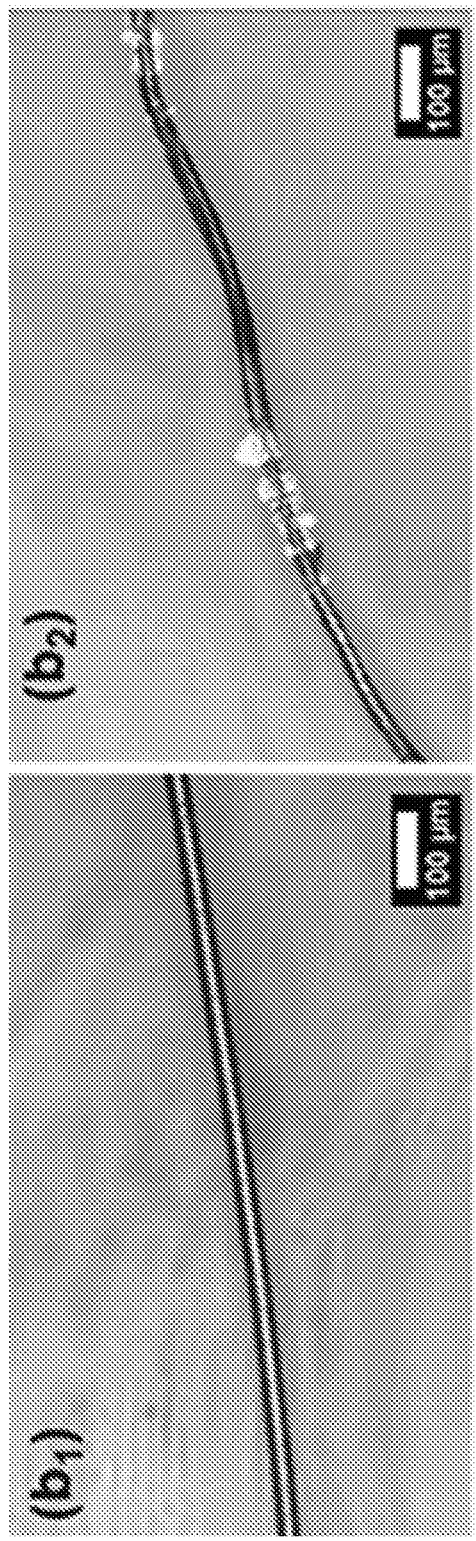

The water resistance of modified PVA fibers at room and elevated temperatures was observed with confocal microscopy (FIG. 14A-FIG. 14F). All fibers remained intact after immersion in 25° C. water. In 85° C. water, neat PVA fibers showed shrinkage and some dissolution (FIG. 14A). Although partial dissolution of 0.8% GA2 fiber in 85° C. water was observed (FIG. 14B), fiber structure was more intact than that of neat PVA fibers. Strong molecular adhesion between PVA with glucarate hindered fiber dissolution.

Figure 14C:
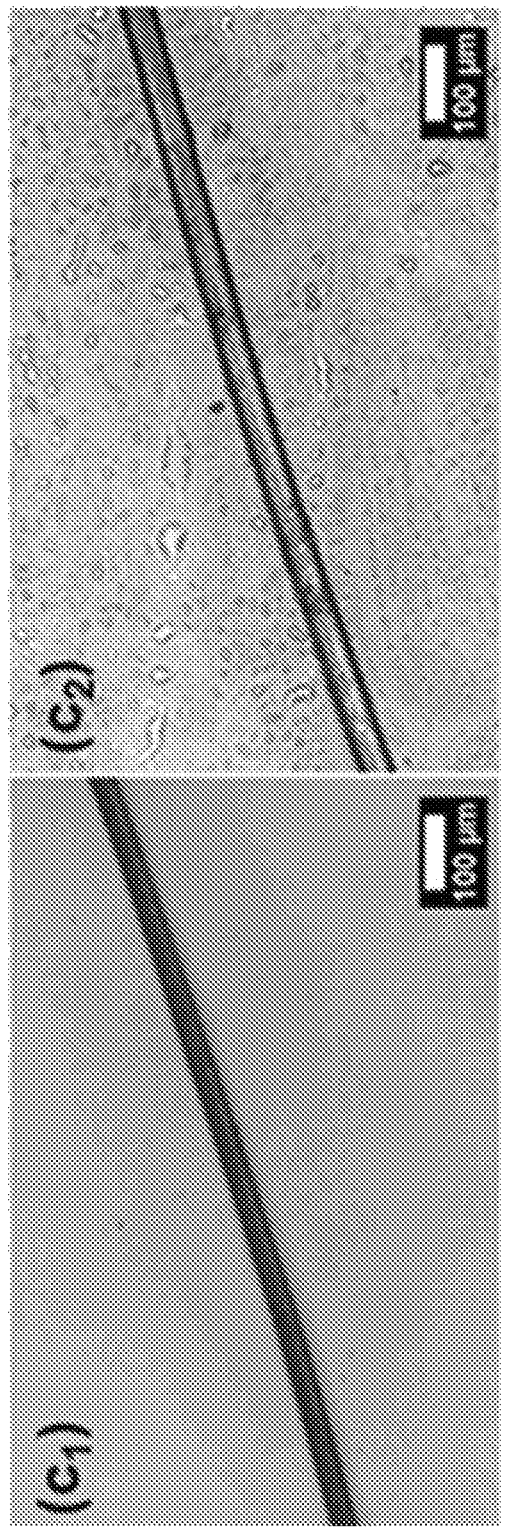
Figure 14D:
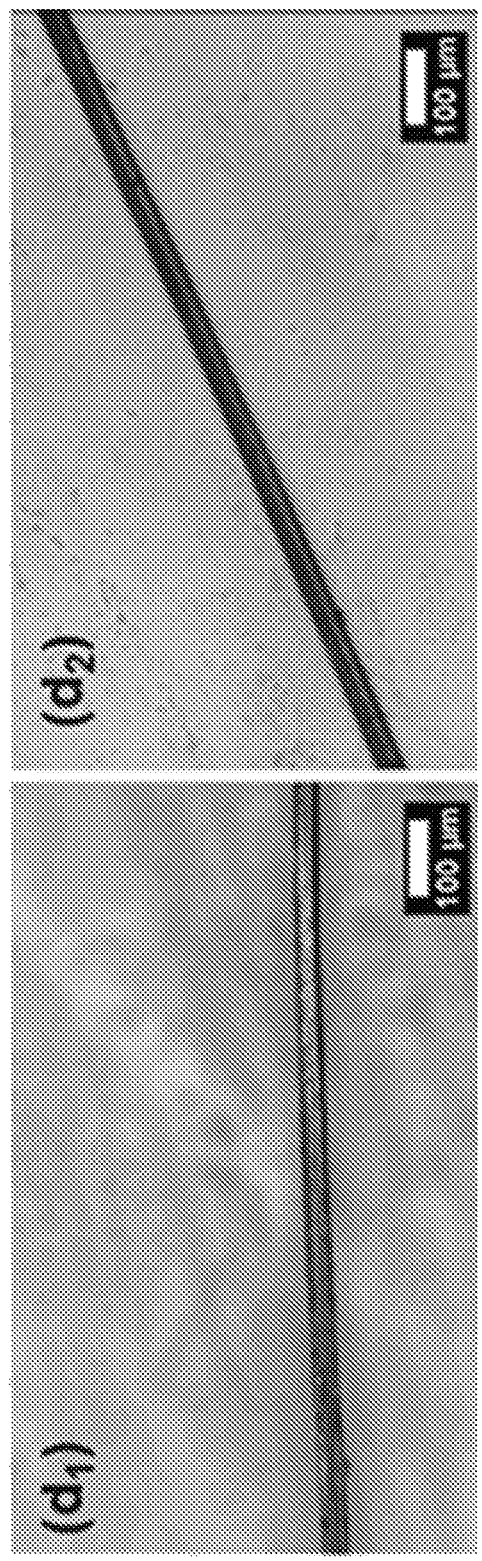
Figure 14E:
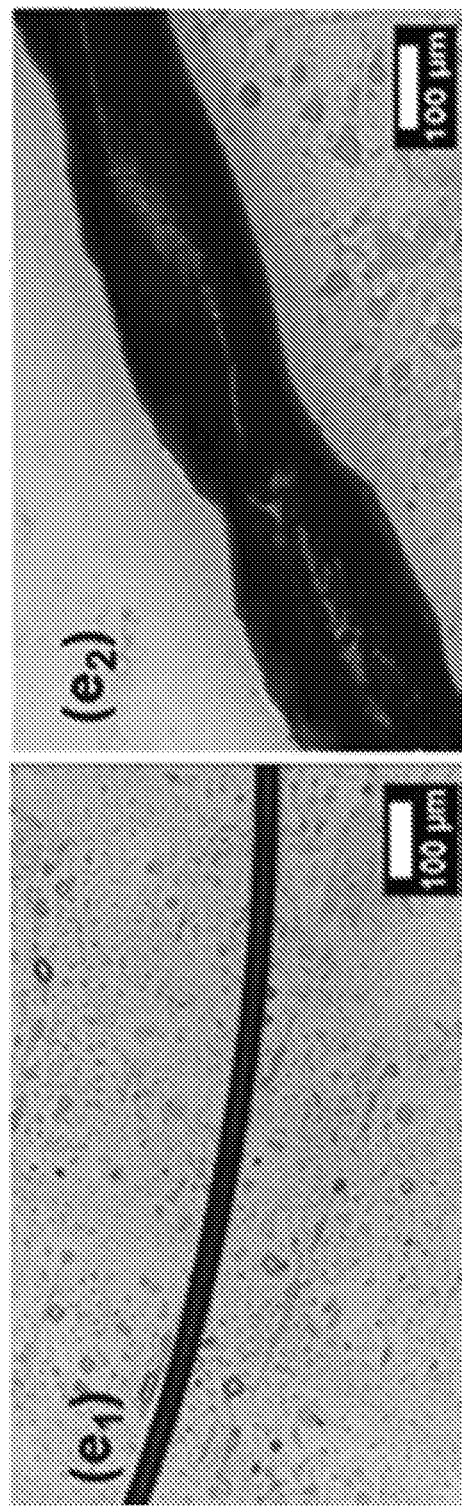
Figure 14F:
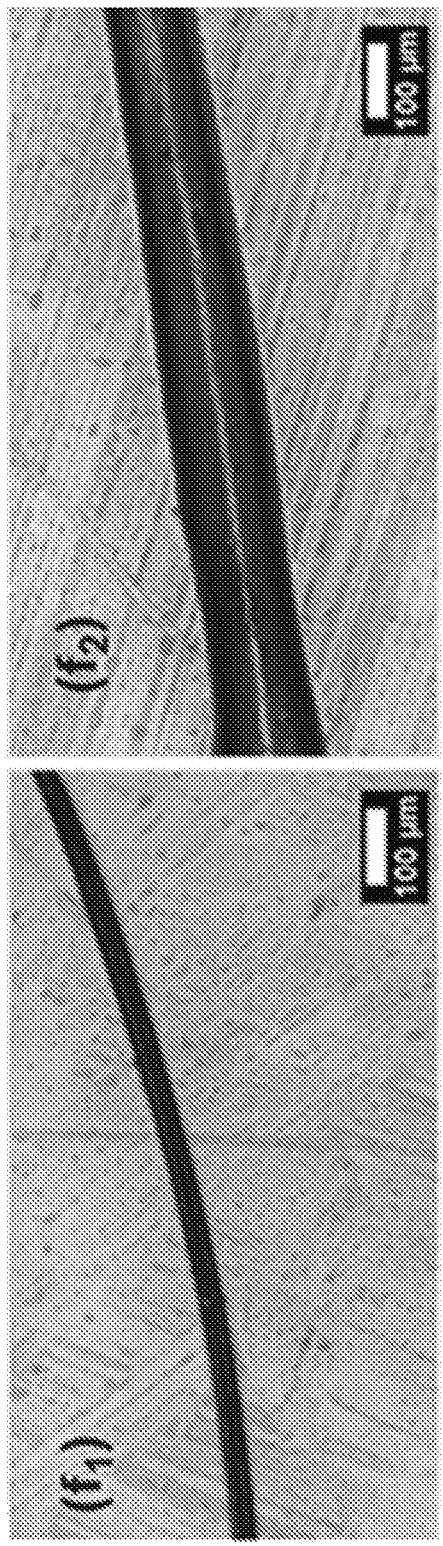

At 5% lignin, lignin/GA2/PVA fibers with 0 and 0.8% GA2 showed intact fiber structures in 85° C. water (FIG. 14C and FIG. 14D). Both fibers had minor swelling across their diameters. At 30% lignin, the lignin/PVA fiber immersed in 85° C. water appeared swollen and gel-like (FIG. 14E and FIG. 14F). At 30% lignin, fibers lacking glucarate swelled more than fibers containing 0.8% GA2. In lignin/glucarate/PVA fibers, glucarate strongly interacted with PVA, leaving more lignin along the fiber surface. Less water had swollen the structure of lignin/glucarate/PVA fibers versus lignin/PVA, when both contained 30% lignin. It is believed that water resistant lignin within modified PVA fibers functioned in a way similar to lignin's role in plant structures- to protect inner layers of semi-crystalline cellulose structure against water penetration.

Plasticizer Versus Anti-Plasticizer Behaviors on Polymers:

Table 12 summarizes the effects of additives on the processing and properties of polymers. Bio-based plasticizers such as glycerol, sorbitol and urea were used to facilitate the melt processing of polymers by decreasing their melting temperature. Polymer cohesion is disrupted by plasticizers, further the structural and mechanical performance of plasticized polymers are decreased. On the other hand, the incorporation of additives such as iodine, lignin and glucarate into solution-spun polymers effectively strengthened fibers. In contrast to plasticizers, these additives formed stronger molecular interactions with polymer and resulted in structural enhancement which favored higher mechanical properties performance. In contrast to iodine, lignin and glucarate increased fiber drawing temperatures, which are influenced by the polymer's crystalline relaxation temperature. According to the dynamic mechanical thermal analysis PVA/single-walled carbon nanotube composite fibers, SWNTs increase the crystalline relaxation temperature of nanocomposites relative to neat fiber. Thus, it was found that glucarate is a biobased, anti-plasticizer that can enhance the crystalline relaxation temperature of PVA.

TABLE 12

Influence of Additives on Polymer/Fiber Processing and Properties

| Additive | Processing Temperature | Mechanical Properties | Polymer Cohesion | Draw Ratio | Crystallinity ($X_c$%) | Water Resistance |
|---|---|---|---|---|---|---|
| Glycerol | Decrease $T_m$ | Decrease | Decrease | Increase | Decrease | Decrease |
| Urea | Decrease $T_m$ | Decrease | Decrease | Increase | Decrease | Decrease |
| Sorbitol | Decrease $T_m$ | Decrease | Decrease | Increase | Decrease | Decrease |
| Iodine | Drawing temperature decreased | Increase | Decrease | Increase | Increase | Increase |
| Lignin | Drawing stage temperature gradually increased | increase | Decrease | Increase | $X_c$ increases at low content; $X_c$ decreases at high concentration | Increase |
| Glucarate (this study) | Decreased Stage 1 draw temperature; increased stage 2-4 draw temperatures | Increase | Decrease | Increase | Increase | Increase |

Glucarate salts were shown to anti-plasticize the gel spinning of PVA fiber. Also, glucarate added to lignin/PVA fibers nearly maintained the mechanical performance of fibers, especially at 30% lignin. The anti-plasticizing behavior of glucarate within PVA fibers was evidenced in terms of gel melting point, processing conditions, and the structural and mechanical properties of fibers. Higher fiber drawing temperatures were observed among modified PVA fibers, due to changes in their crystalline relaxation temperatures. Fibers having the highest tensile strength and toughness were achieved when 0.8% glucaric acid mono-ammonium salt was added to PVA fiber. Performance enhancements among gel-spun glucarate/PVA fibers were attributed to high fiber draw ratios—caused by glucarate's anti-plasticization of PVA and strong intermolecular adhesion between PVA and glucarate. At 3% glucarate, thermal degradation of the glucarate during high temperature processing led to lower mechanical performance. Nevertheless, the mechanical strength and Young's modulus of glucarate/PVA fibers were competitive with commercial PVA staple fiber.

Glucarate and lignin individually anti-plasticizes PVA fibers and forms strong molecular interactions with PVA. However, the mixture of glucarate/lignin within PVA yielded fibers with macroscale phase separation. Interestingly, phase separation among lignin/PVA/glucarate fibers did not reduce the mechanical performance of PVA fibers below that of neat PVA fibers. The retention of PVA's overall crystallinity (though in a different form), strong intermolecular adhesion (between glucarate/PVA or lignin/PVA) and PVA's molecular orientation about the fiber axis are attributed with maintaining mechanical performance. Phase separation did result in lignin's residence at the fiber surface. As a result, its structure effectively suppressed fiber dissolution and swelling in high temperature water.

Example 3

PAN/Glucaric Acid Fibers

In similar methods as described in Examples 1 and 2. PVA was replaced with PAN and PAN/glucaric acid (GA) fibers, PAN/lignin fibers and PAN/GA/lignin fibers were provided via gel-spinning. Briefly, PAN having ~150 kDa molecular weight was obtained from Scientific Polymer. Kraft lignin was provided by BioChoice and was used as received. Monoammonium glucarate, having potassium or sodium impurities, was provided by Kalion.

PAN, PAN/lignin, PAN/GA, and PAN/GA/lignin fiber spinning dopes were made. PAN powder (up to 10 g) was dissolved in 50 mL of DMSO under constant stirring at 85° C. for approximately 8 to 18 hrs. Lignin solutions of 2 g/dL to 10 g/dL were sonicated in DMSO for at least 18 hrs. PAN was dissolved in the lignin/DMSO solution. PAN powder with glucaric acid at 1-5 wt % s were dissolved in 50 mL of DMSO under constant stirring at 85° C. for approximately 8 hrs. The final concentration of PAN in the spinning dopes was approximately 20 g/dL.

The spinning solutions were spun using a high pressure stainless steel syringe equipped with a 2 inch (50.8 mm) 19 gauge needle (0.69 mm inner diameter). The solution was allowed to equilibrate at room temperature (~22° C.) for about 2 hours before spinning.

The PAN/lignin solution was gelled in a −5° C. coagulation bath, having a gap distance of 2-8 mm from the tip of the needle. The resulting fibers were collected onto spools. Fibers were drawn through multiple stages of heated glycerol and high temperature silicone oil at temperatures between 110-250° C. The coagulation bath included methanol, isopropanol, and water.

For the 50/25/25 methanol/isopropanol/water coagulation bath, lignin/PAN solutions transformed into translucent, flexible gels. Minimal lignin leached from gel fibers into the coagulation bath for gel fibers containing up to 50% lignin.

Characterization of different PAN fibers are shown in Tables 13-15, which were prepared from the 50/25/25 methanol/isopropanol/water coagulation bath. Glucaric acid appeared to improve the spinnability of PAN and yield fine fibers. X % GA/PAN refers to mass of glucaric acid/mass of PAN.

TABLE 13

Mechanical Properties of Polyacrylonitrile/Glucaric Acid (PAN/GA) Fibers

| Fiber | Linear Density (denier) | Tensile Strength (MPa) | Modulus (GPa) |
|---|---|---|---|
| Neat PAN | 18 | 159 ± 18 | 3.6 ± 0.1 |
| 1.0% GA/PAN | 8 | 209 ± 63 | 4.2 ± 0.4 |
| 2.0% GA/PAN | 8 | 353 ± 60 | 5.8 ± 0.2 |
| 3.5% GA/PAN | 10 | 252 ± 44 | 5.0 ± 0.4 |
| 5.0% GA/PAN | 8 | 288 ± 51 | 6.1 ± 0.4 |

| Fiber | Linear Density (denier) | Tenacity (g/den) | Modulus (g/den) |
|---|---|---|---|
| Neat PAN | 18 | 1.5 ± 0.2 | 34.3 ± 0.7 |
| 1.0% GA/PAN | 8 | 2.0 ± 0.6 | 40.4 ± 3.4 |
| 2.0% GA/PAN | 8 | 3.4 ± 0.6 | 55.1 ± 1.9 |
| 3.5% GA/PAN | 10 | 2.4 ± 0.4 | 47.2 ± 3.8 |
| 5.0% GA/PAN | 8 | 2.7 ± 0.5 | 57.3 ± 3.7 |

| Fiber | Linear Density (dtex) | Tenacity (cN/dtex) | Modulus (cN/dtex) |
|---|---|---|---|
| Neat PAN | 20 | 1.3 ± 0.2 | 30.3 ± 0.6 |
| 1.0% GA/PAN | 9 | 1.8 ± 0.5 | 35.7 ± 3.5 |
| 2.0% GA/PAN | 9 | 3.0 ± 0.5 | 48.6 ± 1.7 |
| 3.5% GA/PAN | 11 | 2.1 ± 0.4 | 41.7 ± 3.3 |
| 5.0% GA/PAN | 9 | 2.4 ± 0.4 | 50.5 ± 3.3 |

TABLE 14

Mechanical Properties of Lignin/Polyacrylonitrile (Lignin/PAN) Fibers

| Fiber | Linear Density (denier) | Tensile Strength (MPa) | Modulus (GPa) |
|---|---|---|---|
| Neat PAN | 18 | 159 ± 18 | 3.6 ± 0.1 |
| 10% Lignin/PAN | 13 | 150 ± 28 | 5.4 ± 0.2 |
| 20% Lignin/PAN | 14 | 185 ± 20 | 5.7 ± 0.2 |
| 30% Lignin/PAN | 14 | 195 ± 27 | 5.9 ± 0.4 |
| 50% Lignin/PAN | 20 | 136 ± 16 | 4.2 ± 0.4 |

| Fiber | Linear Density (denier) | Tenacity (g/den) | Modulus (g/den) |
|---|---|---|---|
| Neat PAN | 18 | 1.5 ± 0.2 | 34.3 ± 0.7 |
| 10% Lignin/PAN | 13 | 1.4 ± 0.3 | 51.2 ± 2.2 |
| 20% Lignin/PAN | 14 | 1.7 ± 0.2 | 53.6 ± 2.0 |
| 30% Lignin/PAN | 14 | 1.8 ± 0.3 | 55.5 ± 3.9 |
| 50% Lignin/PAN | 20 | 1.3 ± 0.2 | 39.3 ± 3.4 |

| Fiber | Linear Density (dtex) | Tenacity (cN/dtex) | Modulus (cN/dtex) |
|---|---|---|---|
| Neat PAN | 20 | 1.3 ± 0.2 | 30.3 ± 0.6 |
| 10% Lignin/PAN | 14 | 1.3 ± 0.2 | 45.2 ± 2.0 |

TABLE 14-continued

Mechanical Properties of Lignin/Polyacrylonitrile (Lignin/PAN) Fibers

| 20% Lignin/PAN | 15 | 1.5 ± 0.2 | 47.3 ± 1.8 |
| 30% Lignin/PAN | 15 | 1.6 ± 0.2 | 49.0 ± 3.5 |
| 50% Lignin/PAN | 22 | 1.1 ± 0.1 | 34.7 ± 3.0 |

TABLE 15

Mechanical Properties of Lignin/Polyacrylonitrile/Glucaric Acid (Lignin/PAN/GA) Fibers

| Fiber | Linear Density (denier) | Tensile Strength (MPa) | Modulus (GPa) |
|---|---|---|---|
| Neat PAN | 18 | 159 ± 18 | 3.6 ± 0.1 |
| 3.5% GA/PAN | 10 | 252 ± 44 | 5.0 ± 0.4 |
| 50% Lignin/PAN | 20 | 136 ± 16 | 4.2 ± 0.4 |
| 3.5% GA/50% Lignin/PAN | 12 | 183 ± 15 | 5.3 ± 0.2 |

| Fiber | Linear Density (denier) | Tenacity (g/den) | Modulus (g/den) |
|---|---|---|---|
| Neat PAN | 18 | 1.5 ± 0.2 | 34.3 ± 0.7 |
| 3.5% GA/PAN | 10 | 2.4 ± 0.4 | 47.2 ± 3.8 |
| 50% Lignin/PAN | 20 | 1.3 ± 0.2 | 39.3 ± 3.4 |
| 3.5% GA/50% Lignin/PAN | 12 | 1.7 ± 0.1 | 48.4 ± 2.2 |

| Fiber | Linear Density (dtex) | Tenacity (cN/dtex) | Modulus (cN/dtex) |
|---|---|---|---|
| Neat PAN | 20 | 1.3 ± 0.2 | 30.3 ± 0.6 |
| 3.5% GA/PAN | 11 | 2.1 ± 0.4 | 41.7 ± 3.3 |
| 50% Lignin/PAN | 22 | 1.1 ± 0.1 | 34.7 ± 3.0 |
| 3.5% GA/50% Lignin/PAN | 14 | 1.5 ± 0.1 | 42.7 ± 1.9 |

PAN fibers containing 2% GA were more than twice as strong as neat PAN fibers (at 159 MPa in tensile strength). At 2% GA. PAN/GA fibers had a tensile modulus of 5.8 GPa in comparison to neat PAN fibers at 3.6 GPa.

In Table 14, fibers having 20-30% lignin were stronger than neat PAN. The mechanical strength of PAN fibers decreased from 159 MPa for neat fibers to 136 MPa for 50% lignin fibers. However, the tensile modulus at 50% lignin remained higher than for neat PAN fibers.

In Table 15, glucaric acid (at 3.5% GA) increased the mechanical performance of PAN fibers. Even at 50% lignin, lignin/PAN/GA fibers were mechanically stronger (having a higher tensile strength and tensile modulus) than neat PAN fibers.

For comparison, mechanical properties of PAN and PAN composited fibers are shown below in Table 16.

TABLE 16

Mechanical Properties and Molecular Weights of PAN and Composite PAN Fibers

| Reference | Modulus (g/den) | Breaking Strength (g/den) | Molecular Weight (kDa) |
|---|---|---|---|
| Tan 2010[1] | 121.9 | 7.5 | 78 |
| Chae 2007[2] | 163.4 | 6.6 | 250 |
| Liu 2011[3] | 110.7 | 7.0 | 78 |
| PAN/lignin (20%) fibers | 53.6 | 1.7 | 150 |

[1] Tan, L.; Liu, S.: Song, K.; Chen, H.: Pan, D. Gel-Spun Polyacrylonitrile Fiber From Pregelled Spinning Solution. *Polymer Engineering and Science* 2010, 50, 1290.

[2] Chae, H. G.; Minus, M. L.: Rasheed, A.: Kumar, S. Stabilization and carbonization of gel spun polyacrylonitrile/single wall carbon nanotube composite fibers. *Polymer* 2007, 48, 3781.

[3] Liu, S.; Tan, L.: Pan, D.; Chen, Y. Gel spinning of polyacrylonitrile fibers with medium molecular weight. *Polymer International* 2011, 60, 453. These three reference are all incorporated by reference herein in their entirety.

5. Exemplary Embodiments

For reasons of completeness, various aspects of the invention are set out in the following numbered clauses:

Clause 1. A composition comprising: a polymer having a plurality of hydroxyl groups or nitrile groups; and an aldaric acid or a salt thereof.

Clause 2. The composition of clause 1, wherein the aldaric acid is glucaric acid.

Clause 3. The composition of either clause 1 or clause 2, wherein the polymer comprises a straight or branched polyalkylene substituted with the plurality of hydroxyl groups or nitrile groups.

Clause 4. The composition of any of clauses 1-3, wherein the polymer comprises recurring units of the formula (I)

(I)

wherein: L is $C_{0-3}$ alkylene; X is —OH or nitrile; n is 1 to 1000; and m is 100 to 100,000.

Clause 5. The composition of any of clauses 1-4, wherein the polymer has a plurality of hydroxyl groups.

Clause 6. The composition of any of clauses 1-5, wherein the polymer comprises a straight or branched polyalkylene substituted with the plurality of hydroxyl groups.

Clause 7. The composition of any of clauses 1-6, wherein the polymer comprises recurring units of the formula (II)

(II)

wherein: n is 1 to 1000, and m is 100 to 100,000.

Clause 8. The composition of any of clauses 1-7, wherein the polymer comprises polyvinyl alcohol, polyvinyl alcohol derivatives, polyvinyl alcohol copolymers, or a combination thereof.

Clause 9. The composition of any of clauses 1-8, wherein the composition consists essentially of polyvinyl alcohol and glucaric acid or a salt thereof.

Clause 10. The composition of any of clauses 1-9, wherein the composition consists of polyvinyl alcohol and glucaric acid or a salt thereof.

Clause 11. The composition of any of clauses 1-4, wherein the polymer has a plurality of nitrile groups.

Clause 12. The composition of any of clauses 1-4 or 11, wherein the polymer comprises a straight or branched polyalkylene substituted with the plurality of nitrile groups.

Clause 13. The composition of any of clauses 1-4 or 11-12, wherein the polymer comprises recurring units of the formula (III)

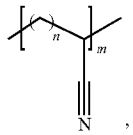
(III)

wherein: n is 1 to 1000, and m is 100 to 100,000.

Clause 14. The composition of any of clauses 1-4 or 11-13, wherein the polymer comprises polyacrylonitrile, polyacrylonitrile derivatives, polyacrylonitrile copolymers, or a combination thereof.

Clause 15. The composition of clause 14, wherein the polyacrylonitrile copolymer is a copolymer of polyacrylonitrile and another polymer selected from the group consisting of acrylic acid, itaconic acid, and acrylates.

Clause 16. The composition of any of clauses 1-4 or 11-14, wherein the composition consists essentially of polyacrylonitrile and glucaric acid or a salt thereof.

Clause 17. The composition of any of clauses 1-4, 11-14, or 16, wherein the composition consists of polyacrylonitrile and glucaric acid or salt thereof.

Clause 18. The composition of any of clauses 1-17, wherein the polymer has a molecular weight of from about 100 kDa to about 400 kDa.

Clause 19. The composition of any of clauses 1-18, comprising the polymer at from about 30% to about 99.9% by weight of the composition.

Clause 20. The composition of any of clauses 2-19, comprising the glucaric acid or a salt thereof at from about 0.01% to about 10% by weight of the composition.

Clause 21. The composition of any of clauses 2-20, comprising the polymer and the glucaric acid at a weight ratio of from about 5/1 to about 10,000/1 (polymer/glucaric acid).

Clause 22. The composition of any of clauses 1-21, further comprising an additive.

Clause 23. The composition of any of clauses 1-22, wherein the additive is selected from the group consisting of lignin, carbon nanotubes, nanofillers and a combination thereof.

Clause 24. The composition of any of clauses 1-23, further comprising lignin.

Clause 25. The composition of any of clauses 1-24, comprising lignin at from about 0.1% to about 50% by weight of the composition.

Clause 26. The composition of any of clauses 2-25, wherein the glucaric acid is an ammonium salt of glucaric acid.

Clause 27. A fiber comprising the composition of any of clauses 1-26.

Clause 28. The fiber of clause 27, having an average diameter of from about 10 μm to about 50 μm.

Clause 29. The fiber of either clause 27 or clause 28, having a tenacity of greater than 5 g/den.

Clause 30. The fiber of any of clauses 27-29, having a specific modulus of greater than 250 g/den.

Clause 31. The fiber of any of clauses 27-30, having a tensile strength of greater than 500 MPa.

Clause 32. The fiber of any of clauses 27-31, having a linear density of less than 15 denier.

Clause 33. The fiber of any of clauses 27-32, wherein the fiber is melt-blown, spunbond, or gel-spun.

Clause 34. A concrete additive comprising the fiber of any of clauses 27-33.

Clause 35. A fibrous article comprising the fiber of any of clauses 27-33.

Clause 36. The fibrous article of clause 35, wherein the article is selected from the group consisting of yarn, fabric, melt-blown web, spunbonded web, gel-spun web, thermobonded web, hydroentangled web, nonwoven fabric, and a combination thereof.

Clause 37. A method of making a fiber, the method comprising: dissolving a polymer having a plurality of hydroxyl and/or nitrile groups and an aldaric acid or a salt thereof in a first solvent to provide a solution; heating the solution; extruding the solution into a first bath comprising a second solvent to provide a gel-spun fiber; aging the gel-spun fiber to provide an aged gel-spun fiber; and drawing the aged gel-spun fiber through a second bath comprising silicone oil to provide the fiber.

Clause 38. The method of clause 37, wherein the aldaric acid is present in the solution at from about 0.01% to about 5% by weight/volume.

Clause 39. The method of either clause 37 or clause 38, wherein the polymer is present in the solution at from about 60% to about 99.9% by weight/volume.

Clause 40. The method of any of clauses 37-39, wherein the first solvent comprises DMSO, water, urea or a combination thereof.

Clause 41. The method of any of clauses 37-40, wherein the second solvent comprises methanol, acetone, isopropanol, water or a combination thereof.

Clause 42. The method of any of clauses 37-41, wherein drawing the aged gel-spun fiber includes 1 to 4 stages.

Clause 43. The method of any of clauses 37-42, wherein the aldaric acid is glucaric acid.

What is claimed is:

1. A composition comprising:
   a polymer having a plurality of hydroxyl groups or nitrile groups;
   an aldaric acid or a salt thereof: and
   an additive selected from the group consisting of lignin, carbon nanotubes, nanofillers and a combination thereof.

2. The composition of claim 1, wherein the aldaric acid is glucaric acid.

3. The composition of claim 1, wherein the polymer comprises a straight or branched polyalkylene substituted with the plurality of hydroxyl groups or nitrile groups.

4. The composition of claim 1, wherein the polymer comprises recurring units of the formula (I)

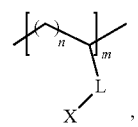
(I)

wherein:
L is $C_{0-3}$ alkylene;
X is —OH or nitrile;
n is 1 to 1000; and
m is 100 to 100,000.

5. The composition of claim 1, wherein the polymer comprises polyvinyl alcohol, polyvinyl alcohol derivatives, polyvinyl alcohol copolymers, or a combination thereof.

6. The composition of claim 1, wherein the polymer comprises polyacrylonitrile, polyacrylonitrile derivatives, polyacrylonitrile copolymers, or a combination thereof.

7. The composition of claim 6, wherein the polyacrylonitrile copolymer is a copolymer of polyacrylonitrile and another polymer selected from the group consisting of acrylic acid, itaconic acid, and acrylates.

8. The composition of claim 1, wherein the polymer has a molecular weight of from about 100 kDa to about 400 kDa.

9. The composition of claim 1, comprising the polymer at from about 30% to about 99.9% by weight of the composition.

10. The composition of claim 2, comprising the glucaric acid or a salt thereof at from about 0.01% to about 10% by weight of the composition.

11. The composition of claim 2, comprising the polymer and the glucaric acid at a weight ratio of from about 5/1 to about 10,000/1 (polymer/glucaric acid).

12. The composition of claim 2, wherein the glucaric acid is an ammonium salt of glucaric acid.

13. A fiber comprising the composition of claim 1.

14. The fiber of claim 13, having at least one of:
   (i) an average diameter of from about 10 μm to about 50 μm;
   (ii) a tenacity of greater than 5 g/den;
   (iii) a specific modulus of greater than 250 g/den;
   (iv) a tensile strength of greater than 500 MPa; and
   (v) a linear density of less than 15 denier.

15. A concrete additive comprising the fiber of claim 13.

16. A fibrous article comprising the fiber of claim 13, wherein the article is selected from the group consisting of yarn, fabric, melt-blown web, spunbonded web, gel-spun web, thermobonded web, hydroentangled web, nonwoven fabric, and a combination thereof.

17. A method of making a fiber, the method comprising:
   dissolving a polymer having a plurality of hydroxyl and/or nitrile groups and an aldaric acid or a salt thereof in a first solvent to provide a solution;
   heating the solution;
   extruding the solution into a first bath comprising a second solvent to provide a gel-spun fiber;
   aging the gel-spun fiber to provide an aged gel-spun fiber; and
   drawing the aged gel-spun fiber through a second bath comprising silicone oil to provide the fiber.

18. The method of claim 17, wherein the aldaric acid is present in the solution at from about 0.01% to about 5% by weight/volume.

19. The method of claim 17, wherein the aldaric acid is glucaric acid.

* * * * *